US006596522B2

(12) United States Patent
Tsien et al.

(10) Patent No.: US 6,596,522 B2
(45) Date of Patent: *Jul. 22, 2003

(54) DETECTION OF TRANSMEMBRANE POTENTIALS BY OPTICAL METHODS

(75) Inventors: Roger Y. Tsien, La Jolla, CA (US); Jesus E. Gonzalez, III, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/378,534

(22) Filed: Aug. 20, 1999

(65) Prior Publication Data

US 2002/0137201 A1 Sep. 26, 2002

Related U.S. Application Data

(63) Continuation of application No. 08/765,860, filed as application No. PCT/US96/09652 on Jun. 6, 1996, now Pat. No. 6,107,066.

(51) Int. Cl.[7] .............................. C12N 13/00; C12Q 1/02
(52) U.S. Cl. ......................... 435/173.4; 435/29; 436/63; 436/172; 436/519; 436/546; 436/800; 436/805
(58) Field of Search .................................. 436/519, 520, 436/546, 800, 63, 172, 805; 435/173.4, 29

(56) References Cited

U.S. PATENT DOCUMENTS

| | | | |
|---|---|---|---|
| 4,560,665 A | 12/1985 | Nakae et al. ............... 436/63 |
| 4,861,727 A | 8/1989 | Hauenstein et al. | |
| 4,900,934 A | 2/1990 | Peeters et al. | |
| 5,244,813 A | 9/1993 | Walt et al. | |
| 5,661,035 A | * 8/1997 | Tsien et al. | |
| 6,107,066 A | * 8/2000 | Tsien et al. | |

FOREIGN PATENT DOCUMENTS

| | | | | |
|---|---|---|---|---|
| EP | 137515 A2 | 10/1984 | | |
| EP | 397641 A2 | 4/1990 | | |
| EP | 429907 A2 | 11/1990 | | |
| EP | 520262 A1 | 6/1992 | | |
| EP | 552107 A1 | 1/1993 | | |
| WO | WO9508637 | 3/1995 | | |
| WO | WO9527204 | 10/1995 | | |
| WO | WO 96/41166 | 12/1996 | ......... | G01N/33/50 |
| WO | WO 98/30715 | 7/1998 | | |

OTHER PUBLICATIONS

Bechtel, "Synthesis of Styryl Dyes Containing Reactive Groups," *Department of Organic and Macromolecular Chemistry at the Heinrich Heine University of Düsseldorf*, 36 pgs (Sep. 1993 to Apr. 1994).
Gonzalez and Tsien, "Improved Indicators of Cell Membrane Potential that use Fluorescence Energy Transfer," *Chemistry and Biology*, 4(4):269–277 (1997).
Witzak, "Oxonol Luminophores Containing Functionalized Side Chains," *Department of Organic and Macromolecular Chemistry at the Heinrich Heine University of Düsseldorf*, 48 pgs, (Oct. 1993 to Jun. 1994).
Niles et al., "Resonance Energy Transfer Imaging of Phospholipid Vesicle Interaction with a Planar Phospholipid Membrane," *J. Gen. Phystol.* The Rockefeller University Press vol. 107 Mar. 1996 (pp. 329–351).
Wilson et al., "Lymphocyte Membrane Potential and $Ca^{2+}$—Sensitive Potassium Channels Described by Oxonol Dye Fluorescence Measurements," *Journal of Cellular Physiology* 125:72–81 (1985).
Wilson et al., "Voltage–Sensitive Cyanine Dye Fluorescence Signals in Lymphocytes: Plasma Membrane and Mitochondrial Components," *Journal of Cellular Physiology* 125:61–71 (1985).
Bechtel, Sandra, "Synthese von Styrylfarbstoffen mit Reaktivgruppen," (foreign language), *ausgefuhrt am Institut fur Organische und Makromolekulare Chemie der HeinrichHeine–Universitat Dusseldorf*, Sep. 1993 bis Apr. 1994, pp. 1–65.
Malinski, Tadeusz et al., "Fluorescene Measurement of Membrane Potential Changes," *Applied Fluorescene Technology*, vol. III, No. 1, Feb. 1991, pp. 1–7.
Szollosi, Janos et al., "Fluorescence Energy Transfer and Membrane Potential Measurements Monitor Dynamic Properties of Cell Membranes: A Critical Review," *Prog. Biophys. Molec. Biol.*, vol. 49, 1987, pp. –

(List continued on next page.)

*Primary Examiner*—Mary E. Ceperley
(74) *Attorney, Agent, or Firm*—Gray Cary Ware & Freidenrich, LLP; Lisa A. Haile

(57) ABSTRACT

Methods and compositions are provided for determining the potential of a membrane. In one aspect, the method comprises:

(a) introducing a first reagent comprising a hydrophobic fluorescent ion capable of redistributing from a first face of the membrane to a second face of the membrane in response to changes in the potential of the membrane, as described by the Nernst equation, (b) introducing a second reagent which labels the first face or the second face of the membrane, which second reagent comprises a chromophore capable of undergoing energy transfer by either (i) donating excited state energy to the fluorescent ion, or (ii) accepting excited state energy from the fluorescent ion, (c) exposing the membrane to radiation;

(d) measuring energy transfer between the fluorescent ion and the second reagent, and (e) relating the energy transfer to the membrane potential.

Energy transfer is typically measured by fluorescence resonance energy transfer. In some embodiments the first and second reagents are bound together by a suitable linker.

In one aspect the method is used to identify compounds which modulate membrane potentials in biological membranes.

82 Claims, 21 Drawing Sheets

OTHER PUBLICATIONS

Witzak, Dorett, "Oxonol–Luminophore mit Funktionalisierten," (foreign language) *ausgefuhrt am Institut fur Organische und Makromolekulare Chemie der Heinrich–Heine-Universitat Dusseldorf*, Oct. –Jun. 1994, pp. 1–73.

Gonzalez and Negulescu. Intracellular detection assays for high–throughput screening. Curr. Opin. Biotech. vol. 9 No. 6. 624–631 Dec. 1998.

Cacciatore et al., Identification of Neural Circuits by Imaging Coherent Electrical Activity with FRET–based dyes. Neuron 23 449–459 Jul. 1999.

Gonzalez et al. Cell based assays and instrumentation for screening ion–channel targets. Drug Discovery Today vol. 4, No. 9, Sep. 1999.

Gonzalez, et al., Biophysical Journal, vol. 69, pp. 1272–1280, (1950).

Gutierrez–Merino, et al., Biochemistry, vol. 34, pp. 4846–4855, (1995).

Rink, et al., Biochimica et Biophysica Acta., vol. 595, pp. 15–30, (1980).

\* cited by examiner

US 6,596,522 B2

DETECTION OF TRANSMEMBRANE POTENTIALS BY OPTICAL METHODS

This application is a continuation of U.S. Ser. No. 08/765,860, filed May 8, 1997 (now U.S. Pat. No. 6,107,066), which is a 371 application of International Application No. US96/09652, filed Jun. 6, 1996.

BACKGROUND OF THE INVENTION

The present invention relates generally to the detection and measurement of transmembrane potentials. In particular, the present invention is directed to compositions and optical methods for determining transmembrane potentials across the plasma membrane of biological cells.

This invention was made with Government support under Grant No. R01 NS27177-07, awarded by the National Institutes of Health. The Government has certain rights in this invention.

Fluorescence detection and imaging of cellular electrical activity is a technique of great importance and potential (Grinvald, A., Frostig, R. D., Lieke, E., and Hildesheim, R. 1988. Optical imaging of neuronal activity. *Physiol. Rev.* 68:1285–1366; Salzberg, B. M. 1983. Optical recording of electrical activity in neurons using molecular probes. In Current Methods in Cellular Neurobiology. J. L. Barker, editor. Wiley, New York. 139–187; Cohen, L. B. and S. Lesher. 1985. Optical monitoring of membrane potential: methods of multisite optical measurement. In Optical Methods in Cell Physiology. P. de Weer and B. M. Salzberg, editors. Wiley, New York. 71–99).

Mechanisms for optical sensing of membrane potential have traditionally been divided into two classes:

(1) sensitive but slow redistribution of permeant ions from the extracellular medium into the cell, and (2) fast but small perturbations of relatively impermeable dyes attached to one face of the plasma membrane. see, Loew, L. M., "How to choose a potentiometric membrane probe", In Spectroscopic Membrane Probes. L. M. Loew, ed., 139–151 (1988) (CRC Press, Boca Raton); Loew, L. M., "Potentiometric membrane dyes", In Fluorescent and Luminescent Probes for Biological Activity. W. T. Mason, ed., 150–160 (1993) (Academic Press, San Diego).

The permeant ions are sensitive because the ratio of their concentrations between the inside and outside of the cell can change by up to the Nernstian limit of 10-fold for a 60 mV change in transmembrane potential. However, their responses are slow because to establish new equilibria, ions must diffuse through unstirred layers in each aqueous phase and the Low-dielectric-constant interior of the plasma membrane. Moreover, such dyes distribute into all available hydrophobic binding sites indiscriminately. Therefore, selectivity between cell types is difficult. Also, any additions of hydrophobic proteins or reagents to the external solution, or changes in exposure to hydrophobic surfaces, are prone to cause artifacts. These indicators also fail to give any shift in fluorescence wavelengths or ratiometric output. Such dual-wavelength readouts are useful in avoiding artifacts due to variations in dye concentration, path length, cell number, source brightness, and detection efficiency.

By contrast, the impermeable dyes can respond very quickly because they need little or no translocation. However, they are insensitive because they sense the electric field with only a part of a unit charge moving less than the length of the molecule, which in turn is only a small fraction of the distance across the membrane. Furthermore, a significant fraction of the total dye signal comes from molecules that sit on irrelevant membranes or cells and that dilute the signal from the few correctly placed molecules.

In view of the above drawbacks, methods and compositions are needed which are sensitive to small variations in transmembrane potentials and can respond both to rapid, preferably on a millisecond timescale, and sustained membrane potential changes. Also needed are methods and compositions less susceptible to the effects of changes in external solution composition, more capable of selectively monitoring membranes of specific cell types, and providing a ratiometric fluorescence signal. This invention fulfils this and related needs.

SUMMARY OF THE INVENTION

Methods and compositions are provided for determining transmembrane electrical potential (membrane potential), particularly across the outermost (plasma) membrane of living cells. In one aspect, the method comprises:

(a) introducing a first reagent comprising a hydrophobic fluorescent ion, which is capable of redistributing from a first face of the membrane to a second face of the membrane in response to changes in the potential of the membrane, as described by the Nernst equation, (b) introducing a second reagent which labels one face, usually the extracellular face of the membrane, which second reagent comprises a chromophore, capable of undergoing energy transfer by either (i) donating excited state energy to the fluorescent ion, or (ii) accepting excited state energy from the fluorescent ion, (c) exposing the membrane to excitation light of an appropriate wavelength, typically in the ultraviolet or visible region;

(d) measuring energy transfer between the fluorescent ion and the second reagent, and (e) relating the extent of energy transfer to the membrane potential.

The second reagent is preferably a fluorophore. In each case the excited state interaction can proceed by fluorescence resonance energy transfer (FRET), which is preferred, or some other mechanism such as electron transfer, exchange (Dexter) interaction, paramagnetic quenching, or promoted intersystem crossing. The method finds particular utility in detecting changes in membrane potential of the plasma membrane in biological cells.

Preferably, the hydrophobic ion is an anion which labels the extracellular face of the plasma membrane. Upon addition of the hydrophobic fluorescent anion to the membrane, cell, or tissue preparation, the anion partitions into the plasma membrane, where it distributes between the extracellular and intracellular surfaces according to a Nernstian equilibrium. Changes in the membrane potential cause the fluorescent anion to migrate across the membrane so that it can continue to bind to whichever face (the intracellular or extracellular face) is now positively charged. Since the efficiency of energy transfer between the two reagents is a function of the distance between them and this distance varies as the fluorescent anion redistributes back and forth across the membrane, measurement of energy transfer provides a sensitive measure of changes in the transmembrane potential. For example, if the membrane potential (intracellular relative to extracellular) changes from negative to positive, the fluorescent hydrophobic anion is pulled from the extracellular surface to the intracellular surface of the plasma membrane. If the second reagent is one which is on the extracellular face, this results in an increase in the distance between the anion and the second reagent and a concomitant decrease in the efficiency of FRET and quenching between the two species. Thus, fluorescence measurements at appropriate excitation and emission wavelengths provide a fluorescent readout which is sensitive to the changes in the transmembrane potential. Typically, the time constant for the redistribution of the fluorescent anion is rapid and in the millisecond time scale thus allowing the convenient measurement both of rapid cellular electrical phenomena such as action potentials or ligand-evoked channel opening, as well as slower and more sustained changes evoked by altering the activity of ion pumps or exchangers.

Conventional electrophysiological techniques read the potential at the tip of an electrode and are thus limited to measurements of a single cell. By contrast, the optical indicators described herein are particularly advantageous for monitoring the membrane potential of many neurons or muscle cells simultaneously. Optical indicators, unlike conventional microelectrodes, do not require physical puncture of the membrane; in many cells or organelles, such puncture is highly injurious or mechanically difficult to accomplish. Optical indicators are thus suitable for cells too small or fragile to be impaled by electrodes.

In another aspect of the invention, the voltage sensing methods allow one to detect the effect of test samples, such as potential therapeutic drug molecules, on the activation/deactivation of ion transporters (channels, pumps, or exchangers) embedded in the membrane.

The compositions of the present invention comprise two reagents. The first reagent comprises a hydrophobic fluorescent ion (preferably an anion) which is capable of redistributing from one face of a membrane to the other in response to changes in transmembrane potential. This anion is referred to as the mobile or hydrophobic anion. Exemplary anions are polymethine oxonols, tetraaryl borates conjugated to fluorophores and fluorescent complexes of rare earth and transition metals. The second reagent comprises a chromophore, preferably a fluorophore, capable of undergoing energy transfer by either (i) donating excited state energy to the fluorescent anion, or (ii) accepting excited state energy from the fluorescent anion. The second reagent binds selectively to one face of the membrane, and unlike the first reagent, does not redistribute in response to transmembrane potential changes. Therefore, it is referred to as the asymmetrically bound or immobile reagent. Exemplary second reagents include fluorescent lectins, fluorescent lipids, fluorescent carbohydrates, fluorescently labelled antibodies against surface membrane constituents, and amphiphilic fluorescent dyes. In certain preferred embodiments of the invention, the first and second reagents are bound together by a suitable flexible linker group. The linker group is long enough to permit the first reagent to reside in the opposite face of the membrane from the second reagent and reduce FRET.

BRIEF DESCRIPTION OF THE DRAWINGS

The invention may be better understood with reference to the accompanying drawings, in which.

DESCRIPTION OF THE PREFERRED EMBODIMENT

Figure 1A:
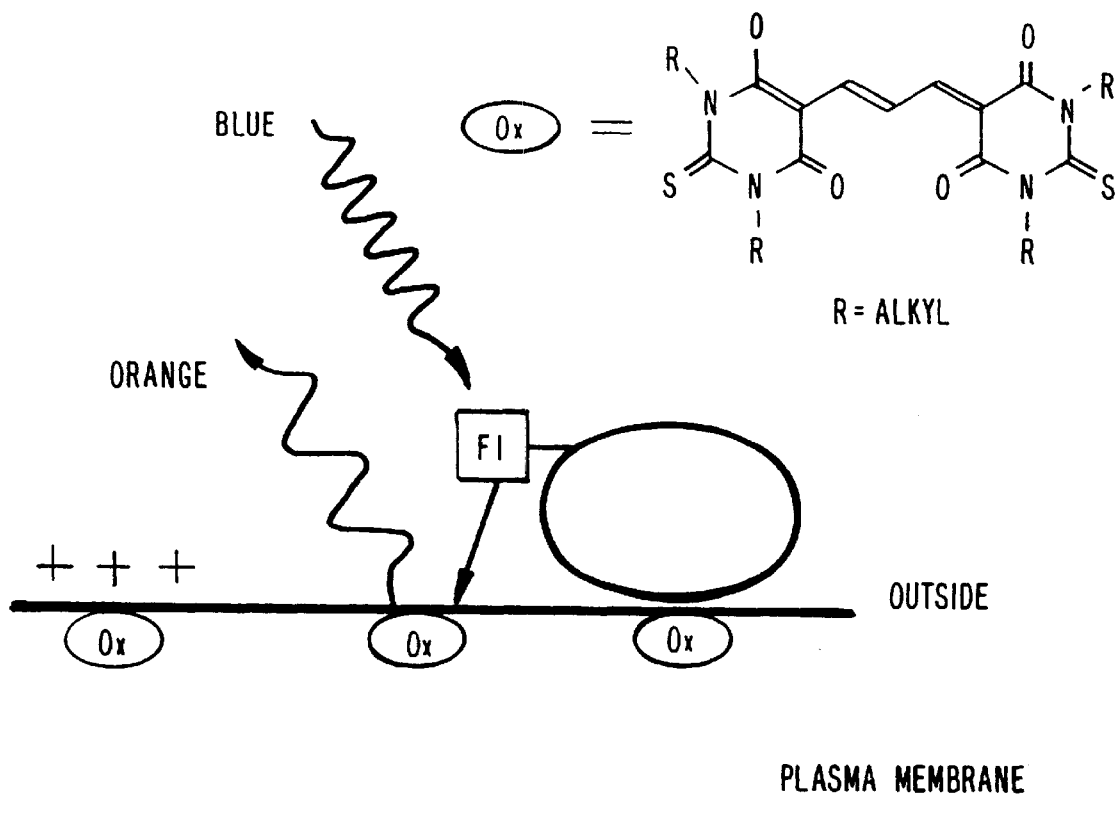
FIGS. 1A and 1B illustrate a scheme of the voltage-sensitive FRET mechanism.

The following definitions are set forth to illustrate and define the meaning and scope of the various terms used to describe the invention herein.

The term "hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "alkyl" refers to a branched or straight chain acyclic, monovalent saturated hydrocarbon radical of one to twenty carbon atoms.

The term "alkenyl" refers to an unsaturated hydrocarbon radical which contains at least one carbon—carbon double bond and includes straight chain, branched chain and cyclic radicals.

The term "alkynyl" refers to an unsaturated hydrocarbon radical which contains at least one carbon—carbon triple bond and includes straight chain, branched chain and cyclic radicals.

The term "lower" referred to herein in connection with organic radicals or compounds respectively defines such with up to and including six, preferably up to and including four carbon atoms. Such groups may be straight chain or branched.

The term "heteroalkyl" refers to a branched or straight chain acyclic, monovalent saturated radical of two to forty atoms in the chain in which at least one of the atoms in the chain is a heteroatom, such as, for example, oxygen or sulfur.

The term "lower-alkyl" refers to an alkyl radical of one to six carbon atoms. This term is further exemplified by such radicals as methyl, ethyl, n-propyl, isopropyl, isobutyl, sec-butyl, n-butyl and tert-butyl, n-hexyl and 3-methylpentyl.

The term "cycloalkyl" refers to a monovalent saturated carbocyclic radical of three to twelve carbon atoms in the carbocycle.

The term "heterocycloalkyl" refers to a monovalent saturated cyclic radical of one to twelve atoms in the ring, having at least one heteroatom, such as oxygen or sulfur) within the ring.

The term "alkylene" refers to a fully saturated, cyclic or acyclic, divalent, branched or straight chain hydrocarbon radical of one to forty carbon atoms. This term is further exemplified by radicals such as methylene, ethylene, n-propylene, 1-ethylethylene, and n-heptylene.

The term "heteroalkylene" refers to an alkylene radical in which at least one of the atoms in the chain is a heteroatom.

The term "heterocyclo-diyl" refers to a divalent radical containing a heterocyclic ring. The free valences may both be on the heterocyclic ring or one or both may be on alkylene substituents appended onto the ring.

The term "lower-alkylene" refers to a fully saturated, acyclic, divalent, branched or straight chain hydrocarbon radical of one to six carbon atoms. This term is further exemplified by such radicals as methylene, ethylene, n-propylene, 1-propylene, n-butylene, 1-butylene (or 2-methylpropylene), isoamylene (or 3,3 dimethylpropylene), pentylene, and n-hexylene.

The term "cycloalkyl lower-alkyl" refers to a cycloalkyl group appended to a lower-alkyl radical. This term is exemplified by, but not limited to, groups such as cyclopropylmethyl, cyclopentylmethyl, cyclopentylethyl, and cyclopentylpropyl.

The term "substituted phenyl" refers to a phenyl group which is mono-, di-, tri-, or tetra-substituted, independently, with hydrocarbyl, alkyl, lower-alkyl, cycloalkyl or cycloalkyl-lower alkyl.

The term "aryl" refers to an aromatic monovalent carbocyclic radical having a single ring (e.g., phenyl) or multiple condensed rings (e.g., naphthyl, anthracenyl), which can optionally be mono-, di-, or tri-substituted, independently, with hydrocarbyl, alkyl, lower-alkyl, cycloalkyl or cycloalkyl lower alkyl.

The term "arylene" refers to an aromatic divalent carbocyclic radical. The open valence positions may be at any position on the ring(s). In the case of a divalent phenyl radical, they may be ortho, meta or para to each other.

The term "aralkyl" refers to an aryl group appended to a lower-alkyl radical. This term is exemplified by, but not limited to, groups such as benzyl, 2-phenylethyl and 2-(2-naphthylethyl).

The term "aralkenyl" refers to an aryl group appended to a fully conjugated alkenyl radical. This term is exemplified by styrenyl (cis and trans) and 1-phenyl butadienyl and 1-naphthyl butadienyl (including all possible combinations of the Z and E isomers about the double bonds).

The term "halo" refers to fluoro, bromo, chloro and iodo.

The term "lower-alkylthio" refers to the group R—S—, where R is lower-alkyl.

The term "leaving group" means a group capable of being displaced by a nucleophile in a chemical reaction, for example halo, alkyl sulfonates (e.g., methanesulfonate), aryl sulfonates, phosphates, sulfonic acid, sulfonic acid salts, imidazolides, N-hydroxy succinimides and the like.

The term "linker" refers to any chemically and biologically compatible covalent grouping of atoms which can serve to link together the first and second reagents of this invention. Generally, preferred linkers have from 20 to 40 bonds from end to end, preferably 25 to 30 bonds, and may be branched or straight chain or contain rings. The bonds may be carbon—carbon or carbon-heteroatom or heteroatom—heteroatom bonds. The linkage can be designed to be hydrophobic or hydrophilic. The linking group can contain single and/or double bonds, 0–10 heteroatoms (O, S preferred), and saturated or aromatic rings. The linking group may contain groupings such as ester, ether, sulfide, disulfide and the like.

The term "amphiphilic" refers to a molecule having both a hydrophilic and a hydrophobic portion.

Methods and compositions are provided for detecting changes in membrane potential biological systems. One aspect of the detection method comprises:

(a) introducing a first reagent comprising a hydrophobic fluorescent anion capable of redistributing from a first face of the membrane to a second face of the membrane in response to changes in the potential of the membrane, (b) introducing a second reagent which labels the first face or the second face of the membrane, which second reagent comprises a fluorophore capable of undergoing energy transfer by either (i) donating excited state energy to the fluorescent anion, or (ii) accepting excited state energy from the fluorescent anion, (c) exposing the membrane to excitation light of appropriate wavelengths;

(d) measuring energy transfer between the fluorescent anion and the second reagent, and (e) relating the energy transfer to the change in plasma membrane potential.

The preferred mode of energy transfer is fluorescence resonance energy transfer (FRET). The method finds particular utility in detecting changes in membrane potential of the plasma membrane in biological cells.

The compositions used in the methods of the invention comprise two reagents. The first reagent comprises a hydrophobic fluorescent anion which rapidly redistributes from one face of the. plasma membrane to the other in response to changes in transmembrane potential. This species is referred to as the mobile or hydrophobic anion. The second reagent comprises a fluorophore capable of undergoing energy transfer by either (i) donating excited state energy to the fluorescent anion, or (ii) accepting excited state energy from the fluorescent anion, typically by FRET.

The first and second reagents are spectroscopically complementary to each other, by which is meant that their spectral characteristics are such that excited state energy transfer can occur between them. Either reagent can function as the donor or the acceptor, in which case the other reagent is the corresponding complement, i.e., the acceptor or donor respectively. Both FRET and quenching are highly sensitive to the distance between the two species. For example, the nonradiative Forster-type quenching observed in FRET varies inversely with the sixth power of the distance between the donor and acceptor species. Therefore, when the membrane potential changes and the hydrophobic fluorescent anion moves either further away from or closer to the second reagent, FRET between the two reagents is either reduced or enhanced significantly. Other mechanisms such as electron-transfer, Dexter exchange interaction, paramagnetic quenching, and promoted intersystem crossing are even shorter-range and require the two reagents to collide or at least come within 1 nm of each other.

Previously reported voltage-sensitive fluorescent indicators operating by potential-driven redistribution of the fluorophore across the membrane had response times of >100 ms, a often as long as minutes. One aspect of the present invention provides highly fluorescent anionic dyes which translocate across the membrane at much faster rates, with exponential time constants typically less than about 10 ms, frequently less than 5 ms, most frequently from about 1 to 3 ms and most preferably less than 1 ms time scale (e.g., 0.1 to 1 ms). These translocation rates are independent of the presence of the second reagent on the extracellular surface of the membrane. Response times of <1 ms are necessary for accurate measurement of single action potentials in individual neurons and are obtained with some of the dyes described herein (e.g., hexyl-substituted pentamethineoxonol, diSBA-$C_6$-(5)). Other dyes described herein have response times in the 2–5 ms range, which are fast enough to monitor voltage changes in heart and smooth muscle, many synaptic potentials in single neurons, and the average firing activity in populations of neurons (for example, mapping the electrical responses of different regions of the central nervous system to sensory inputs). The indicators of the present invention are also able to follow slower voltage changes over a time scale of seconds to minutes.

I. First Reagent—Hydrophobic Fluorescent Anions

In the compositions and methods of the present invention, the first reagent comprises a hydrophobic ion (fluorescence donor, acceptor, or quencher) which serves as a voltage sensor and moves within the membrane from one face of the membrane to another in response to changes in the transmembrane potential. The distribution of hydrophobic ions between the two membrane-aqueous interfaces (the extracellular interface and the intracellular interface) is determined by the membrane potential. Cations will tend to congregate at the negatively charged membrane interface and correspondingly, anions will move to the positively charged interface. The inherent sensitivity of the invention is based on the large interfacial concentration changes of the mobile ion at physiologically relevant changes in membrane potentials. Potentially, a 60 mV change produces 10-fold change in the ratio of the anion concentrations at the respective interfaces. The methods of this invention couple this change in interfacial concentration to an efficient fluorescent readout thus providing a sensitive method of detecting changes in transmembrane potential. The speed of the fluorescence change is dependent on the membrane translocation rate of the hydrophobic ion.

Preferably, the fluorescent ions which translocate across the plasma membrane are hydrophobic in order to bind strongly to the plasma membrane and translocate rapidly across it in response to changes in transmembrane potential. Preferably, the ion will have a single charge which will be delocalized across a significant portion of the dye, preferably the entire dye. Delocalization of the charge reduces the Born charging energy (inversely proportional to anion radius) required to move a charged molecule from a hydrophilic to a hydrophobic environment and facilitates rapid translocation of ions (Benz, R. 1988. "Structural requirement for the rapid movement of charged molecules across membranes", *Biophys. J.* 54:25–33). Increasing hydrophobicity minimizes release of the bound dye from the plasma membrane and buries the ion deeper into the membrane, which decreases the electrostatic activation energy for translocation. Polar groups on the ion should be kept to a minimum and shielded as much as possible to disfavor solvation in the headgroup region of the bilayer. However, hydrophobicity cannot be increased without limit, because some aqueous solubility is required to permit cellular loading. If necessary, dyes may be loaded with the aid of amphiphilic solubilizing reagents such as beta-cyclodextrin, Pluronics such as Pluronic F-127, or polyethylene glycols such as PEG400, which help solubilize the hydrophobic ions in aqueous solution.

The term "hydrophobic" when used in the context of the hydrophobic ion refers to a species whose partition coefficient between a physiological saline solution (e.g. HBSS) and octanol is preferably at least about 50, and more preferably at least about 1000. Its adsorption coefficient to a phospholipid bilayer (such as for example a membrane derived from a human red blood cell is at least about 100 nm, preferably at least about 300 nm (where the membrane is 3 nm). Methods of determining partition coefficients and adsorption coefficients are known to those of skill in the art.

It is generally preferred that the hydrophobic dye be an anionic species. Ester groups of biological membranes generate a sizable dipole potential within the hydrocarbon core of the membrane. This potential aids anion translocation through the hydrophobic layer but hinders cations. Therefore, where membrane translocation is concerned, anions have a tremendous inherent speed advantage over cations. For example, it is known that for the isostructural ions tetraphenylphosphonium cation and tetraphenylborate anion, the anion is much more permeable than the cation (Flewelling, R. F. and Hubbell, W. L. 1986. "The membrane dipole potential in a total membrane potential model", *Biophys. J.* 49:541–552).

Preferably, the anions should be strongly fluorescent when adsorbed to the membrane, whereas they should have minimal fluorescence when free in aqueous solution. Preferably, the anionic fluorophores should be at least four times, and more preferably at least about eight times, brighter when adsorbed to the membrane. In the case of the thiobarbiturate oxonols described herein, their fluorescence is about 20 fold greater in the membrane than in water. In principle, if the dye bound extremely tightly to the membrane one would not need a high ratio of fluorescence when bound to the membrane to that when free in aqueous solution; however, because in reality the volume of the membrane is tiny relative to the aqueous solution and some water solubility is necessary for loading of the dye into cells and tissue, it is desirable for the first reagent to be at least about four times more strongly fluorescent in a membrane than in aqueous solution.

The anions also should not act as ionophores, especially protonophores, since such behavior may generate sustained leakage currents. Therefore, the protonation pKa of the anion is typically well below 7, preferably below 5, more preferably below 3. Red to infra-red wavelengths of excitation and emission are preferred to avoid tissue scattering and heme absorbances. Photodynamic damage should be kept as low as possible, probably best by minimizing triplet state formation and the resulting generation of singlet oxygen.

The fluorescent hydrophobic ions include polymethine oxonols, tetraaryl borates conjugated to fluorophores and fluorescent complexes of rare earth and transition metals.

A. Polymethine Oxonols

The term "polymethine oxonol" refers to molecules comprising two potentially acidic groups linked via a polymethine chain and possessing a single negative charge delocalized between the two acidic groups. The preferred acidic groups are barbiturates or thiobarbiturates. They may be symmetric or asymmetric, i.e., each of the two (thio) barbiturates may be the same or different. The symmetric (thio)barbiturate oxonols are described by the conventional shorthand DiBA-$C_n$-(x) and DiSBA-$C_n$-(x), where DiBA refers to the presence of two barbiturates, DiSBA refers to the presence of two thiobarbiturates, $C_n$ represents alkyl substituents having n carbon atoms on the nitrogen atoms of the (thio)barbiturates, and x denotes the number of carbon atoms in the polymethine chain linking the (thio) barbiturates. It has been unexpectedly found that oxonols with long chain alkyl substituents (e.g. $C_n$ greater than hexyl, especially decyl in the pentamethine oxonols) translocate surprisingly rapidly across plasma membranes.

An extremely useful property of these oxonols is that their fluorescence emission maximum at 560 nm is 20 times brighter when bound to membranes than in aqueous solution [Rink, T. J., Montecucco, C., Hesketh, T. R., and Tsien, R. Y. 1980. Lymphocyte membrane potential assessed with fluorescent probes. *Biochim. Biophys. Acta* 595:15–30]. Furthermore, the negative charge is delocalized throughout the chromophore with the four equivalent oxygens containing the majority of the charge. The high electron affinity of the thiobarbiturate moieties discourages protonation, pKa<1, and resists photooxidative bleaching. The four N-alkyl groups and the thiocarbonyl give the molecule a necessary amount of hydrophobicity needed for tight membrane binding and rapid translocation.

Oxonol compounds used in this invention have a general structure of Formula I.

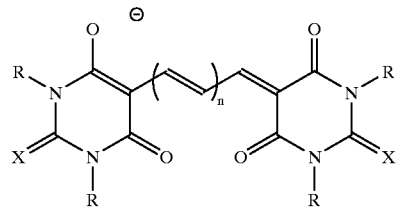

Formula I wherein:
R is independently selected from the group consisting of H, hydrocarbyl and heteroalkyl;
X is independently oxygen or sulfur; and
n is an integer from 1 to 3;
and salts thereof.

The oxonol anions are usually loaded as salts with the cation typically being $H^+$, alkali metal, substituted ammonium, or pyridinium.

Preferably X is sulfur, i.e., the hydrophobic anion is a bis-(1,3-dialkyl-2-thiobarbiturate)-polymethine oxonol or a derivative thereof.

When R is a hydrocarbyl group, it can be independently selected from the group consisting of alkyl, aryl, aralkyl, cycloalkyl and cycloalkyl lower-alkyl. Typically these groups have from about 4 to about 40 carbon atoms, more preferably, about 5 to about 20 carbon atoms. Aryl groups can be substituted with hydrocarbyl, alkyl, lower alkyl, heteroalkyl and halogen groups. Oxonols in which the R groups on a particular (thio)barbiturate moiety are different to each other are specifically contemplated by this invention and can be prepared from unsymmetrical urea derivatives.

In some embodiments, R is a hydrocarbyl group of the formula:

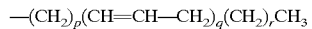

wherein:
p is an integer from 1 to about 20 (preferably about 1 to 2);
q is an integer from 1 to about 6, preferably 1 to 2;
the stereochemistry of the double bond(s) may be cis or trans, cis being preferred;
r is an integer from 1 to about 20 (preferably about 1 to 3), and p+3q+r+140, preferably from about 4 to 20, more preferably about 6 to 10.

In another embodiment of the polymethine oxonols, R is a heteroalkyl group of the formula:

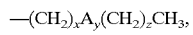

wherein:
A is oxygen or sulfur;
x is independently an integer from 1 to about 20 (preferably about from about 10 to 15);
y is independently 0 or 1;
z is independently an integer from 1 to about 20 (preferably about 10 to 15); and
x+y+z40, preferably x+y+z=an integer from about 5 to 25, more preferably about 5 to 10.

In other embodiments, R is a phenyl group independently substituted with up to four substituents selected from the group consisting of hydrocarbyl, heteroalkyl, halogen and H.

In other embodiments, one of the four R groups incorporates a linker to the second reagent, as described below in section III.

An oxonol's negative charge is distributed over the entire the chromophore. Bis(thiobarbiturate)trimethineoxonols absorb at 542 nm (ext. coefficient=200,000 $M^{-1}$ $cm^{-1}$), emit at 560 nm and have a quantum yield of 0.4 in octanol. An oxonol where R=n-hexyl, DiSBA-$C_6$-(3), translocates with a time constant ($\tau$) <3 ms in voltage clamped mammalian cells. The corresponding decyl compound, DiSBA-$C_{10}$-(3), translocates with a time constant <2 ms. The molecular requirement for rapid translocation is nicely met with the symmetric oxonols. Bis(thiobarbiturate) pentamethineoxonols absorb at ~630 nm and emit at ~660 nm. The negative charge is further delocalized in such red-shifted oxonols. As expected, the translocation rates for the pentamethine oxonols are faster than for the trimethine oxonols. DiSBA-$C_4$-(5) crosses the membrane with $\tau$<3 ms, six times faster than the corresponding trimethine oxonol. DiSBA-$C_6$-(5) translocates with $\tau$~0.4 ms at 20.

B. Tetraaryl Borate—Fluorophore Conjugates

Another useful class of fluorescent hydrophobic anions are tetraaryl borates having a general structure of Formula II.

$$[(Ar^1)_3B—Ar^2—Y—FLU]^- \quad \text{Formula II}$$

wherein:
Ar$^1$ is an aryl group;
Ar$^2$ is a bifunctional arylene group;
B is boron;
Y is oxygen or sulfur; and
FLU is a neutral fluorophore.

Frequently Ar$^1$ is substituted with one or two electron withdrawing groups, such as but not limited to $CF_3$. In selected embodiments, Ar$^1$ and Ar$^2$ are optionally substituted phenyl groups as shown below for the structure of Formula III.

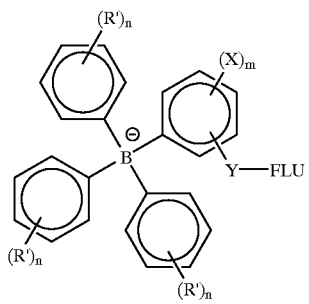

Formula III wherein:
each R' is independently H, hydrocarbyl, halogen, $CF_3$ or a linker group;
n is an integer from 0 to 5;
each X is independently H, halogen or $CF_3$;
m is an integer from 0 to 4;
Y is oxygen or sulfur; and
FLU is a neutral fluorophore.

When R' is hydrocarbyl, it is typically from 1 to about 40 carbon atoms, preferably 3 to about 20 carbon atoms, more preferably about 5 to 15 carbon atoms. Preferably, R' is a lower alkyl group, more preferably (for ease of synthesis) all the R's are H. When R' is not hydrocarbyl, it is frequently $CF_3$ and n=1. In selected embodiments X=F and m=4. X is typically electron-withdrawing to prevent photoinduced electron transfer from the tetraaryl borate to the fluorophore, which quenches the latter. X=F is most preferred.

1. Synthesis of Tetraaryl Borate—Fluorophore Conjugates

Figure 10:
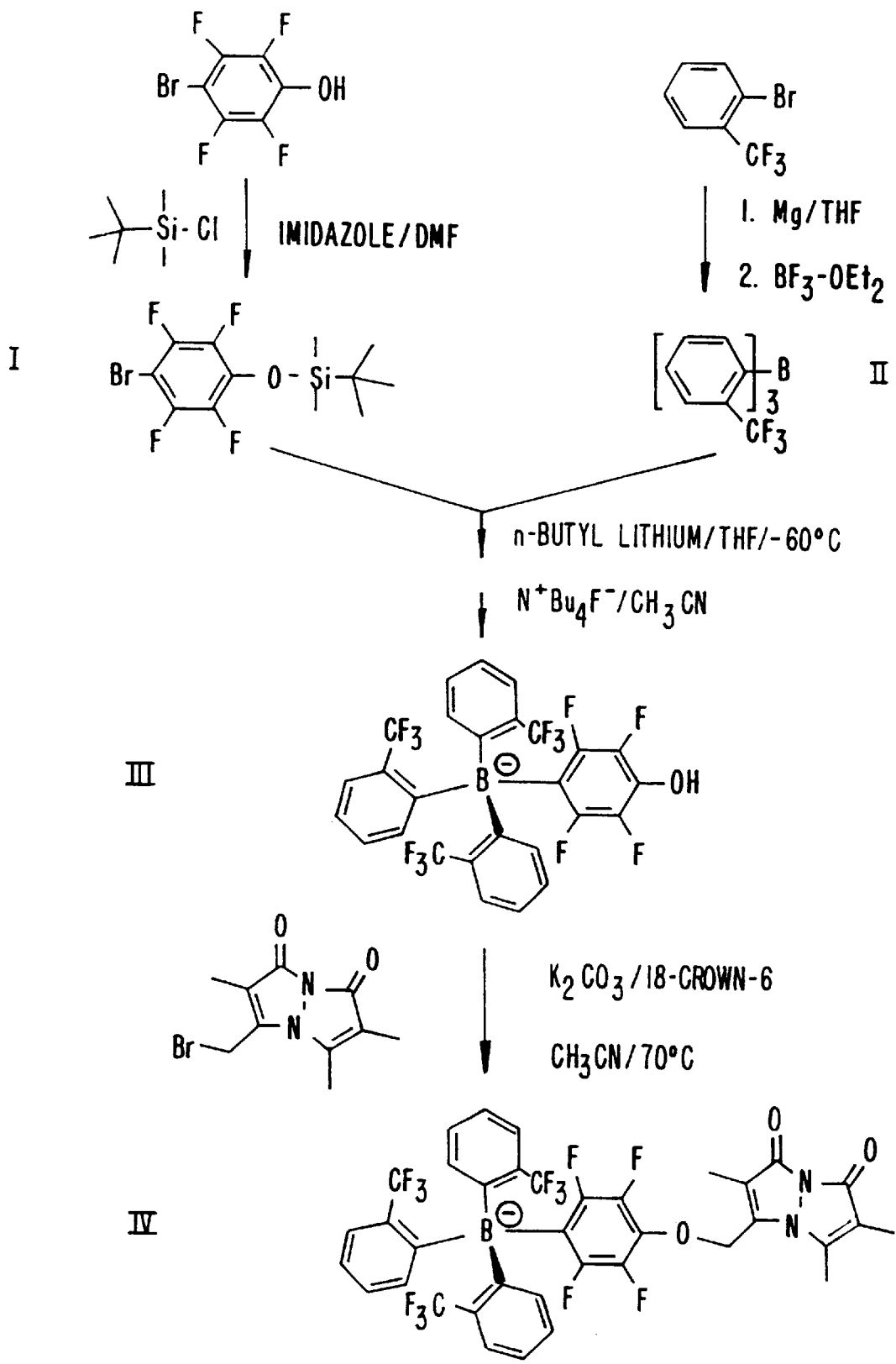
FIG. 10 shows the synthesis of a fluorescent tetraaryl borate.

A general synthesis of fluorescent tetraaryl borate anions has been developed and is shown in FIG. 10 for an exemplary fluorescent bimane tetraaryl borate conjugate (identified as Bormane, compound IV in FIG. 10).

In general terms, a triaryl borane is reacted with a protected phenoxy or thiophenoxy organometallic reagent, such as, for example, an organolithium derivative. The protecting group is subsequently removed and the unmasked phenol (or thiophenol) is reacted with a fluorophore bearing a leaving group. Nucleophilic displacement of the leaving group followed by conventional purification of the crude reaction product furnishes the tetraaryl borate anion conjugated to the fluorophore. Substituents R' and X are varied by appropriate choice of the starting triaryl borane and the phenoxy (or thiophenoxy) organometallic. Suitable starting materials can be obtained from Aldrich Chemical Co. (Milwaukee, Wis.) and other commercial suppliers known to those of skill in the art. Thus in these species, a fluorophore is conjugated to a functionalized borate core. This general synthetic method allows one to attach any fluorophore to the borate anion.

2. Neutral Fluorophores

As polar chromophores retard the membrane translocation rate, it is preferred that the fluorophore conjugated to the tetraaryl borate be a neutral species. For purposes of the present invention, a neutral fluorophore may be defined as a fluorescent molecule which does not contain charged functional groups. Representative fluorescent molecules bearing leaving groups and suitable for conjugation are available from Molecular Probes (Portland, Oreg.), Eastman Kodak (Huntington, Tenn.), Pierce Chemical Co. (Rockville, Md.) and other commercial suppliers known to those of skill in the art. Alternatively, leaving groups can be introduced into fluorescent molecules using methods known to those of skill in the art.

Particularly suitable classes of neutral fluorophores which can be conjugated to the tetraaryl borates for use in accordance with the present invention include, but rare not limited to, the following: bimanes; bodipys; and coumarins.

Bodipys (i.e., difluoroboradiazaindacenes) may be represented by a general structure of Formula IV.

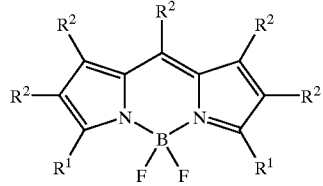

Formula IV wherein:
each R$^1$, which may be the same or different, is independently selected from the group consisting of H, lower alkyl, aryl, heteroaromatic, aralkenyl and an alkylene attachment point;
each R$^2$, which may be the same or different, is independently selected from the group consisting of H, lower alkyl, phenyl and an alkylene attachment point.

For the purposes of this disclosure, the term "alkylene attachment point" refers to the group —$(CH_2)_t$— or —(CH$_2$)$_t$—C(O)— wherein, t is an integer from 1 to 10, and one valence bond is attached to the fluorophore and the other valence bond is attached to the tetraaryl borate. Preferably, t=1, i.e. the alkylene attachment point is a methylene group. As will be apparent to one of skill in the art, all fluorophores will possess one attachment point at which they will be conjugated to the tetraaryl borate. Generally, the precursor molecule used to conjugate the fluorophore to the tetraaryl borate will carry a leaving group at the attachment point. Reaction of this precursor with an appropriate nucleophile on the tetraaryl borate (e.g., an amine, hydroxy or thiol), will provide a fluorophore-tetraaryl borate conjugate linked together at the attachment point. The term "attachment point" refers more broadly to a chemical grouping which is appropriate to react with either a fluorophore or a bifunctional linker to form the fluorescent conjugates and/or linked first and second reagents as disclosed herein. Frequently, these attachment points will carry leaving groups, e.g., alkyl tosylates, activated esters (anhydrides, N-hydroxysuccinimidyl esters and the like) which can react with a nucleophile on the species to be conjugated. One of skill will recognize that the relative positioning of leaving group and the nucleophile on the molecules being linked to each other can be reversed.

Coumarins and related fluorophores may be represented by structures of general Formulas V and VI

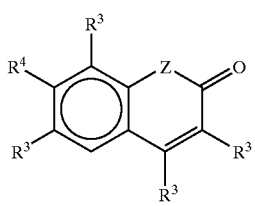

Formula V

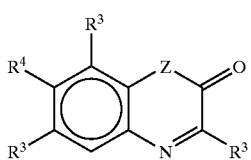

Formula VI wherein:
  each R$^3$, which may be the same or different, is independently selected from the group consisting of H, halogen, lower alkyl, CN, CF$_3$, COOR$^5$, CON(R$^5$) OR$^5$, and an attachment point;
  R$_4$ is selected from the group consisting of OR$^5$ and N(R$^5$)$_2$;
  Z is O, S or NR$^5$; and
  each R$^5$, which may be the same or different, is independently selected from the group consisting of H, lower alkyl and an alkylene attachment point.

Bimanes may be represented by a structure of general Formula VII.

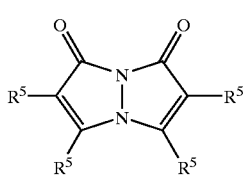

Formula VII wherein:

each R$^5$, which may be the same or different, is independently H, lower alkyl or an alkylene attachment point.

Fluorescent tetraaryl borates with coumarins and bimanes attached have been prepared. These fluorescent borates translocate with τ<3 ms in voltage clamped fibroblasts. Synthesis of an exemplary fluorescent tetraryl borate is described in Example V.

C. Fluorophore Complexes with Transition Metals

Lanthanide ions, such as, for example, Tb$^{3+}$ and Eu$^{3+}$, luminesce in the green and red regions of the visible spectrum with millisecond lifetimes. The emission is composed of several sharp bands that are indicative of the atomic origin of the excited states. Direct excitation of the ions can be accomplished using deep UV light. Excitation of the lanthanide ions at longer wavelengths is possible when the ions are chelated by absorbing ligands that can transfer excitation energy to the ions, which then can luminesce with their characteristic emission as if they had been excited directly. Lanthanide complexes of Tb$^{3+}$ and Eu3+ with absorbing ligands that contribute 4 negative charges, resulting a net charge of −1, may function as mobile ions for the voltage-sensitive FRET mechanism. The lifetimes of Tb$^{3+}$ and Eu$^{3+}$ are still sufficiently fast to measure millisecond voltage changes.

This invention also provides such complexes which can function the fluorescent hydrophobic anion (as FRET donors) in the first reagent. Using the ligand bis-(salicylaldehyde)ethylenediamine (Salen)$^{2-}$, [Tb(Salen)$_2$]$^{-1}$ and [Eu(Salen)$_2$]$^{-1}$ have been made. These complexes absorb maximally at 350 nm with significant absorbance up to 380 nm and luminesce with the characteristic atomic emission, FIG. 10. The use of lanthanide complexes as donors offers several unique advantages. Scattering, cellular autofluorescence, and emission from directly excited acceptors have nanosecond or shorter lifetimes and may be rejected by time gating of the emission acquisition (See for example Marriott, G., Heidecker, M., Diamandis, E. P., Yan-Marriott, Y. 1994. Time-resolved delayed luminescence image microscopy using an europium ion chelate complex. *Biophys. J.* 67: 957–965). The elimination of the fast emission reduces the background and gives excellent signal to noise ratios. Another major advantage of using lanthanide chelates as donors is that the range of FRET is amplified by lateral diffusion in the membrane during the excited state lifetime (Thomas, D. D., Carlsen, W. F., Stryer, L. 1978. Fluorescence energy transfer in the rapid diffusion limit. *Proc. Natl. Acad. Sci. USA* 75: 5746–5750). This feature greatly reduces the need for high concentrations of acceptors to ensure efficient FRET. In addition to reducing the perturbation and stress to the cellular system from high dye concentrations, the diffusion enhanced FRET will lead to greater voltage sensitivity than is possible in a static case. Lanthanide chelates can also be used as asymmetrically labeled donors to mobile acceptors such as the tri and pentamethine oxonols, with the same advantages as discussed above.

Representative lanthanide complexes which may be used as a hydrophobic fluorescent anion are shown in Formulas XI and XII

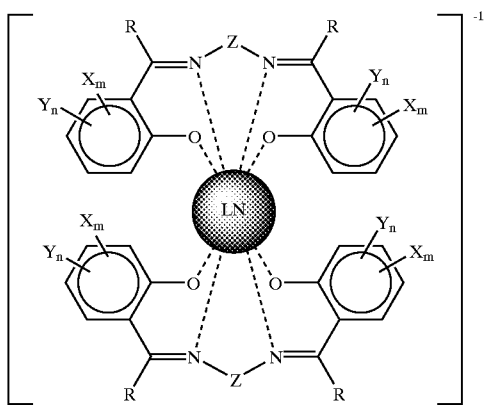

Formula XI wherein:
Ln=Tb, Eu, or Sm;
R is independently H, C1–C8 alkyl, C1–C8 cycloalkyl or C1–C4 perfluoroalkyl;
X and Y are independently H, F, Cl, Br, I, $NO_2$, $CF_3$, lower (C1–C4) alkyl, CN, Ph, O-(lower alkyl), or OPh; or X and Y together are —CH=CH—; and
Z=1,2-ethanediyl, 1,3-propanediyl, 2,3-butanediyl, 1,2-cyclcohexanediyl, 1,2-cyclopentanediyl, 1,2-cycloheptanediyl, 1,2-phenylenediyl, 3-oxa-1,5-pentanediyl, 3-aza-3-(lower alkyl)-1,5-pentanediyl, pyridine-2,6-bis(methylene) or tetrahydrofuran-2,5-bis(methylene).

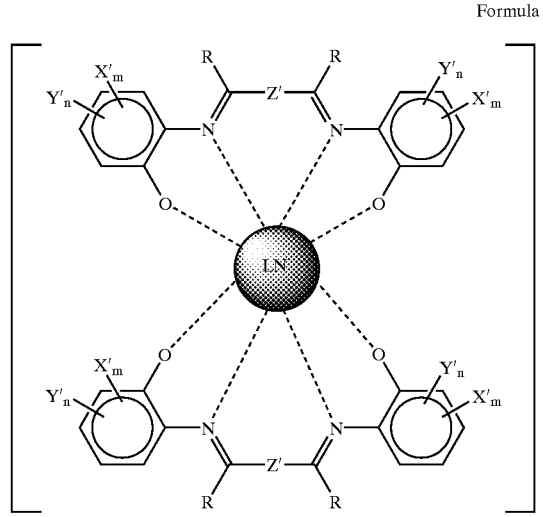

Formula XII wherein:
Ln=Tb, Eu, or Sm;
R is independently H, C1–C8 alkyl, C1–C8 cycloalkyl or C1–C4 perfluoroalkyl;
X' and Y' are independently H, F, Cl, Br, I, $NO_2$, $CF_3$, lower (C1–C4) alkyl, CN, Ph, O-(lower alkyl), or OPh; or X' and Y' together are —CH=CH—; and
Z' is independently a valence bond, $CR_2$, pyridine-2-6-diyl or, tetrahydrofuran-2,5-diyl.

II. Immobile, Asymmetrically Bound Second Reagents

The second reagent is a fluorescent donor, acceptor, or quencher, complementary to the first reagent, the hydrophobic anion, and binds either to the extracellular or intracellular face of the plasma membrane. Thus, the presence of the second reagent on one or the other face of the membrane desymmetrizes the membrane. As described earlier, irradiation with light of an appropriate wavelength generates a fluorescent readout which changes in response to movement of the hydrophobic ion back and forth across the plasma membrane. As would be immediately apparent to those skilled in the field, there are numerous molecular species which could function as the fluorescently active desymmetrizing agent. The primary characteristics for this component are that it locate on one face of the plasma membrane and function in a complementary manner (i.e., as a fluorescent donor, acceptor, or quencher) to the hydrophobic ion which shuttles back forth across the membrane as the transmembrane potential changes. Exemplary second reagents include fluorescent lectins, fluorescent lipids, fluorescent carbohydrates with hydrophobic substituents, fluorescent peptides, fluorescently labelled antibodies against surface membrane constituents, or xanthenes, cyanines and coumarins with hydrophobic and hydrophilic substituents to promote binding to membranes and to prevent permeation through membranes.

A. Fluorescent Lectins

One class of second reagents are lectins carrying a fluorescent label. For purposes of the present invention, a lectin may be defined as a sugar binding protein which binds to glycoproteins and glycolipids on the extracellular face of the plasma membrane. See, Roth, J., "The Lectins: Molecular Probes in Cell Biology and Membrane Research," *Exp. Patholo.*

(*Supp.* 3), (Gustav Fischer Verlag, Jena, 1978). Lectins include Concavalin A; various agglutinins (pea agglutinin, peanut agglutinin, wheat germ agglutinin, and the like); Ricin, A chain and the like. A variety of lectins are available from Sigma Chemical Co., St. Louis, Mo.

Suitable fluorescent labels for use in fluorescent lectins include, but are not limited to, the following: xanthenes (including fluoresceins, rhodamines and rhodols); bodipys, cyanines, and luminescent transition metal complexes. It will be recognized that the fluorescent labels described below can be used not merely with lectins but with the other second reagents described herein. To date, the best results with lectins have been obtained with fluorescein labeled wheat germ agglutinin (FL-WGA).

1. Xanthenes

One preferred class of fluorescent labels comprise xanthene chromophores having a structure of general Formula VIII or IX.

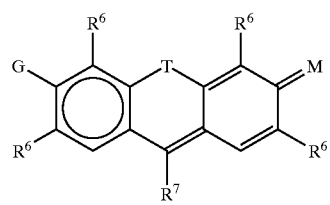

Formula VIII or

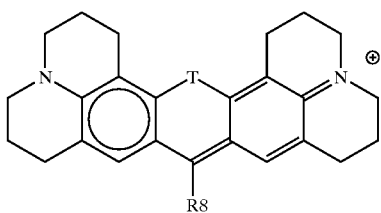

Formula IX wherein:
R⁶ is independently selected from the group consisting of H, halogen, lower alkyl, SO₃H and an alkylene attachment point;
R⁷ is selected from the group consisting of H, lower alkyl, an alkylene attachment point, and R⁸, wherein R⁸ is selected from the group consisting of

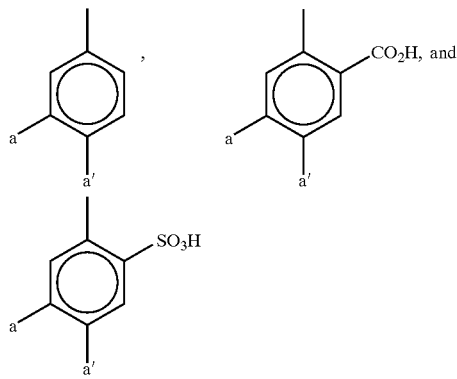

wherein:
each a and a' is independently selected from the group consisting of H and an alkylene attachment point;
G is selected from the group consisting of H, OH, OR⁹, NR⁹R⁹ and an alkylene attachment point;
T is selected from the group consisting of O, S, C(CH₃)₂ and NR⁹; and
M is selected from the group consisting of 0 and NR⁹R⁹;
wherein each R⁹, which may be the same or different, is independently H or hydrocarbyl.

2. Cyanines

Another preferred class of fluorescent labels are cyanine dyes having a structure of general Formula X.

Formula X

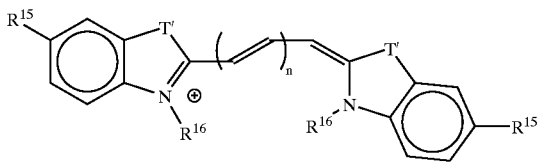

wherein:
R¹⁵ is independently selected from the group consisting of H, halogen, lower alkyl, SO₃H, PO₃H₂, OPO₃H₂, COOH, and an alkylene attachment point;
R¹⁶ is selected from the group consisting of H, lower alkyl, (CH₂)ⱼCOOH, (CH₂)ⱼSO₃H, and an alkylene attachment point; where j is an integer from 1 to 10;
T is selected from the group consisting of O, S, C(CH₃)₂, —CH=CH—, and NR¹⁷, where R¹⁷ is H or hydrocarbyl; and
n is an integer from 1 to 6.

B. Fluorescent Lipids

Fluorescently labeled amphipathic lipids, in particular phospholipids, have also been successfully employed. For purposes of the present invention, an amphipathic lipid may be defined as a molecule with both hydrophobic and hydrophilic groups that bind to but do not readily cross the cell membrane. Fluorescently labelled phospholipids are of particular value as second reagent.

As defined herein, "phospholipids" include phosphatidic acid (PA), and phosphatidyl glycerols (PG), phosphatidylcholines (PC), phosphatidylethanolamines (PE), phospatidylinositols (PI), phosphatidylserines (PS), and phosphatidyl-choline, serine, inositol, ethanolamine lipid derivatives such as egg phosphatidylcholine (EPC), dilauroylphosphatidylethanolamine, dimyristoylphosphatidylethanolamine, dipalmitoylphosphatidylethanolamine, distearoylphosphatidylethanolamine, ethanolamine, dioleoylphosphatidylethanolamine, distearoylphosphatidlylserine, dilinoleoyl phosphatidylinositol, and mixtures thereof. They may be unsaturated lipids and may be naturally occurring or synthetic. The individual phosphatidic acid components may be symmtrical, i.e. both acyl residues are the same, or they may be unsymmetrical, i.e., the acyl residues may be different.

Particularly preferred embodiments include 6-chloro-7-hydroxycoumarin-labeled phosphatidylethanolamine (Cou-PE), fluoresce:in-labeled phosphatidylethanolamine (FL-PE), N-(7-nitrobenz—2-oxa-1,3-diazol-4-yl) phosphatidylethanolamine (NBD-PE), and 5,5'-disulfoindodicarbocyanine-labeled phosphatidylethanolamine (Cy5-PE). The fluorescent group is suitably selected from those previously described as useful in preparing fluorescent lectins. Preferred fluorescent phospholipids include Cou-PE, FL-PE, NBD-PE or Cy5-PE. Using Cou-PE as donor with DiSBA-C₆-(3) as acceptor has given a 80% ratio change for a 100 mV change in plasma membrane potential, and typically gives ratio signals twice as large as FL-WGA with the same oxonol.

C. Fluorescently Labelled Antibodies

Antibodies directed against surface antigens such as glycolipids or membrane proteins can also be fluorescently labeled and used as second reagents. For example, FITC-labeled antibodies against the glycolipid GD3 stain the outer surface of the melanoma cell line M21 and give ratio changes up to 10%/100 mV using DiSBA-C₆-(3) as the mobile fluorescent anion. Specificity for particular cell types is likely to be easier to achieve with antibodies than with lectins because antibodies can be raised against nearly any surface marker. Also, microinjected antibodies could label sites on the cytoplasmic face of the plasma membrane, where carbohydrate binding sites for lectins are absent.

D. Cytochromes

Cytochrome c used as a second reagent has also been found to function as a quencher which binds to the outer plasma membrane surface. Accordingly, another suitable class of second reagent comprises cytochrome c or apocytochrome c, with or without a fluorescent group as previously described in connection with other second reagents.

E. Fluorescent Carbohydrates

Yet another preferred class of embodiments of the second reagent includes fluorescently labeled, amphipathic carbohydrates, e.g., cyclodextrins which selectively and tightly bind to the extracellular plasma membrane surface. Typically, the carbohydrates are functionalized with a hydrophobic tail to facilitate intercalation into the membrane and tight membrane binding. The cyclic sugar imparts good water solubility for cellular loading and prohibits membrane translocation. Another added benefit is that the cyclodextrins aid the loading of the oxonol.

F. Fluorescent Peptides and Proteins

Yet another preferred class of embodiments of the second reagent includes fluorescently labeled, amphipathic peptides. Typically such peptides contain several basic residues such as lysines and arginines to bind electrostatically to negatively charged phospholipid head groups, plus several hydrophobic residues to anchor the peptide to the membrane. Optionally, long-chain alkyl substituents such as N-myristoyl, N-palmitoyl, S-palmitoyl, or C-terminal prenyl groups may provide hydrophobicity. The fluorescent label is typically attached via lysine epsilon-amino groups or cysteine sulfhydryl groups.

Yet another preferred class of embodiments of the second reagent includes naturally fluorescent proteins such as the Green Fluorescent Protein (GFP) of *Aequorea victoria* (Cubitt, A. B. et al. 1995. Understanding, improving, and using green fluorescent proteins. *Trends Biochem. Sci.* 20: 448–455; Chalfie, M., and Prasher, D. C. U.S. Pat. No. 5,491,084). Such proteins would be fused to native plasma membrane proteins by expression of tandem DNA constructs in which the DNA sequences encoding the GFP and the native protein are concatenated in frame. Alternatively, the GFP could be fused to a motif that causes attachment of glycosylphosphatidylinositol anchors and targeting of the protein to the plasma membrane.

As the preceding discussion indicates and would be readily appreciated by those skilled in the art, a wide variety of known donor/acceptor pairs can be used as first and second reagents. Particularly preferred combinations include, but are not limited to, the following, in which the first-named fluorophore is the donor and the second is the acceptor: fluorescein/bis-thiobarbiturate trimethineoxonol; Green Fluorescent Protein/bis-thiobarbiturate trimethineoxonol; Green Fluorescent Protein/bis-thiobarbiturate pentameth:ineoxonol; coumarin/bis-thiobarbiturate trimethineoxonol; coumarin/bis-thiobarbiturate pentamethineoxonol; bis-thiobarbiturate trimethineoxonol/Texas Red; bis-thiobarbiturate trimethineoxonol/resorufin; bis-thiobarbiturate trimethineoxonol/Cy5; bis-thiobarbiturate trimethineoxonol/bis-thiobarbiturate pentamethineoxonol; Texas Red/bis-thiobarbiturate pentamethineoxonol; NBD/bis-thiobarbiturate trimethineoxonol; NBD/bis-thiobarbiturate pentamethineoxonol.

III. Linker Groups Between First and Second Reagent

In some particularly preferred embodiments of the compositions and methods of the present invention, a linker group is employed between the first and second fluorophores. The linker group maintains a certain minimum proximity between the first and second fluorophores and ensures efficient energy transfer between the donor and acceptor (or fluorophore and quencher) when they are on the same side of the membrane, even at low concentrations. The good energy transfer allows one to separate the donor emission further from the acceptor absorbance and thus decrease the spectral crosstalk that contributes to the reduction of the voltage-sensitive ratio change from theoretical values. Another major advantage of a linker is that it converts the system into a unimolecular phenomenon. This greatly simplifies the fluorescence readout, ensures 1:1 stoichiometry of donor and acceptor (or fluorophores and quencher), and eliminates the need for optimizing relative loading levels of donor and acceptor for an optimum voltage-sensitive fluorescence change (with the additional benefit of minimal cellular perturbation and toxicity). The linker group is long enough to span the entire membrane.

The hydrophobic fluorescent anion and the second reagent are attached to each other by means of a bifunctional linker. "Linker group" shall mean the "chemical arm" between the first and second reagent. As one skilled in the art will recognize, to accomplish the requisite chemical structure, each of the reactants must contain the necessary reactive groups.

Representative combinations of such groups are amino with carboxyl to form amide linkages, or carboxy with hydroxy to form ester linkages or amino with alkyl halides to form alkylamine linkages, or thiols with thiols to form disulfides, or thiols with maleimides or alkyl halides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the two species to each other. The portions of the linker closest to the second reagent may be hydrophilic, whereas the portions of the linker closest to the mobile fluorescent anion should be hydrophobic to permit insertion into the membrane and to avoid retarding the voltage-dependent translocation of the anion. The covalent linkages should be stable relative to the solution conditions under which the cells are loaded. Generally preferred linking groups will comprise 20–40 bonds from one end to the other and 0–10 heteroatoms (NH, O, S) and may be branched or straight chain. Without limiting the foregoing, it should be evident to one skilled in the art that only combinations of atoms which are chemically compatible comprise the linking group. For example, amide, ester, thioether, thioester, keto, hydroxyl, carboxyl, ether groups in combinations with carbon—carbon bonds are acceptable examples of chemically compatible linking groups. Other chemically compatible linkers may be found in U.S. Pat. No. 5,470,997 (col. 2 and col. 4–7) and U.S. Pat. No. 5,470,843 (cols. 11–13).

Figure 11:
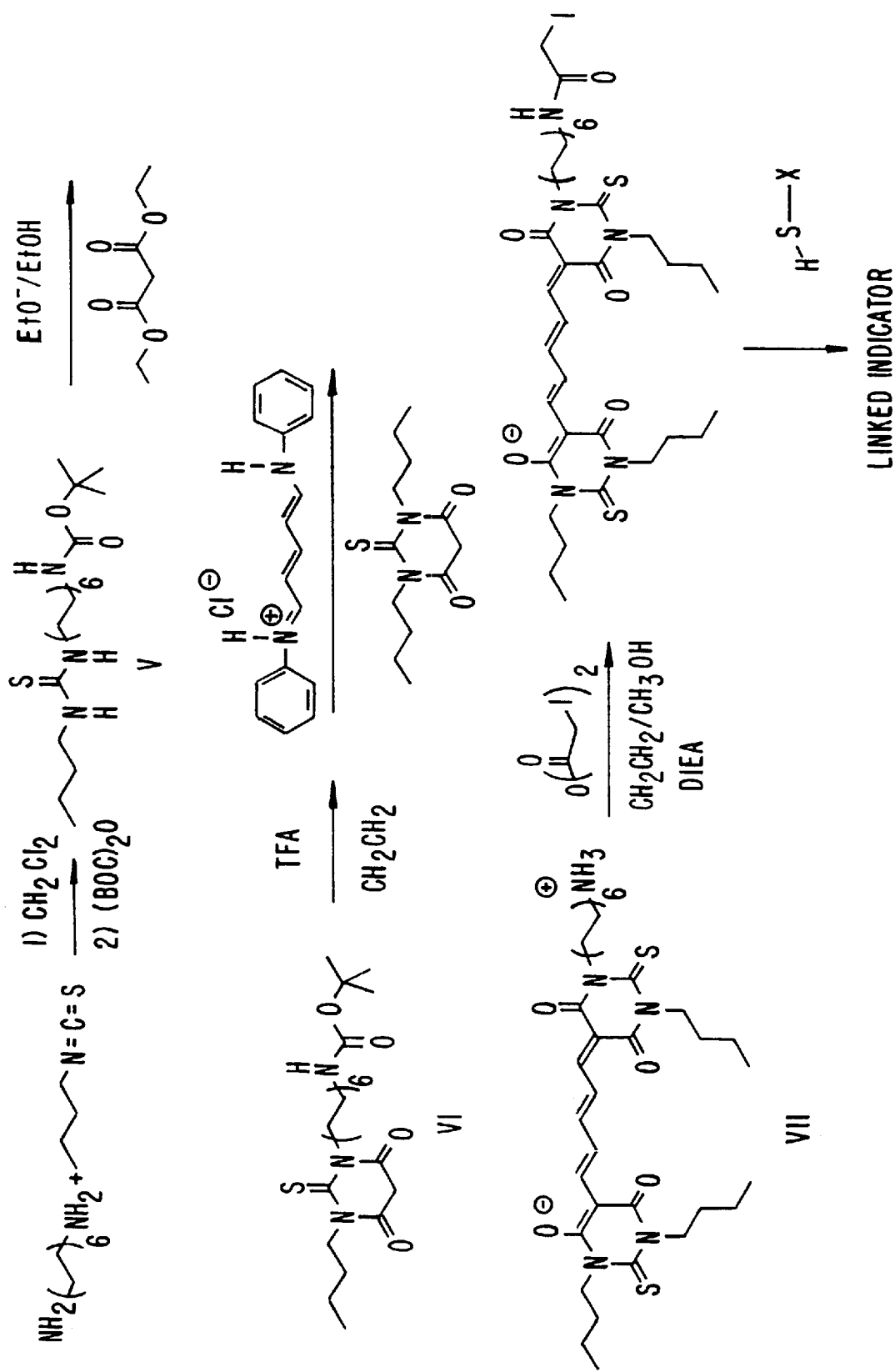
FIG. 11 shows a synthesis of an asymmetric oxonol and its linkage to a second reagent.

Asymmetric 1,3-substituted thioureas have been prepared for use in synthesizing oxonols with N-substituted linkers containing terminal reactive groups capable of conjugating to appropriate second reagent fluorophores/quenchers. In one example, one of the oxonol substituents is a pentyl chain ($C_5$) with a terminal bromide or tosylate group. Thiobarbiturates have been synthesized from these thioureas and diethylmalonate in ethoxide/ethanol. Mixed pentamethine oxonols prepared from 1 equivalent of the barbiturate with functionalized linkers and 1,3-dibutyl thiobarbiturate have been characterized. An exemplary synthesis is depicted in FIG. 11. It will be recognized that oxonols with alkyl chains of length other than $C_5$ can be readily prepared by such a method and are contemplated as within the scope of this invention.

One preferred class of suitable linkers includes bi-functionalized polyalkylene glycol oligomers (polyethyleneglycol, polypropyleneglycol, polybutyleneglycol, etc.) of an appropriate length to span the plasma membrane (25–30 carbon equivalents), for example 8–10 PEG units. The oxygen (or sulfur, in the corresponding thio-analogs thereof) modulates; the hydrophobicity and hence translocation rate and loading. Compounds joined by such linker groups have the general formula

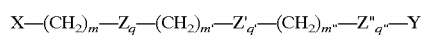

$$X-(CH_2)_m-Z_q-(CH_2)_{m'}-Z'_{q'}-(CH_2)_{m''}-Z''_{q''}-Y$$

wherein:

X is a hydrophobic fluorescent anion;

Y is a fluorescent second reagent;

Z, Z', Z" are independently O, S, SS, CO, COO;

m, m' and m" are integers from 0 to about 32;

q, q', and q" are independently 0 or 1; and m+q+m'+q'+m"+q" is from about 20 to 40 (preferably between 25 and 35).

Preferably Z is S, i.e., the linkers are polyalkylene thioethers; m=5, Z=S, q=1, m'=12, Z'=S, q'=1, m"=11, Z"=CO, and q"=1.

Another class of suitable linkers includes functionalized alkyl chains with terminal thiol groups that form a central disulfide linkage. The disulfide functions as a hydrophobic swivel in the center of the membrane. These compounds have the general formula

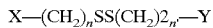

$$X—(CH_2)_n SS(CH_2)2_{n'}—Y$$

wherein:

X is a hydrophobic fluorescent anion;

Y is a fluorescent second reagent;

n and n' are integers from 0 to about 32 wherein n+n' is less than or equal to 33.

Figure 12:
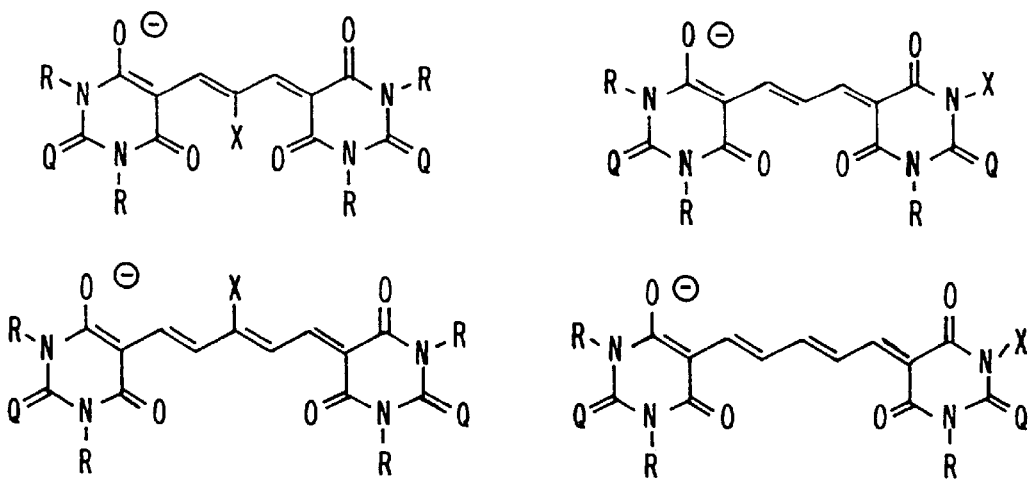
FIG. 12 shows possible linkage points (X) of oxonols to a second reagent.

As would be readily appreciated by those skilled in the art, the linker groups may be reacted with appropriately substituted or functionalized first and second fluorophores using conventional coupling chemistries. Further, it is evident that the linker group may be attached to a fluorophore at a variety of different positions. Important locations (X) for attachment of the linker in exemplary classes of oxonols are illustrated in FIG. 12.

IV. Measurement Methods

In one class of embodiments of the present invention, the hydrophobic ion fluorescence on one face of the membrane is quenched by a mechanism other than FRET. FRET has the advantages of working over long distances, which minimizes the necessary concentration of acceptors, and of giving ratiometric output at two emission wavelengths. However, if FRET is too efficient over very long distances greater than the thickness of the membrane, it can fail to discriminate between acceptors on the same vs. opposite sides of the membrane. The other mechanisms of quenching are much shorter-range and should never be effective across the thickness of the membrane.

The second fluorophore/quencher can be located on either the intracellular or the extracellular face, as long as it is specific to one or the other. In the specific examples reported herein, the extracellular surface was targeted for convenience.

FRET or fluorescence quenching is best detected by emission ratioing which can distinguish the two populations of the mobile fluorophore, i.e, those bound to the extracellular vs. those bound to the intracellular face of the membrane. In particular, FRET using a fluorescent acceptor provide an emission ratio change that is well suited to laser-scanning confocal microscopy and internally corrects for variations in donor loading, cell thickness and position (including motion artifacts), and excitation intensity. Emission ratios usually change by larger percentages than either emission wavelength signal alone, because the donor and acceptor emissions should change in opposite directions, which reinforce each other when ratioed. If emission ratioing is not desirable or possible, either wavelength can still be used alone, or the change in donor excited-state lifetime monitored.

Emission ratios are measured either by changing the passband of a wavelength-selective filter in front of a single detector, or preferably by splitting the emitted light with a dichroic mirror and measuring two wavelength bands simultaneously with two detectors, which may each be preceded by additional wavelength-selecting filters. In the first method, the wavelength-selective filters may be two or more interference filters with different passbands alternately placed in front of the detector, or they may be a continuously tunable monochromator which is repeatedly scanned over a wavelength range. The advantage of the first method is that only one detector is used, which economizes on detectors and avoids the problem of precisely matching two detectors. The advantages of the second method, using a dichroic mirror and two separate detectors, are that the two emissions may be measured truly simultaneously rather than sequentially, and that it makes more efficient use of the photons emitted from the sample.

Molecular specificity for particular cell types in a mixed population may be introduced by using cell-specific antibodies or lectins as the carriers of the extracellular fluorescent label, or by using Green Fluorescent Protein specifically expressed in a given cell type as the intra- or extracellular label. Specifically labeled cells also reduce background staining and provide large fluorescence changes in complex tissue.

High sensitivity is achieved when the voltage sensor (i.e., the hydrophobic anion of the first reagent) translocates at least a full unit charge nearly all the way through the membrane. Even without specific ion channels or transporters, such translocation can be quite rapid if the ion is negatively charged, delocalized, and hydrophobic. For example, the lipid-soluble non-fluorescent anion of dipicrylamine (2,2',4,4',6,6'-hexanitrodiphenylamine) produces displacement currents in excitable tissue with submillisecond kinetics, comparable in speed to sodium channel gating currents [Benz, R. and Conti, F. 1981. Structure of the squid axon membrane as derived from charge-pulse relaxation studies in the presence of absorbed lipophilic ions. *J. Membrane Biol.* 59:91–104, Benz, R. and Nonner, W. 1981. Structure of the axolemma of frog myelinated nerve: relaxation experiments with a lipophilic probe ion. *J. Membrane Biol.* 59:127–134; Fernandez, J. M., Taylor, R. E., and Bezanilla, F. 1983. Induced capacitance in the squid giant axon. *J. Gen. Physiol.* 82:331–346]. However, voltage sensing should not require further diffusion of the ion through the unstirred aqueous layers, because that slows the response and generates a sustained leakage current.

To create an optical readout from the translocation of the fluorescent hydrophobic ion (i.e., the first reagent) from one side of the plasma membrane to the other side, FRET or fluorescence quenching between the translocating ion and a fluorophore or quencher (i.e., the second reagent) fixed to just one face of the plasma membrane is employed. Most conveniently, the extracellular face is employed.

Figure 1B:
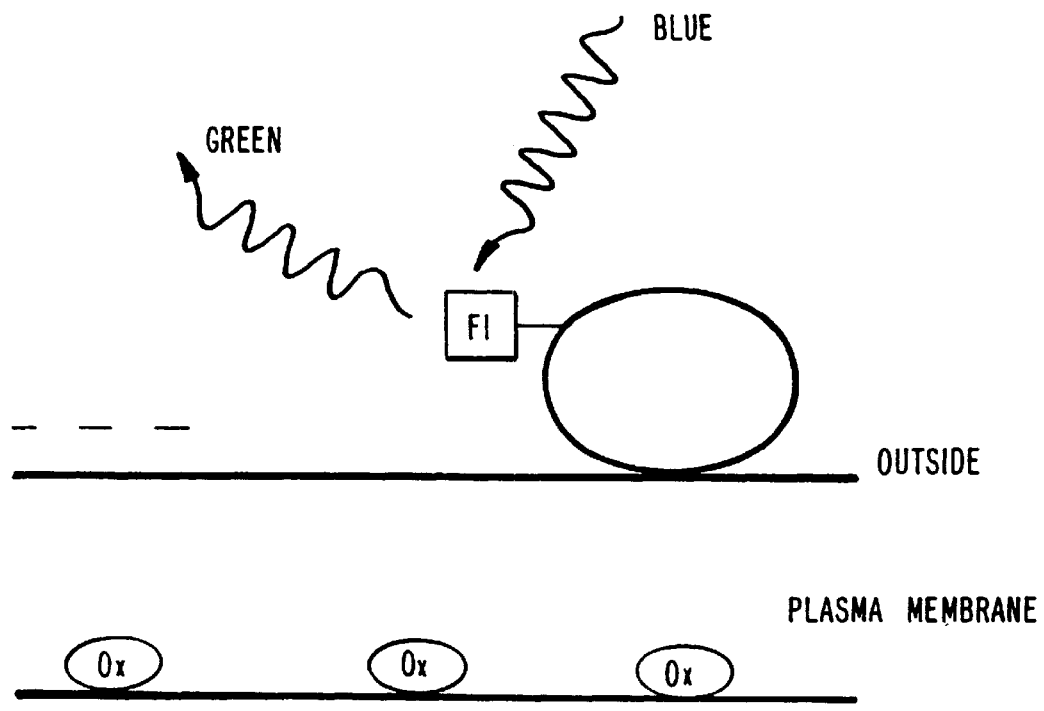

By way of example, and not limitation, the case where the translocating ions are anionic fluorescent acceptors which absorb at wavelengths that overlap with the emission spectrum of the extracellularly fixed donor fluorophores is schematically shown in FIG. 1. At a resting negative membrane potential (A) permeable oxonols have a high concentration at the extracellular surface of the plasma membrane and energy transfer from the extracellularly bound FL-WGA (fluorescein-wheat germ agglutinin) is favored. FRET is symbolized by the straight arrow from lectin to oxonol. At a positive membrane potential (B) the anions are located primarily on the intracellular surface of the membrane and energy transfer is greatly reduced because of their increased mean distance from the donors on the extracellular surface.

Figure 5:
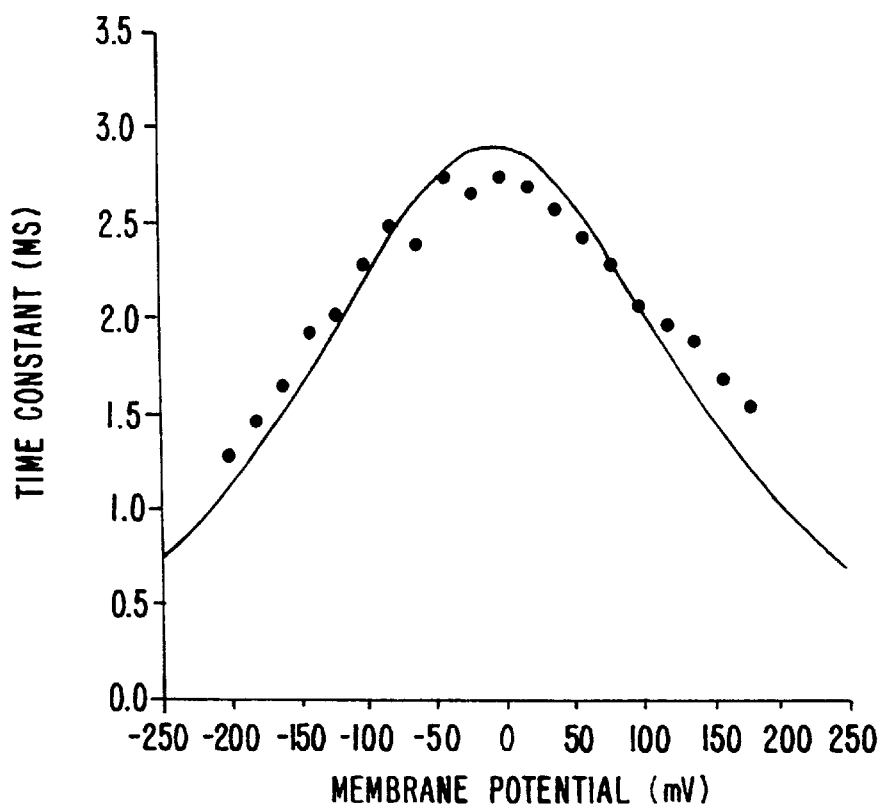
FIG. 5 illustrates voltage dependence of DiSBA-$C_6$-(3) displacement current time constants in L-M(TK$^-$)cells for the same data shown in FIG. 4.

The speed of the voltage-sensitive fluorescence response depends on the translocation rate of the fluorophore from one site to the other. The speed of response for DiSBA-C$_6$-(3) is shown in FIG. 5 and follows the general equations (1) and (2). As this equation indicates, fluorescent ions which jump across the membrane on a millisecond timescale in response to biologically significant changes in transmembrane potential are needed to follow rapid polarization/depolarization kinetics. Slower-jumping ions would not be useful, for example, in following fast electrical signals in neuronal tissue (a primary application of the compositions and methods of the present invention). The development and discovery of such molecules with the added constraint of being fluorescent is not trivial.

The mobile hydrophobic anions can be donors rather than acceptors. Each of the alternatives has its own advantages. An example with the hydrophobic ion being the FRET donor is the DiSBA-C$_6$-(3)/Texas Red WGA combination. A primary advantage of this arrangement is that it minimizes the concentration of the hydrophobic dye molecule in the membrane; this reduces toxicity and cellular perturbations resulting from the displacement current and any photodynamic effects. Another advantage is the generally higher quantum yields of fluorophores bound in membranes relative to those on proteins or water; this gives better FRET at a given distance.

Bis-(1,3-dialkyl-2-thiobarbiturate)-trimethineoxonols, where alkyl is n-hexyl and n-decyl (DiSBA-C$_6$-(3) and DiSBA-C$_{10}$-(3) respectively) have been shown herein to function as donors to Texas Red labeled wheat germ agglutinin (TR-WGA) and as acceptors from fluorescein labeled lectin (FL-WGA). In voltage-clamped fibroblasts, the translocation of these oxonols was measured as a displacement current with a time constant of about 2 ms for 100 mV depolarization at 20° C., which equals the speed of the fluorescence changes. Fluorescence ratio changes of between 4–34% were observed for a 100 mV depolarization in fibroblasts, astrocytoma cells, beating cardiac myocytes, and B104 neuroblastoma cells. The large fluorescence changes allowed high speed confocal imaging.

Single cells were used in the examples so that the optical signals could be compared with voltage changes accurately known from traditional microelectrode techniques, such as patch clamping, which are applicable only to single cells. However, it should be apparent that the dyes can be used for many applications in which microelectrodes are not applicable. Comparison with microelectrodes is needed merely for accurate calibration and proof that the mechanism of fluorescence signal generation is as described herein. The two reagent compositions and methods described herein can either resolve the different electrical potentials of many neighboring cells or neighboring parts of a single cell, or give an average reading for all the membrane locations, depending on whether the optical signal is spatially imaged or pooled.

The methods described herein are applicable to a wide variety of membranes. In particular, membrane potentials in membranes of biological cells can be detected and monitored. The method finds greatest utility with plasma membranes, especially the outermost plasma membrane of mammalian cells. Representative membranes include, but are not limited to, subcellular organelles, membranes of the endoplasmic reticulum, secretory granules, mitochondria, microsomes and secretory vesicles. Cell types which can be used include but are not limited to, neurons, cardiac cells, lymphocytes (T and B lymphocytes, nerve cells, muscle cells and the like.

V. Drug Screening

The invention also provides methods for screening test samples such as potential therapeutic drugs which affect membrane potentials in biological cells. These methods involve measuring membrane potentials as described above in the presence and absence (control measurement) of the test sample. Control measurements are usually performed with a sample containing all components of the test sample except for the putative drug. Detection of a change in membrane potential in the presence of the test agent relative to the control indicates that the test agent is active. Membrane potentials can be also be determined in the presence or absence of a pharmacologic agent of known activity (i.e., a standard agent) or putative activity (i.e., a test agent). A difference in membrane potentials as detected by the methods disclosed herein allows one to compare the activity of the test agent to that of the standard agent. It will be recognized that many combinations and permutations of drug screening protocols are known to one of skill in the art and they may be readily adapted to use with the method of membrane potential measurement disclosed herein to identify compounds which affect membrane potentials. Use of the membrane potential determination technique disclosed herein in combination with all such methods are contemplated by this invention. In a particular application, the invention offers a method of identifying a compound which modulates activity of an ion channel, pump, or exchanger in a membrane, comprising:

(a) loading the cells with the first and second reagents, which together measure membrane potential as described above;

(b) determining the membrane potential as described above;

(c) exposing the cells to the test sample;

(d) redetermining the membrane potential and comparing with the result in (b) to determine the effect of the test sample;

(e) optionally, exposing the membrane to a stimulus which modulates an ion channel, pump or exchanger, and redetermining the membrane potential and comparing with the result in (d) to determine the effect of the test sample on the response to the stimulus.

In another application, the invention offers a method of screening test samples to identify a compound which modulates the activity of an ion channel, pump or exchanger in a membrane, comprising:

(a) loading a first set and a second set of cells with first and second reagents which together measure membrane potential;

(b) optionally, exposing both the first and second set of cells to a stimulus which modulates the ion channel, pump or exchanger;

(c) exposing the first set of cells to the test sample;

(d) measuring the membrane potential in the first and second sets of cells; and (e) relating the difference in membrane potentials between the first and second sets of cells to the ability of a compound in the test sample to modulate the activity of an ion channel, pump or exchanger in a membrane.

Ion channels of interest include, but are not limited to, sodium, calcium, potassium, nonspecific cation, and chloride ion channels, each of which may be constitutively open, voltage-gated, ligand-gated, or controlled by intracellular signaling pathways.

Biological cells which can be screened include, but are not limited to primary cultures of mammalian cells, cells dissociated from mammalian tissue, either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like. The invention also includes the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel) and methods for their expression in cell lines of interest is within the knowledge of one of skill in the art (see, U.S. Pat. No. 5,436,128). Representative cultured cell lines derived from humans and other mammals include LM (TK$^-$) cells, HEK293 (human embryonic kidney cells), 3T3 fibroblasts, COS cells, CHO cells, RAT1 and HLHepG2 cells.

The screening methods described herein can be made on cells growing in or deposited on solid surfaces. A common technique is to use a microtiter plate well wherein the fluorescence measurements are made by commercially available fluorescent plate readers. The invention includes high throughput screening in both automated and semiautomated systems. One such method is to use cells in Costar 96 well microtiter plates (flat with a clear bottom) and measure fluorescent signal with CytoFluor multiwell plate reader (Perseptive Biosystems, Inc., MA) using two emission wavelengths to record fluorescent emission ratios.

The invention may be better understood with reference to the accompanying examples, which are intended for purposes of illustration only and should not be construed as in any sense limiting the scope of the invention as defined in the claims appended hereto. XAMPLES Example I Synthesis of Oxonol Dyes All starting materials and reagents were of the highest purity available (Aldrich; Milwaukee, Wis.) and used without further purification, except where noted. Solvents were HPLC grade (Fisher) and were dried over activated molecular sieves 3 Å. NMR spectra were acquired on a Varian Gemini 200 MHz spectrometer (Palo Alto, Calif.). The spectra were referenced relative to the residual solvent peak (CHCl$_3$, =7.24 ppm). Fluorescence spectra were taken on a SPEX Fluorolog-2 (Edison, N.J.) and were corrected for lamp and detector wavelength variations using the manufacturer supplied correction files.

Bis-(1,3-dibutyl-2-thiobarbiturate)-trimethineoxonol DiSBA-C$_4$-(3):

DiSBA-C$_4$-(3) was synthesized based on the procedure for the ethyl derivative [British Patent 1,231,884]. 1,3-di-butyl-thiobarbiturate (500 mg, 2 mmol) was dissolved in 700 μL of pyridine. To this solution, a mixture of 181 μL (1.1 mmol) of malonaldehyde bis(dimethyl acetal) and 100 μL of 1 M HCl was added. The solution immediately turned red. After 3 h, half of the reaction mixture was removed and 2 equiv. of the protected malonaldehyde was added every hour for 4 h to the remaining mixture. The reaction mixture was then filtered to collect purple/black crystals of the DiSBA-C$_4$-(3) pyridinium salt. After washing the crystals with water and then drying under vacuum (0.5 torr), 67.2 mg of pure product was collected. $^1$H NMR (CDCl$_3$): 8.91 (2H, d, J=5.1 Hz, py), 8.76 (1H, t, J=13.7 Hz, central methine), 8.52 (1H, t, J=8.0 Hz, py), 8.16 (2H, d, J=13.9 Hz, methine), 8.00 (2H, dd, J$_1$$^{-J}$$_2$=6.9 Hz, py), 4.47 (8H, cm, NCH$_2$CH$_2$CH$_2$CH$_3$), 1.69 (8H, cm, NCH$_2$CH$_2$CH$_2$CH$_3$), 1.39 (8H, cm, NCH$_2$CH$_2$CH$_2$CH$_3$), 0.95 (12H, t, J=6.4 Hz, methyl).

To prepare 1,3-di-butyl-thiobarbiturate, 1.22 g of Na (53 mmol) was slowly dissolved in 20 mL of dry ethanol under argon. To the ethoxide solution, 8.5 g (8 mL, 53 mmol) of diethyl malonate followed by 5 g (26.5 mmol) of dibutylthiourea were added. The reaction mixture was heated and refluxed for 3 days. After cooling, the mixture was filtered. The filtrate was clarified with addition of water. Concentrated HCl was then added until the pH was 1–2. The acidic filtrate was then extracted 3× with hexanes. The extract was concentrated and 5.5 g of crude product precipitated out of solution. The solid was recrystallized from methanol with addition of small amounts of water yielding 4.23 g of the pure barbituric acid (65%). $^1$H NMR (CDCl$_3$): 4.33 (4H, cm, NCH$_2$CH$_2$CH$_2$CH$_3$), 3.71 (2H, s, ring CH$_2$), 1.63 (4H, cm, NCH$_2$CH$_2$CH$_2$CH$_3$), 1.35 (4H, cm, NCH$_2$CH$_2$CH$_2$CH$_3$), 0.94 (6H, t, J=6.2 Hz, methyl).

Bis-(1,3-dihexyl-2-thiobarbiturate)-pentamethineoxonol (DiSBA-C$_6$-(5)):

1,3-dihexyl-2-thiobarbituric acid (200 mg, 0.64 mmol) and glutacondialdehyde dianil monohydrochloride (whose Chem. Abs. name is N-[5-(phenylamino)-2,4-pentadienylidene]benzenamine, monohydrochloride) (91 mg, 0.32 mmol) were mixed in 1 mL pyridine. Within 10 s, the solution turned blue. After letting the reaction mixture stir for 1.5 h, the solvent was removed under high vacuum. The residue was dissolved in CHCl$_3$ and chromatographed on silica gel eluting with a (93:7) CHCl$_3$/MeOH solution. The pure blue oxonol (72 mg) was recovered. $^1$HNMR (CDCl$_3$/CD$_3$OD): d 7.60–7.80 (cm, 4H, methines), 7.35 (t, J=11.3 Hz, 1H, central methine), 4.31 (cm, 8H, NCH$_2$R), 1.57 (cm, 8H, NCH$_2$CH$_2$R), 1.20 (br m, 24H, bulk methylenes), 0.74 (br t, 12H, methyl).

Figure 13:
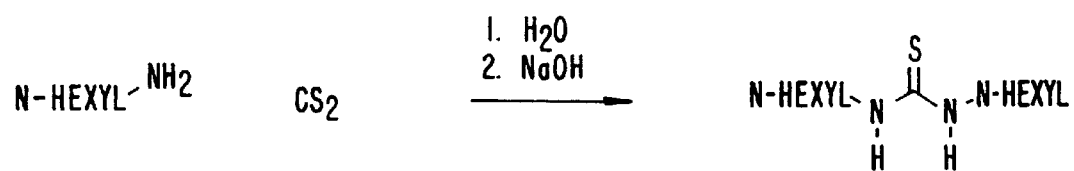
FIG. 13 shows a synthesis of Di-SBA-$C_6$-(3).
Figure 13:
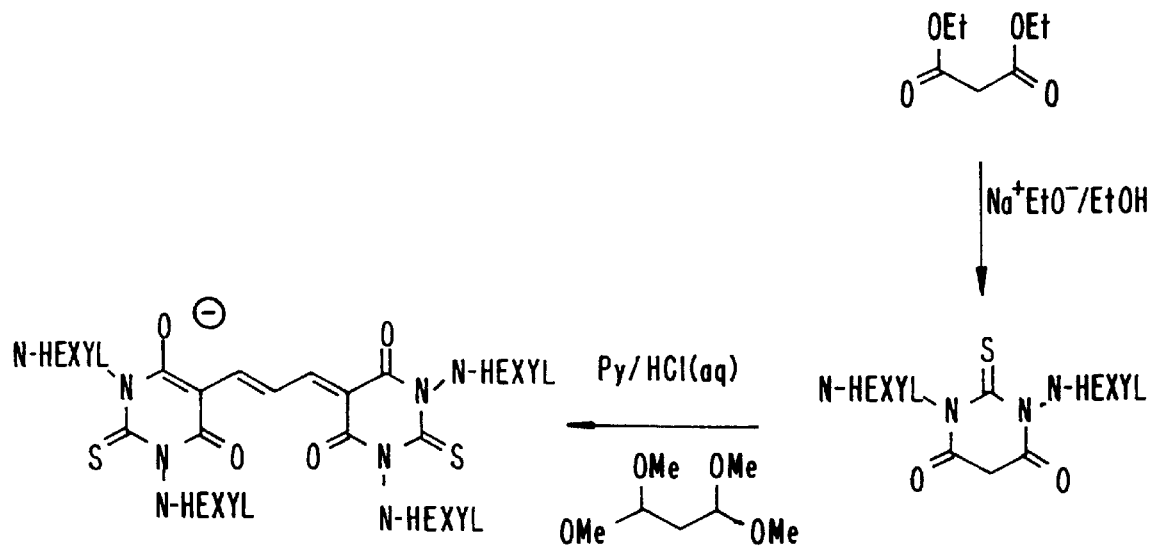

Other oxonols were made using the same procedure, starting with the appropriate thiourea prepared from requisite primary amine and carbon disulfide [Bortnick, N., Luskin, L. S., Hurwitz, M. D., and Rytina, A. W. 1956. t-Carbinamines, RR'R"CNH$_2$. III. The preparation of isocyanates, isothiocyanates and related compounds. J. Am. Chem. Soc. 78:4358–4361]. An exemplary synthesis of Di-SBA-C$_6$-(3) is depicted in FIG. 13.

Example II

Synthesis of Fluorescent Phospholipids

Cou-PE:

3-amidoglycine-6-chloro-7-butyryloxy coumarin was synthesized as described in pending U.S. patent application Ser. No. 08/407,554, filed Mar. 20, 1995 as set out below. For synthesis of 2,4 dihydroxy-5-chlorobenzaldehyde, 21.7 g (0.15 Mol) 4-chlororesorcinol were dissolved in 150 ml dry diethyl ether and 27 g finely powdered zinc (II) cyanide and 0.5 g potassium chloride were added with stirring. The suspension was cooled on ice. A strong stream of hydrogen chloride gas was blown into the solution with vigorous stirring. After approximately 30 minutes the reactants were dissolved. The addition of hydrogen chloride gas was continued until it stopped being absorbed in the ether solution (approx. 1 hour). During this time a precipitate formed. The suspension was stirred for one additional hour on ice. Then the solid was let to settle. The ethereal solution was poured from the solid. The solid was treated with 100 g of ice and heated to 100 degrees C. in a water bath. Upon cooling the product crystallized in shiny plates from the solution. They were removed by filtration on dried over potassium hydroxide. The yield was 15.9 g (0.092 Mol, 61%). $^1$H NMR (CDCl$_3$): δ 6.23 ppm (s, 1H, phenol), δ 6.62 ppm (s, 1H, phenyl), δ 7.52 ppm (s, 1H, phenyl), δ 9.69 ppm (s, 1H, formyl), δ 11.25 ppm (s, 1H, phenol).

To prepare 3-carboxy 6-chloro 7-hydroxy coumarin, 5.76 g (0.033 Mol) 2,4-dihydroxy-5-chlorobenzaldehyde and 7.2 g (0.069 Mol) malonic acid were dissolved in 5 ml warm pyridine. 75 microliters aniline were stirred into the solution and the reaction let to stand at room temperature for 3 days. The yellow solid that formed was broken into smaller pieces and 50 ml ethanol was added. The creamy suspension was filtered through a glass frit and the solid was washed three times with 1 N hydrochloric acid and then with water. Then the solid was stirred with 100 ml ethyl acetate, 150 ml ethanol and 10 ml half concentrated hydrochloric acid. The solvent volume was reduced in vacuo and the precipitate recovered by filtration, washed with diethyl ether and dried over phosphorous pentoxide. 4.97 g (0.021 Mol, 63%) of product was obtained as a white powder. $^1$H NMR (dDMSO): δ 6.95 ppm (s, 1H), δ 8.02 ppm (s, 1H), δ 8.67 ppm (s, 1H).

To prepare 7-butyryloxy-3-carboxy-6-chlorocoumarin, 3.1 g (12.9 mMol) 3-carboxy-6-chloro-7-hydroxycoumarin were dissolved in 100 ml dioxane and treated with 5 ml butyric anhydride, 8 ml pyridine and 20 mg dimethyl aminopyridine at room temperature for two hours. The reaction solution was added with stirring to 300 ml heptane upon which a white precipitate formed. It was recovered by filtration and dissolved in 150 ml ethyl acetate. Undissolved material was removed by filtration and the filtrate extracted twice with 50 ml 1 N hydrochloric acid/brine (1:1) and then brine. The solution was dried over anhydrous sodium sulfate. Evaporation in vacuo yielded 2.63 g (8.47 mmol, 66%) of product. $^1$H NMR (CDCl$_3$): δ 1.08 ppm (t, 3H, J=7.4 Hz, butyric methyl), δ 1.85 ppm (m, 2H, J$_1$≈J$_2$=7.4 Hz, butyric methylene), δ 2.68 ppm (t, 2H, J=7.4 Hz, butyric methylene), δ 7.37 ppm (s, 1H, coumarin), δ 7.84 ppm (s, 1H, coumarin), δ 8.86 ppm (s, 1H, coumarin) Preparation of 7-butyryloxy-3-benzyloxycarbonylmethylaminocarbonyl-6-chlorocoumarin is effected as follows. 2.5 g (8.06 mMol) 7-Butyryloxy-3-carboxy-6-chlorocoumarin, 2.36 g hydroxybenztriazole hydrate (16 mMol) and 1.67 g (8.1 mMol) dicyclohexyl carbodiimide were dissolved in 30 ml dioxane. A toluene solution of O-benzylglycine [prepared by extraction of 3.4 g (10 mMol) benzylglycine tosyl salt with ethyl acetate-toluene-saturated aqueous bicarbonate-water (1:1:1:1, 250 ml), drying of the organic phase with anhydrous sodium sulfate and reduction of the solvent volume to 5 ml] was added dropwise to the coumarin solution. The reaction was kept at room temperature for 20 hours after which the precipitate was removed by filtration and washed extensively with ethylacetate and acetone. The combined solvent fractions were reduced to 50 ml on the rotatory evaporator upon which one volume of toluene was added and the volume further reduced to 30 ml. The precipitating product was recovered by filtration and dissolved in 200 ml chloroform—absolute ethanol (1:1). The solution was reduced to 50 ml on the rotatory evaporator and the product filtered off and dried in vacuo yielding 1.29 g of the title product. Further reduction of the solvent volume yielded a second crop (0.64 g). Total yield: 1.93 g (4.22 mMol, 52%). $^1$H NMR (CDCl$_3$): δ 1.08 ppm (t, 3H, J=7.4 Hz, butyric methyl), δ 1.84 ppm (m, 2H, J$_1$≈J$_2$=7.4 Hz, butyric methylene), δ 2.66 ppm (t, 2H, J=7.4 Hz, butyric methylene), δ 4.29 ppm (d, 2H, J=5.5 Hz, glycine methylene), δ 5.24 ppm (s, 2H, benzyl), δ 7.36 ppm (s, 1H, coumarin), δ 7.38 ppm (s, 5H, phenyl), δ 7.77 ppm (s, 1H, coumarin), δ 8.83 ppm (s, 1H, coumarin), δ 9.15 ppm (t, 1H, J=5.5 Hz, amide).

7-Butyryloxy-3-carboxymethylaminocarbonyl-6-chlorocoumarin was prepared as follows. 920 mg (2 mMol) 7-butyryloxy-3-benzyloxycarbonylmethylaminocarbonyl-6-chlorocoumarin were dissolved in 50 ml dioxane. 100 mg palladium on carbon (10%) and 100 microliters acetic acid were added to the solution and the suspension stirred vigorously in a hydrogen atmosphere at ambient pressure. After the uptake of hydrogen seized the suspension was filtered. The product containing carbon was extracted five times with 25 ml boiling dioxane. The combined dioxane solutions were let to cool upon which the product precipitated as a white powder. Reduction of the solvent to 20 ml precipitates more product. The remaining dioxane solution is heated to boiling and heptane is added until the solution becomes cloudy. The weights of the dried powders were 245 mg, 389 mg and 58 mg, totaling 692 mg (1.88 mMol, 94%) of white product. $^1$H NMR (dDMSO): δ 1.02 ppm (t, 3H, J=7.4 Hz, butyric methyl), δ 1.73 ppm (m, 2H, J$_1$≈J$_2$=7.3 Hz, butyric methylene), δ 2.70 ppm (t, 2H, J=7.2 Hz, butyric methylene), δ 4.07 ppm (d, 2H, J=5.6 Hz, glycine methylene), δ 7.67 ppm (s, 1H, coumarin), δ 8.35 ppm (s, 1H, coumarin), δ 8.90 ppm (s, 1H, coumarin), δ 9.00 ppm (t, 1H, J=5.6 Hz, amide).

6-chloro-7-(n-butyryloxy)coumarin-3-carboxamidoacetic acid (26.2 mg, 100 mmol) was dissolved in 2 mL of 1:1 CHCl$_3$/dioxane. Isobutylchloroformate (14.3 mL, 110 mmol) was added under Ar at 4° C. and left stirring for 30 min. Separately, dimyristoylphosphatidylethanolamine (DMPE) (20 mg, 31.5 mmol) was dissolved in 1 mL of CHCl$_3$ with 1 drop of dry MeOH and 6 mL (34.5 mmol) of diisopropylethylamine (DIEA) added. The mixed anhydride solution was then pipetted into the phospholipid solution. After 2 h, the solvent was removed under vacuum. The residue was dissolved in 3 mL of MeOH and mixed with 3 mL of 0.25 M NaHCO$_3$. The solution almost immediately turn yellow and was stirred for 15 min. The solution was then extracted 3–5 times with CHCl$_3$. A bad emulsion is formed. The extracts were combined and concentrated. The residue was dissolved in 1 mL 1:1 MeOH/H$_2$O and purified on a C$_{18}$ reverse phase column (1.7×7 cm). Eluting with the same solvent, a fluorescent band passed through the column, followed by a slower one. The solvent polarity was decreased to 9:1 MeOH/H$_2$O and the major yellow band then eluted off the column. After concentration and drying 2.5 mg (2.74 mmol) of pure product was collected. $^1$HNMR (CD$_3$OD): d 8.72 (s, 1H, coumarin), 7.81 (s, 1H, coumarin), 6.84 (s, 1H, coumarin), 5.25 (cm, 2H), 4.43 (dd, J$_1$=12.1 Hz, J$_2$=3.2 Hz), 4.22 (d, J=6.6 Hz, 1H), 4.13 (s, ~4H), 3.7–4.1 (cm, ~11H), 3.47 (cm, ~3H), 3.2–3.3 (~q), 2.31 (cm ~7H), 1.57 (br S, ~8H, CH$_2$ a to carbonyl), 1.2–1.5 (cm, ~63H, bulk CH$_2$'s), 0.92 (unres t, ~12H, CH$_3$). Electrospray (neg. ion) MS [MeOH/H$_2$O: 95/5] (peak, rel. int.) 456.8 (M$^{-2}$, 20), 524.5 (50), 704.9 (6), 734.7 (100), 913.9 (M$^{-1}$, 95); deconvoluted M=915.3 amu; calc. M=915.5 amu. UV-vis (MeOH/HBSS; 2/1) l$_{max}$=414 nm. Fluorescence (MeOH/HBSS; 2/1) l$_{emax}$=450 nm, Quantum Yield=1.0.

Cy5-PE:

DMPE (1.0 mg, 1.6 mmol) was dissolved in 650 mL of (12:1) CHCl$_3$/MeOH and DIEA (1 mL, 5.7 mmol) was added. Separately, Cy5-OSu (Amersham; Arlington Heights, Ill.), the N-hydroxysuccinimide ester of N-ethyl-N'-(5-carboxypentyl)-5,5'-disulfoindodicarbocyanine, (0.8 mg, 1 mmol) was dissolved in 150 mL of (2:1) CHCl$_3$/MeOH and added to the phospholipid solution. After 3 h, the solvent was removed under vacuum. The residue was dissolved in MeOH and loaded on a C$_{18}$ reverse phase column (1×10 cm) equilibrated with 1:1 MeOH/H$_2$O. Eluting with the same solvent, the hydrolyzed ester was removed. The polarity was decreased to 9:1 MeOH/H$_2$O and the pure blue product was eluted off the column, yielding 400 mg (310 nmol, 31%).

Example III

Synthesis of Linker For Donors and Acceptors

Figure 14:
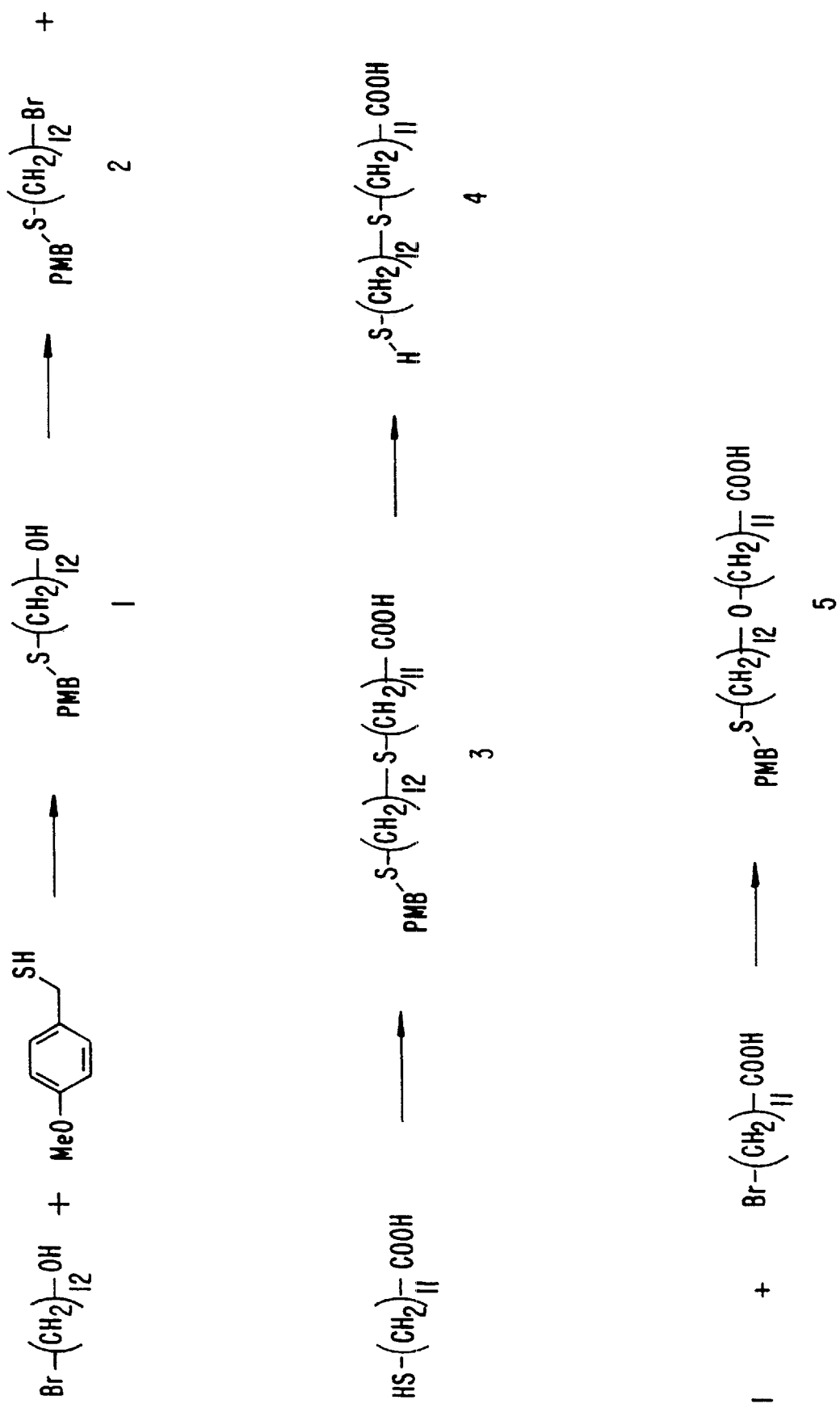
FIG. 14 shows the synthesis of a bifunctional linker.
Figure 15:
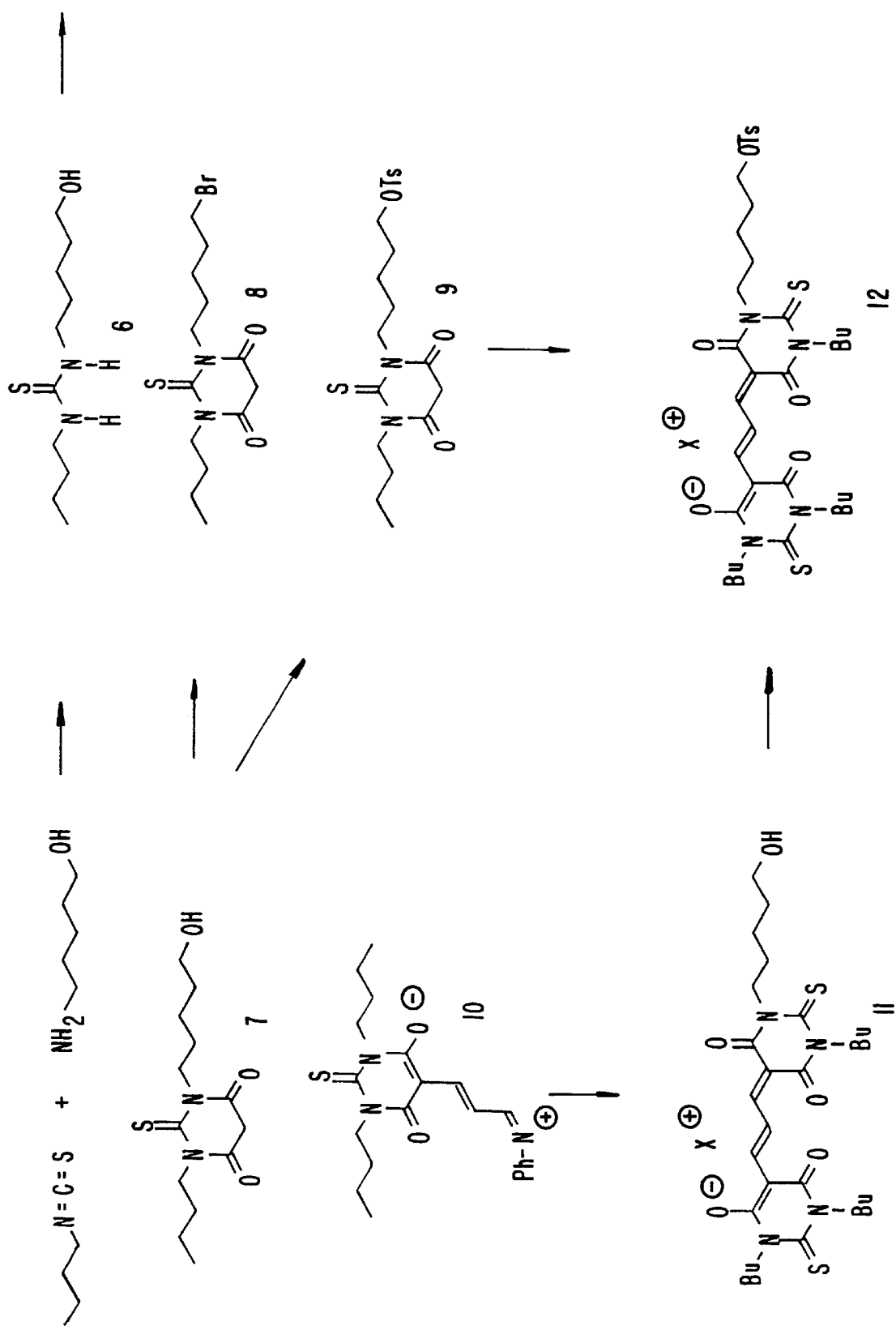
FIGS. 15 and 16 show the synthesis of an asymmetric oxonol with a linker suitable for attachment to a second reagent.
Figure 16:
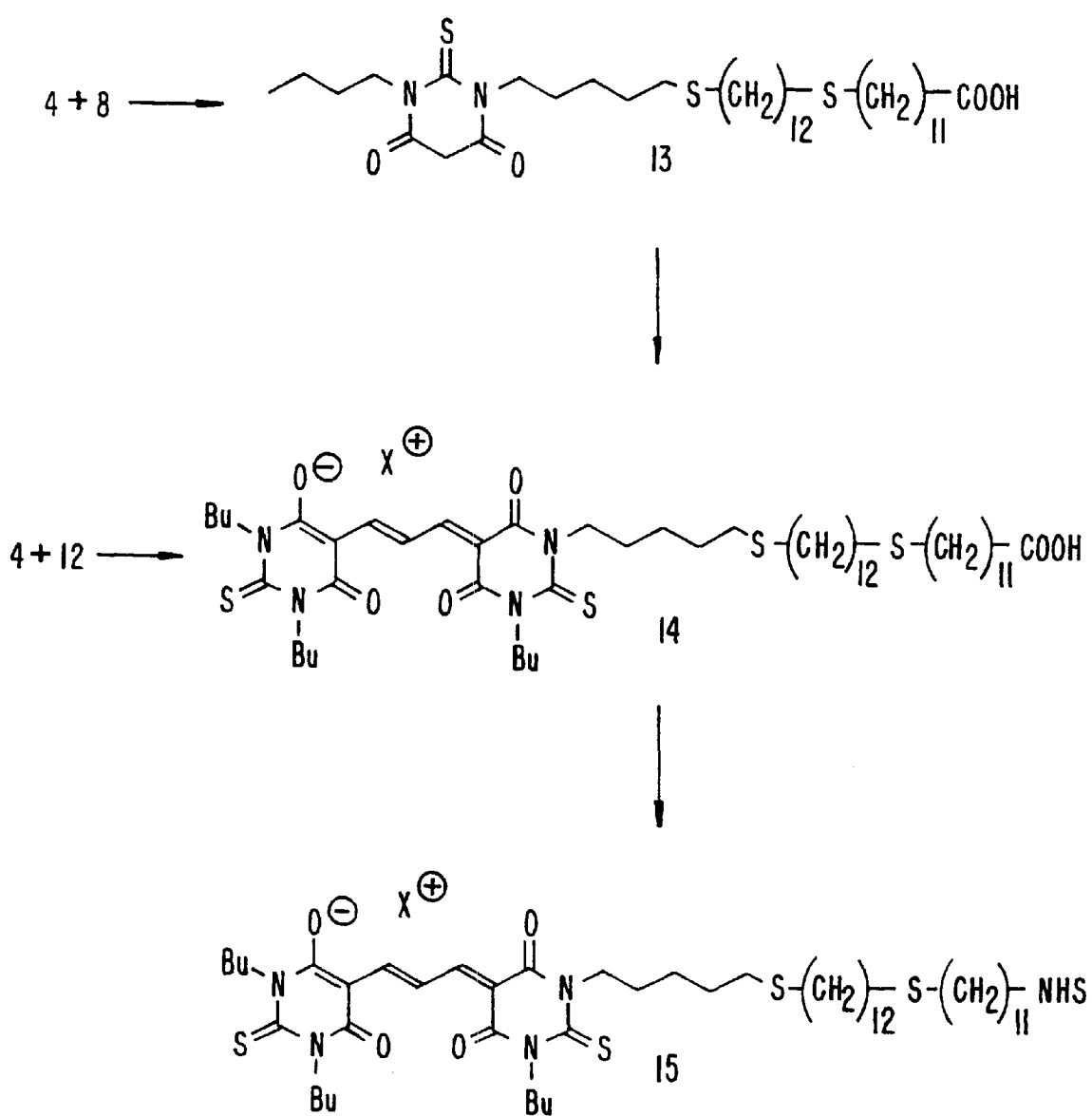

This example is with reference to FIGS. 14–16.

12-p-methoxybenzylthio-1-dodecanol (1):

Na (800 mg, 34.8 mmol) was dissolved in 30 mL of dry MeOH. Under argon, p-methoxybenzylmercaptan (2.75 mL, 3.04 g, 19.7 mmol) was added to the methoxide solution. After a few minutes, 12-bromododecanol (2.5 g, 9.43 mmol) was dropped into the reaction mixture. Within 5 minutes a solid began to come out of solution. After a minimum of 3 h, the reaction was filtered and washed 3× with cold MeOH, yielding 2.874 g (8.49 mmol, 90%) of pure product after drying. $^1$H NMR (CDCl$_3$): d 7.23 (d, J=8.8 Hz, 2H, AA' of AA' BB' aromatic system), 6.85 (d, J=8.8 Hz, 2H, BB' of AA' BB' aromatic system), 3.80 (s, 3H, methoxy), 3.66 (s, 2H, benzyl), 3.64 (dt, J$_1$=6.6 Hz, J$_2$=5.5 Hz, 2H, RCH$_2$OH), 2.40 (t, J=7.3 Hz, 2H, RSCH$_2$R), 1.50–1.65 (cm, 4H, CH$_2$ b to heteroatoms), 1.2–1.4 (cm, 16H, bulk methylenes).

12-p-methoxybenzylthio-1-bromododecane (2):

(1) (500 mg, 1.48 mmol) was mixed with carbon tetrabromide (611 mg, 1.85 mmol) in 2.5 mL CH$_2$Cl$_2$ and cooled in an ice bath until solid began to come out of solution. The ice bath was removed and triphenylphosphine (348 mg, 2.22 mmol) was added to the reaction. The solution immediately turned yellowish. The starting material had been consumed after 30 min according to TLC (EtOAc/Hex, 1:1). The solvent was removed and 50 mL of hexane was added to the solid residue. After stirring overnight, the solution was filtered and concentrated to a solid. The solid was then mixed with about 10–15 mL of hexane and again filtered. The concentrated filtrate yielded 537 mg (1.34 mmol, 91%) of pure product after drying. $^1$H NMR CDCl$_3$): d 7.23 (d, J=8.6 Hz, 2H, AA' of AA' BB' aromatic system), 6.85 (d, J=8.7 Hz, 2H, BB' of AA' BB' aromatic system), 3.80 (s, 3H, methoxy), 3.67 (s, 2H, benzyl), 3.41 (t, J=6.9 Hz, 2H, RCH$_2$Br), 2.40 (t, J=7.3 Hz, 2H, RSCH$_2$R), 1.86 (cm, 2H, CH$_2$ b to Br), 1.15–1.45 (cm, 18H, bulk methylenes).

12-(12-p-methoxybenzylthio-1-dodecylthio)-dodecanoic acid (3):

Na (116 mg, 5 mmol) was dissolved it dry MeOH. 12-mercapto-1-dodecanoic acid (340 mg, 1.46 mmol)-synthesized according to JACS 115, 3458–3474, 1993—was added to the methoxide solution. After stirring with some heating for 5 min, (2) (497 mg, 1.24 mmol) was added to the reaction. The reaction became very viscous and an additional 1.75 mL of MeOH was introduced. The reaction was then left overnight. The reaction was quenched with 10% acetic acid. The paste-like reaction mixture was transferred to a 500 mL separatory funnel dissolved in equal volumes of EtOAc/Hex (1:1) and the acetic acid solution. The organic layer was separated. The aqueous layer was then extracted two more times. The combine extracts were concentrated yielding 740.3 mg (1.34 mmol) of crude product. The excess acetic acid was removed as a toluene azeotrope. The solid was crystallized from isopropyl ether giving 483 mg (71%). TLC and NMR show an impurity believed to be a disulfide side product. The material was further purified by flash chromatography eluting with CHCl$_3$/MeOH/AA (99:0.5:0.5) yielding 334 mg (0.604 mmol, 49%) of pure product. $^1$H NMR (CDCl$_3$): d 9.45 (brs, 1H, COOH), 7.23 (d, J=8.8 Hz, 2H, AA' of AA' BB' aromatic system), 6.85 (d, J=8.7 Hz, 2H, BB' of AA' BB' aromatic system), 3.80 (s, 3H, methoxy), 3.66 (s, 2H, benzyl), 2.50 (t, J=7.3 Hz, 4H, RCH$_2$SCH$_2$R), 2.40 (t, J=7.3 Hz, 2H, RSCH$_2$R), 2.35 (t, J=7.5 Hz, 2H, RCH$_2$COOH), 1.5–1.7 (cm, 8H, CH$_2$ b to heteroatoms), 1.15–1.45 (cm, 30H, bulk methylenes). $^{13}$C NMR (CDCl$_3$): d 179.5 (COOH), 129.9 (aromatic, 2C), 113.9 (aromatic, 2C), 55.2 (MeOR), 35.6 (CH$_2$), 33.7 (CH$_2$), 32.2 (CH$_2$), 31.3 (CH$_2$), 29.7 (CH$_2$), 29.4 (CH$_2$), 29.2 (CH$_2$), 28.9 (CH$_2$), 24.6 (CH$_2$).

1-butyl-3-(12-(12-pentylthio-1-dodecylthio)-dodecanoic Acid) thiobarbiturate (13):

(3) (73.8 mg, 133.5 μmol) was deprotected in 2 mL of dry TFA/anisole (14:1) at 70° C. for 2.5 h. The solvent was removed under vacuum and the residue was dissolved in 10 mL dry EtOH. Sodium borohydride (330 mg) was added and the mixture was stirred overnight. The solution was then acidified with conc. HCL until gas stopped evolving. The solution was then extracted with ether 4×. The combined extracts were concentrated leaving a white solid. The solid was then dissolved and concentrated 2× with degassed MeOH. After drying on the high vacuum, 69.5 mg of solid was recovered. It was estimated by TLC that this solid was 1:1 the deprotected product and di-p-methoxyphenylmethane, (104 μmol, 78%). The deprotected linker was dissolved in 0.5 mL dry DMF, with heating. NaH (~550 μmol) was added which caused some gas evolution. (8) (38.5 mg, ~100 μmol) was then added to the reaction in 100 uL DMF and the reaction was left overnight at 60° C. TLC in EtOAc/MeOH/AA (90:8:2) indicated that a new more non-polar barbituric acid had been formed. The solvent was removed and the residue was dissolved in EtOAc/Hex (1:1) and washed with water. The material was then purified by chromatography, eluting with EtOAc/MeOH/AA (90:8:2). NMR of the product showed resonance from barbituric acid and the linker. Electrospray (neg. ion) MS [MeOH/H$_2$O: 95/5] (peak, rel. int.) 516.4 (95), 699.4 (M-1, 100), 715.1 (M$^{-1}$+16, 40), 1024.0 (M$^{-1}$+32, 25); calc. M$^{-1}$= 700.1 amu. The ether linkers appears to be partially oxidized to sulfoxides.

1-(1,3-dibutyl thiobarbiturate)-3-(1-butyl-3-(12-(12-pentylthio-1-dodecylthio)-dodecanoic Acid) Thiobarbiturate) trimethineoxonol (14):

(3) (73.8 mg, 133.5 mol) was deprotected in 2 mL of dry TFA/anisole (14:1) at 70° C. for 2.5 h. The solvent was removed under vacuum and the residue was dissolved in 20 mL dry EtOH. Sodium borohydride (330 mg) was added and the mixture was stirred overnight. The solution was then acidified with conc. HCL until gas stopped evolving. The solution was then extracted with ether 4×. The combined extracts were concentrated leaving a white solid. The solid was then dissolved and concentrated 2× with degassed MeOH. After drying on the high vacuum, 71.1 mg of solid was recovered. It was estimated by TLC that this solid was 1:1 the deprotected product and di-p-methoxyphenylmethane, (106 μmol, 79%). The deprotected linker was dissolved in 1 mL dry DMF, with heating. NaH (~350 μmol) was added which caused some gas evolution. (12) (35.5 μmol) was then added to the reaction in 200 uL DMF. The reaction did not seem to be proceeding after 1 h, so 4 mg of N.H. (60%) was added to the reaction mixture. The solution now appeared orange instead of red and a second non-polar oxonol began to form. The reaction, heated at 60° C., was allowed to go for 18 h. Half of the reaction mixture was worked up as follows. The reaction mixture was transferred to a 30 mL separatory funnel in ~12 mL toluene. About 4 mL a 10% acetic acid solution and 3 mL of water were added. Most of the oxonol partitioned into the organic layer, which was washed 3× with acetic acid solution/water (1:1). The organic layer was then concentrated and purified by flash chromatography (2.5×18 cm). The column was packed and first eluted with $CHCl_3$/MeOH/ AA (93:5:2). After 1 non-polar oxonol was removed, the solvent polarity was increased to $CHCl_3$/MeOH/AA (90:8:2). This caused the oxonol product to elute off the column. After concentrating the fractions and drying, 7.2 mg pure product (7.25 μmol, 20%) was attained. $^1$H NMR ($CDCl_3$/MeOH): d 8.54 (t, J=13.8 Hz, 1H, central methine), 7.97 (d, J=14.2 Hz, 2H, methines), 4.39 (cm, 8H, $NCH_2R$), 2.46 (t, J=7.3 Hz, 8H, $RCH_2SCH_2R$), 2.2 (t, 2H, $RCH_2COOH$), 1.5–18 (bulk methylenes), 1.2–1.4 (bulk methylenes), 0.92 (t, J=7.2 Hz, 9H, methyls). Electrospray (neg. ion) MS [MeOH/$H_2O$: 95/5] (peak, rel. int.) 683 (50), 977.8 (30), 992.1 ($M^{-1}$, 100), 1008.1 ($M^{-1}$+16, 40), 1024.0 ($M^{-1}$+32, 10); calc. $M^{-1}$=992.5 amu. The +16 and +32 peaks suggest oxidation of thioethers to sulfoxide groups. (14) has also been successfully synthesized from (13) using (10) in a similar fashion as that described in the synthesis of (11).

1-(1,3-dibutyl thiobarbiturate)-3-(1-butyl-3-(12-(12-pentylthio-1-dodecylthio)-N-hydroxysuccinimide dodecanoate)thiobarbiturate)trimethineoxonol (15):

22.5 μmol of (14) was reacted with disuccinimidyl carbonate (57 mg, 225 mol) in 0.5 mL $CH_2Cl_2$ in the presence of DIEA (39 uL, 225 mmol). After 1.5 hours, TLC (EtOAc/ MeOH) (9:1) indicated that 3 new non-polar bands had been formed. The solvent was removed and two non-polar oxonol bands were purfied by flash chromatagraphy, eluting with (EtOAc/MeOH) (95:5). Electrospray (neg. ion) MS [MeOH/ $H_2O$: 95/5] (peak, rel. int.) 1089.3 ($M^{-1}$, 20), 1105.1 ($M^{-1}$+ 16, 100), 1121.0 ($M^{-1}$+32, 60); calc. $M^{-1}$=1089.5 amu.

Example IV

Measurement of Membrane Potential with Oxonol Dyes as Fret Acceptors and Fluorescent Lectins as Fret Donors FL-WGA was purchased from Sigma Chemical Co. (St. Louis, Mo.). TR-WGA was prepared from WGA and Texas Red (Molecular Probes; Eugene, Oreg.) in a 100 mM bicine buffer at pH 8.5. A 73 μM solution of WGA was reacted with a 6-fold excess of Texas Red for 1 h at room temperature. The protein conjugate was purified on a G-25 Sephadex column.

All cells were grown and handled like L-M(TK$^-$) except where noted. L-M(TK$^-$) cells were grown in Dulbecco's Modified Eagle Media (Gibco; Grand Island, N.Y.) with 10% fetal bovine serum (FBS) and 1% penicillin streptomycin (PS) (Gemini; Calabasas, Calif.). B104 cells were differentiated with 1 μM retinoic acid for 5 days prior to use. The cells were plated on glass coverslips at least one day before use. The adherent cells were washed and maintained in 2.5–3.0 mL of HBSS with 1 g/L glucose and 20 mM HEPES at pH 7.4. A freshly prepared 75 μM aqueous solution of the appropriate oxonol was made prior to an experiment from a DMSO stock solution. The cells were stained by mixing 100 μL of the oxonol solution with 750 μL of the bath and then adding the diluted solution to the cells. The dye was left for 30–40 minutes at a bath concentration of 2.3 μM. 1.5 mM B-cyclodextrin in the bath solution was necessary for cell loading of DiSBA-$C_6$-(3). The butyl and ethyl derivatives were water-soluble enough to load cells with out B-cyclodextrin complexation. DiSBA-$C_{10}$-(3) was loaded in a pH 7.4 solution containing 290 mM sucrose and 10 mM HEPES, 364 mOsm, for 10 min at a bath concentration of 10 μM. DiSBA-$C_{10}$-(3) labeling was quenched by replacing the bath with HBSS solution. The cells were stained with 15 μg/mL of FL-WGA for 15 minutes. The B104 cells required a 125 μg/mL bath concentration to give satisfactory lectin staining. The excess dyes were removed with repeated washes with HBSS. If the excess ethyl or butyl oxonol derivatives were left in the bath, slow currents and fluorescence changes due to redistribution of the dyes into the cell were observed during depolarizations greater than 1 s. The cardiac myocytes [Henderson, S. A., Spencer, M., Sen, A., Kumar, C., Siddiqui, M. A. Q., and Chien, K. R. 1989. Structure organization, and expression of the rat cardiac myosin light chain-2 gene. *J. Biol. Chem.* 264:18142–18146] were a gift of Professor Kenneth Chien, UCSD. The Jurkat lymphocyte suspensions were grown in RPMI media with 5% heat inactivated FBS and 1% PS. 15–20 mL aliquots; of the cellular suspension were washed three times before and after dye staining by centrifugation at 100× g for 4 minutes followed by additions of fresh HBSS.

The fluorescently labeled cells were excited with light from a 75 W xenon lamp passed through 450–490 nm excitation interference filters. The light was reflected onto the sample using a 505 nm dichroic. The emitted light was collected with a 63X Zeiss (1.25 or 1.4 numerical aperture) lens, passed through a 505 nm long pass filter and directed to a G-1B 550 nm dichroic (Omega; Brattleboro, Vt.). The reflected light from this second dichroic was passed through a 515 DF35 bandpass filter and made up the FL-WGA signal. The transmitted light was passed through a 560 or 570 LP filter and comprised the oxonol signal. For experiments using the oxonol as a donor to TR-WGA, the 550 nm dichroic was used for excitation and a 580 nm dichroic was used to split the emission. The long wavelength Texas Red fluorescence was passed through a 605 nm DF55 bandpass filter. Voltage dependent fluorescence changes in single cells were measured using a Nikon microscope attached to a Photoscan II photometer equipped with two R928 PMTs for dual emission recordings. A 7-point Savitsky-Golay smoothing routine was applied to all optical data [Savitsky, A. and Golay, M. J. E. 1964. Smoothing and differentiation of data by simplified least squares procedure. *Anal. Chem.* 36:1627–1639], unless otherwise noted. The 1–2 KHz single wavelength data was acquired with an Axobasic program that used the TTL pulse counting routine LEVOKE. Confocal images were acquired using a home built high speed confocal microscope [Tsien, R. Y. and B. J. Bacskai. 1994. Video-rate confocal microscopy. In Handbook of Biological Confocal Microscopy. J. B. Pawley, editor. Plenum Press, New York]. The cell was voltage-clamped at a holding potential of −70 mV. After a 200 ms delay, the cell was given a 200 ms depolarizing square voltage pulse to 50 mV. Pseudocolor images showing the ratio of the Fl-WGA to oxonol emissions were collected every 67 ms and clearly showed a change in ratio, localized to the plasma membrane, upon depolarization of the cell to +50 mV.

Patch clamp recording were made using an Axopatch 1-D amplifier equipped with a CV-4 headstage from Axon Instruments (Foster City, Calif.). The data were digitized and stored using the PCLAMP software. The pH 7.4 intracellular solution used contained 125 mM potassium gluconate, 1 mM $CaCl_2 \cdot 2H_2O$, 2 mM $MgCl_2 \cdot 6H_2O$, 11 mM EGTA, and 10 mM HEPES. For the B104 cells, 4 mM ATP and 0.5 mM GTP were added.

The quantum yield of DiSBA-$C_6$-(3) was determined relative to rhodamine B in ethanol ($_F$=0.97) [Weber, G. and Teale, F. W. K. 1957. Determination of the absolute quantum yield of fluorescent solutions. *Faraday Soc. Trans.* 53:646–655]. $R_o$ was calculated following standard procedures [Wu, P. and Brand, L. 1994. Resonance energy transfer: methods and applications. *Anal. Biochem.* 218:1–13]. The spectra of FL-WGA in HBSS and DiSBA-C$_6$-(3) in octanol were used to determine the overlap integral. Values of 1.4 and 0.67 were used for the index of refraction and orientation factor respectively.

Figure 2:
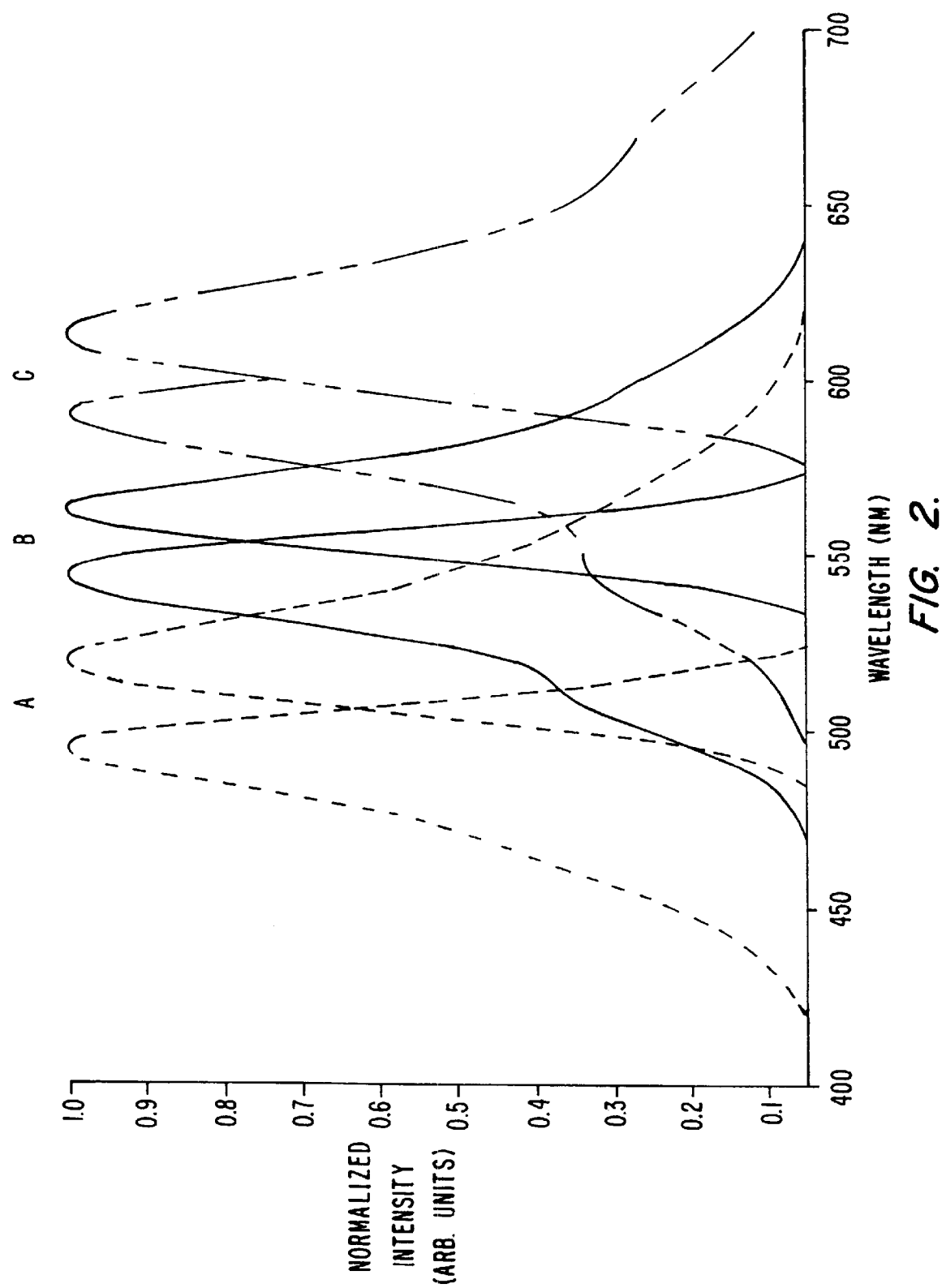
FIG. 2 illustrates normalized excitation and emission spectra for (A) fluorescein-labeled wheat germ agglutinin (FL-WGA) in Hanks Balanced Salt Solution (HBSS), (B) (1,3-dihexyl-2-thiobarbiturate)trimethine oxonol [DiSBA-$C_6$-(3)] in octanol, and (C) TR-WGA in HBSS.

Symmetrical bis(thiobarbiturate)oxonols were chosen as likely candidates for rapidly translocating fluorescent ions based on the above design criteria. The strong absorbance maximum ($\sim$200,000 M$^{-1}$ cm$^{-1}$) at 540 nm and good quantum yield (0.40) in membranes makes them desirable for use as a fluorescence donors or acceptors in cells. The fluorescence excitation and emission spectra of DiSBA-C$_6$-(3) is shown in FIG. 2 along with those for FL-WGA and TR-WGA. The excitation spectra are the shorter of each pair. Octanol was selected as the oxonol solvent in order to mimic the membrane environment.

The translocation rates were studied in L-M(TK$^-$) cells using whole-cell voltage clamp recording. The L-M(TK$^-$) cells were chosen because they have very low background currents and are easy to patch clamp. These cells have a resting potential of –5 mV and no evident voltage activated currents.

Figure 3:
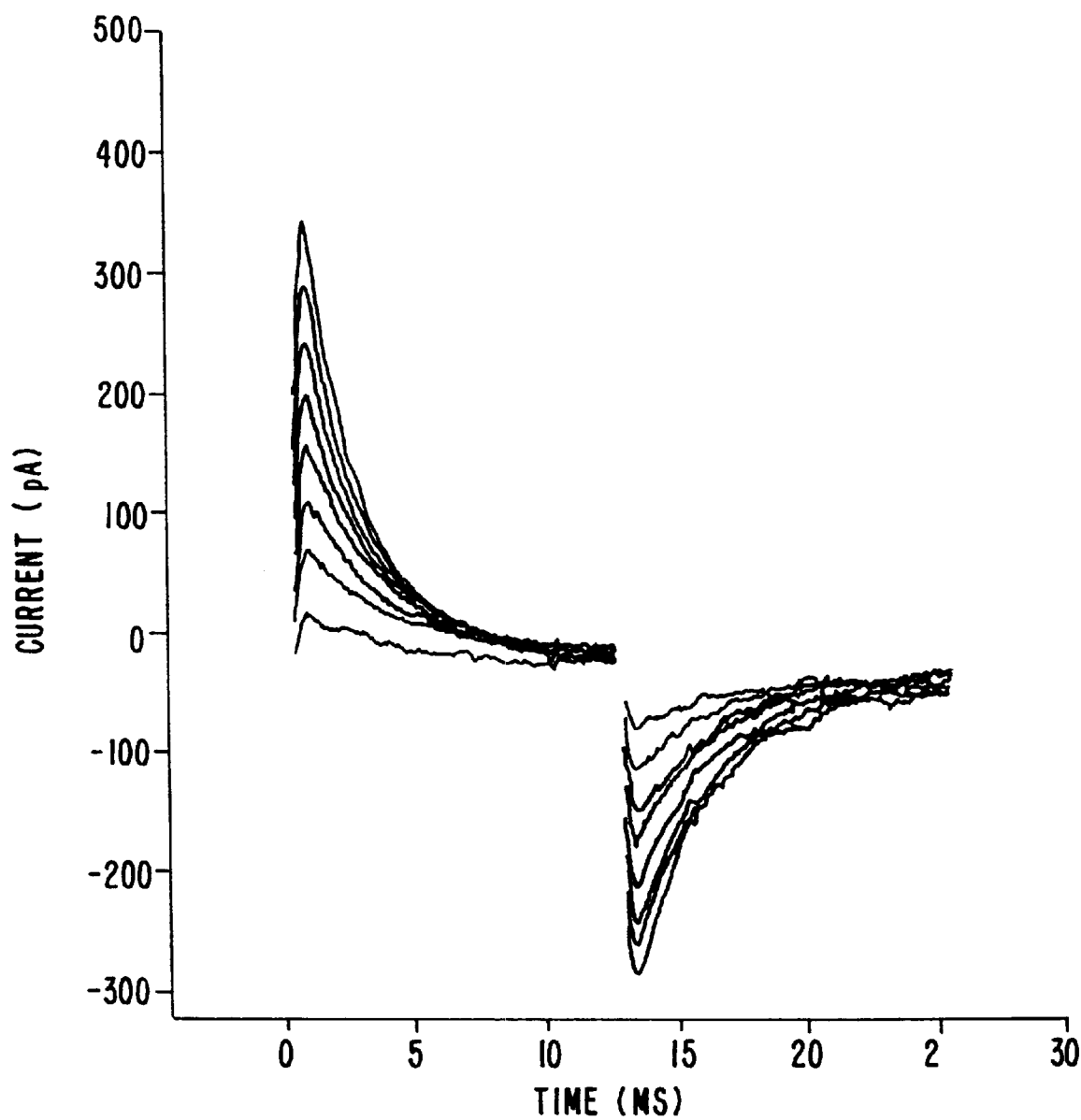
FIG. 3 illustrates displacement currents of 2.3 μM DiSBA-$C_6$-(3) in L-M(TK$^-$) cells at 20° C.

Displacement currents from DiSBA-C$_6$-(3) at 20° C. are displayed in FIG. 3. 12.5 ms long voltage steps at 15 mV increments were applied to the cell, from a holding potential of –70 mV. The larger, faster transients due to simple membrane capacitance transient could be minimized using the capacitance and series resistance compensation capabilities of the Axopatch amplifier, allowing the displacement currents to be clearly observed. The currents are due to redistribution of the membrane-bound oxonol in response to 8 depolarizations. The time constant for the displacement current is 2 ms for 120 mV depolarization. Equal amounts of charge move at the onset and conclusion of the voltage step, but in opposite directions, consistent with redistribution of stored ions from one energy minimum to the other across the plasma membrane. Furthermore, the induced capacitance dq/dV from the oxonol movement is calculated to be $\sim$5 pF for 100 mV depolarization. This value corresponds to roughly one third the membrane capacitance without the dye. Interestingly, sodium channel gating charges are also responsible for about 33% of the total capacitance of squid axons for small depolarizations [Hodgkin, A. 1975. The optimum density of sodium channels in an unmyelinated nerve. *Philos. Trans. R. Soc. Lond.* [*Biol*] 270:297–300]. Negligible currents were observed in the absence of the oxonol. DiSBA-C$_{10}$-(3) gave displacement currents of approximately the same speed, whereas analogues with R=butyl and ethyl gave much slower currents. The butyl compound had a time constant of $\sim$18 ms and the currents from the ethyl compound were very small, slow, and difficult to observe.

Figure 4:
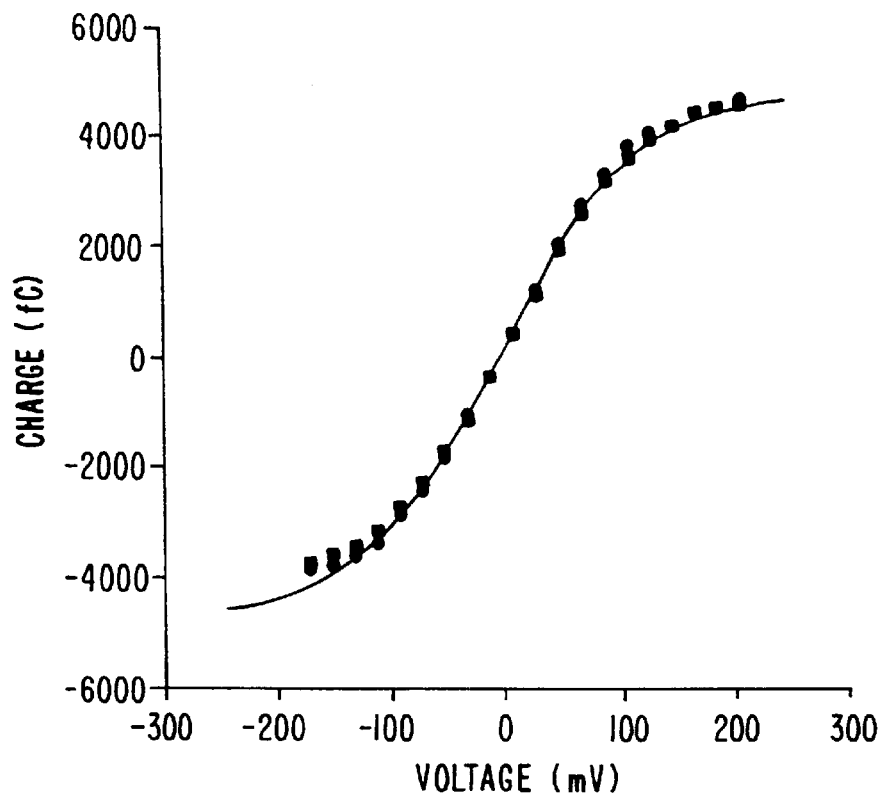
FIG. 4 illustrates voltage dependence of DiSBA-C6-(3) moved during the displacement and tailcurrents for step voltage changes from a −30 mV holding potential.

FIGS. 4 and 5 show the voltage dependence and time constants for charge translocation in a cell loaded with about 4 times as much oxonol as in the experiment of FIG. 3. In FIG. 4, the circles are the data from the on response and the squares from the tail currents. The raw data were fit to a single exponential and the charge moved, the area, was calculated as the product of the current amplitude and the time constant. The experimental data are in reasonable accord with existing models of hydrophobic ion transport between two energy minima near the aqueous interfaces of the lipid bilayer [Ketterer, B., Neumcke, B., and Läuger, P. 1971. Transport mechanism of hydrophobic ions through lipid bilayer membranes. *J. Membrane Biol.* 5:225–245; Andersen, O. S. and Fuchs, M. 1975. Potential energy barriers to ion transport within lipid bilayer. *Biophys. J.* 15:795–830; Benz, R., Läuger, P., and Janko, K. 1976. Transport kinetics of hydrophobic ions in lipid bilayer membranes. *Biochim. Biophys. Acta* 455:701–720]. These models predict that the equilibrium charge displacement q(V) and the translocation time constant (V) should depend on the externally applied membrane potential V in the following manner:

$$\Delta q(V) = \Delta q_{\max} \tanh\left[\frac{q\beta(V - V_h)}{2kT}\right] \quad (1)$$

$$\tau(V) = \tau_{\max} \mathrm{sech}\left[\frac{q\beta(V - V_h)}{2kT}\right] \quad (2)$$

$V_h$, the membrane potential at which there are equal numbers of ions in each potential energy well, could differ from zero because of membrane asymmetry. $\beta$ is the fraction of the externally applied potential effectively felt by the translocating ion; q is the charge on each ion, k and T are Boltzmann's constant and absolute temperature. $q_{max}$ and $\tau_{max}$ are respectively the total charge in each energy well and the time constant for translocation, both at V=$V_h$. The smooth curve in FIG. 4 is the fit to Eq. 1 with $q_{max}$=4770±140 fC, $\beta$=0.42±0.02, and $V_h$=–3.8±1.5 mV. Likewise the smooth curve in FIG. 5 is the fit to Eq. 2 with $\tau_{max}$=2.9 ms at $V_h$=–5 mV and $\beta$=0.42.

These results demonstrate that the oxonol senses a significant part of the electric field across the membrane, that it translocates in $\sim$3 ms or less, and that the greatest sensitivity and linearity of translocation as a function of membrane potential is in the physiologically relevant range.

To transduce charge displacements into optical signals, the oxonol fluorescences at the intracellular and extracellular membrane binding sites is made different. Fluorescence asymmetry is created with the introduction of fluorescently labeled lectins bound to the extracellular membrane surface. Excitation of FL-WGA leads to energy transfer to oxonols located in the extracellular membrane binding site as shown in FIG. 1. The extinction coefficient and the fluorescence quantum yield of FL-WGA were measured to be 222,000 M$^{-1}$ cm$^{-1}$ ($\sim$3 fluorescein/protein) and 0.23, respectively. In Jurkat cell suspensions labeled with FL-WGA, up to 30% of the lectin fluorescence intensity was quenched upon titration of DiSBA-C$_4$-(3). In the best case where all of the quenching is due to energy transfer, the average distance from the lectin to the membrane-bound oxonol is still greater than 50 Å, the calculated Förster distance $R_o$ for the FL-WGA/oxonol pair. The spectral overlap between the FL-WGA emission and DiSBA-C$_6$-(3) excitation is given in FIG. 2. Because FRET falls off with the inverse sixth power of the distance separating the two fluorophores, energy transfer to oxonols in the intracellular membrane site, an additional 40 Å away, is probably negligible.

Figure 6:
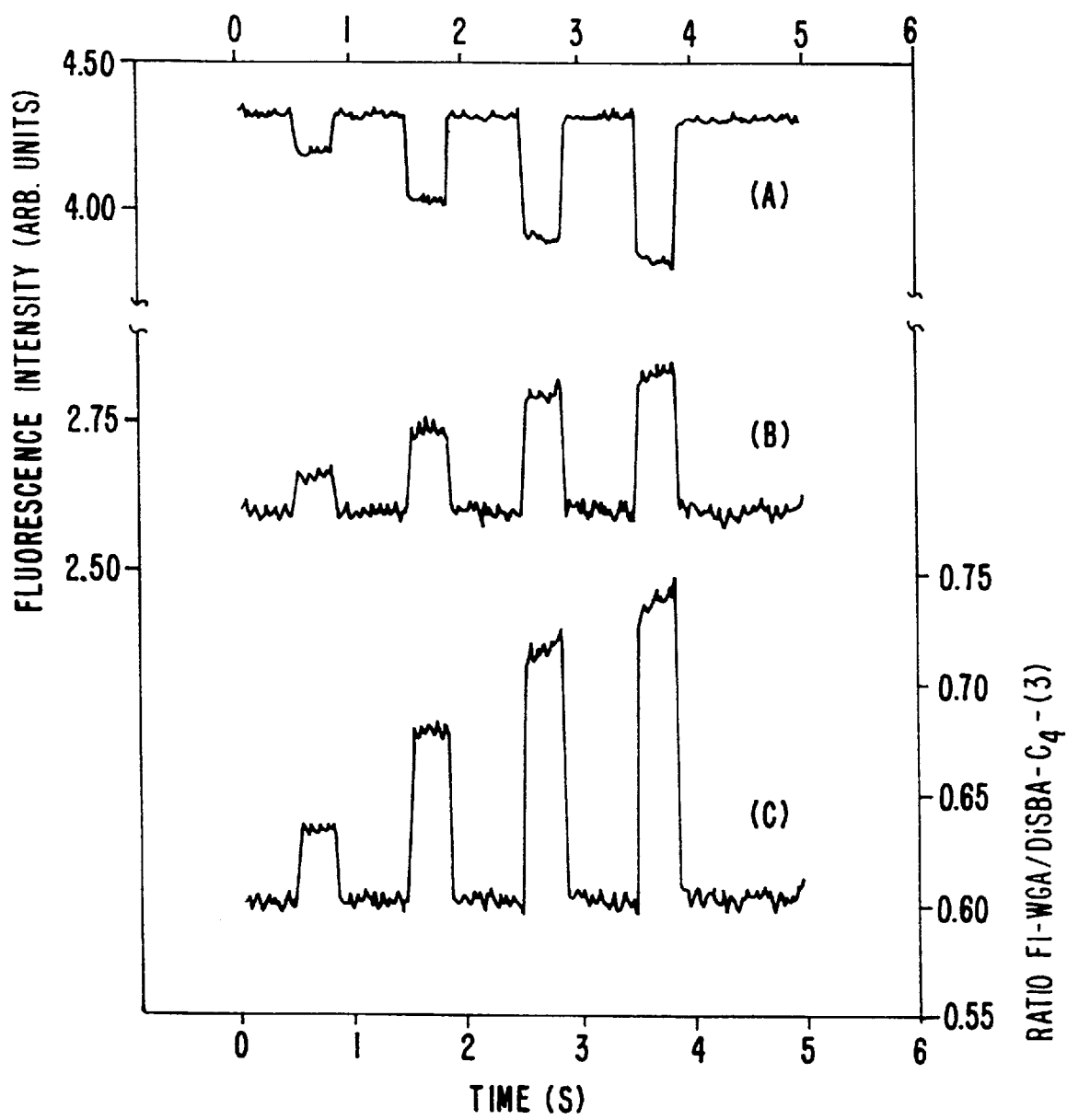
FIG. 6 illustrates simultaneous fluorescence changes of the FL-WGA/DiSBA-$C_4$-(3) pair in response to 4 depolarizations from −70 mV of 40, 80, 120, and 160 mV in a L-M(TK$^-$) cell at 20° C., with the single wavelength fluorescence emission traces of DiSBA-$C_4$-(3) and FL-WGA being shown in panels A and B, respectively, and the FL-WGA/DiSBA-$C_4$-(3) ratio displayed in (C)

Upon depolarization, the oxonol molecules redistribute such that more are bound to the intracellular site and less to the extracellular one. This change manifests itself with a decrease in the energy transfer, resulting in an increase in the fluorescence of the FL-WGA and a concomitant decrease in the oxonol emission. The fluorescence signals in a voltage clamped L-M(TK$^-$) cell labeled with (the DiSBA-C$_4$-(3)/FL-WGA pair) and depolarized with four increasing voltage steps are shown in FIG. 6. The data are the average of 29 sweeps. The FL-WGA emission increases 7–8%, the oxonol fluorescence decreases 10% and the FL-WGA/oxonol emission ratio changes 19% for a 120 mV depolarization. The simultaneous changes in donor and acceptor emissions is consistent with the FRET mechanism outlined in FIG. 1. The decrease in oxonol emission with depolarization is opposite to what is observed for the slow voltage-sensitive uptake of oxonols in cells [Rink et al. 1980, supra]. The fluorescence changes have time constants of ~18 ms at 20° C., in agreement with the DiSBA-$C_4$-(3) displacement currents. No large fluorescence changes are observed in the absence of FL-WGA. The translocation rate of DiSBA-$C_4$-(3) speeds up with increasing temperature. The time constant falls to 7–8 ms at 29° C., corresponding to an activation energy of ~17 kcal/mol. However, raising the temperature also increases internalization of the lectin and eventually decreases the fluorescence change. The oxonols with R=ethyl and butyl also reach internal cellular membranes, though active membrane internalization is probably not necessary. Additional dilution of the voltage-dependent FRET signals arises from spectral overlap of the fluorescein and oxonol, such that some of the light in the fluorescein emission channel comes from the oxonol and vice versa.

Figure 7:
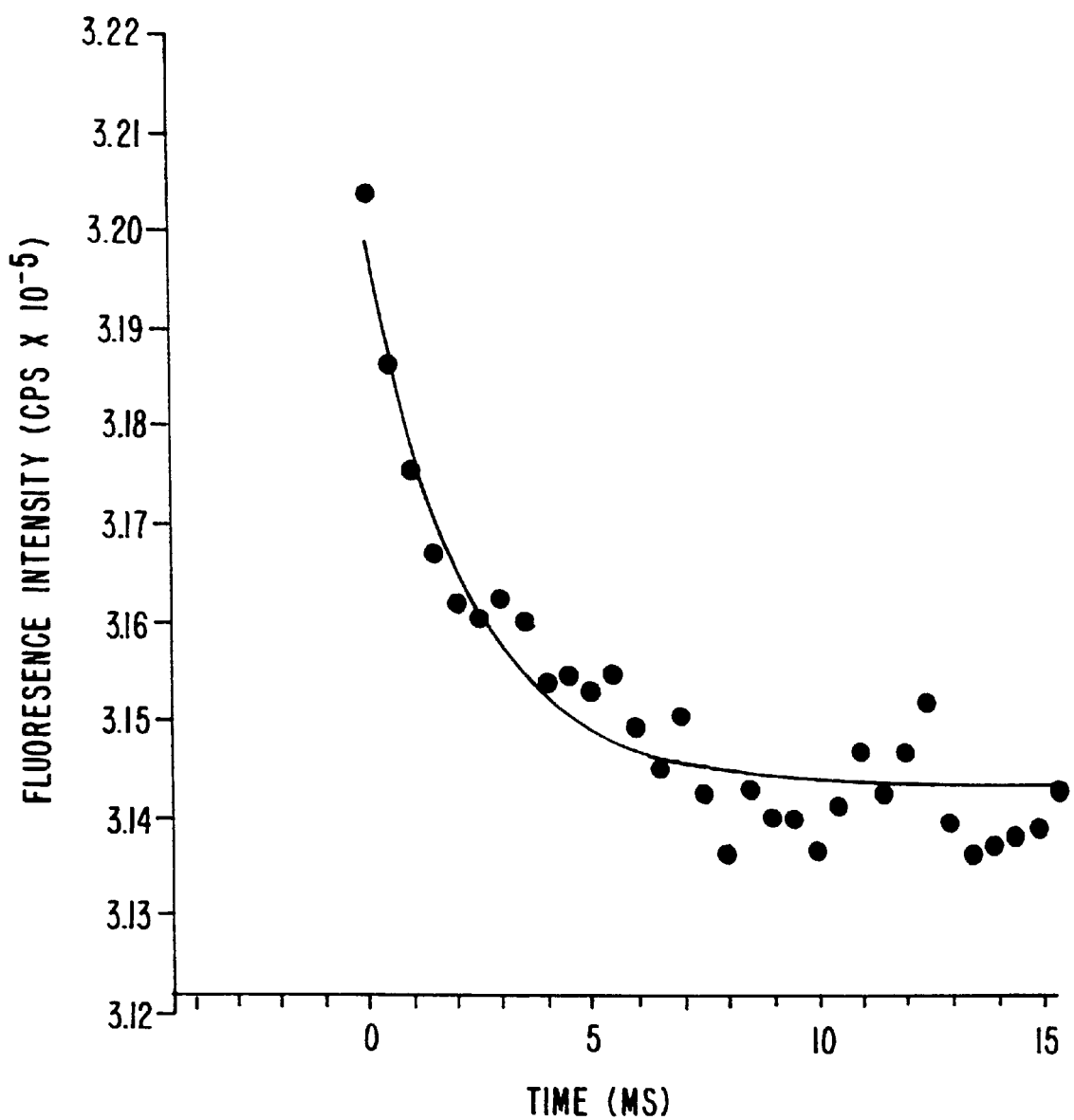
FIG. 7 illustrates the time course of the fluorescence change of the FL-WGA/DiSBA-$C_{10}$-(3)pair in response to a 100 mV depolarization from −70 mV.

Increasing the length of the alkyl chains on the oxonol improves the response times significantly. The DiSBA-$C_6$-(3)/FL-WGA pair, has a time constant of ~3 ms at 20° C., while the DiSBA-$C_{10}$-(3)/FL-WGA pair, responds with a time constant of 2 ms, as shown in FIG. 7. The solid curve is a fit to a single exponential with a 2 ms time constant. The data is the average of 3 L-M(TK$^-$) cells, at 20° C., acquired at 2 kHz. The response in the figure is slightly slower than the true value because of smoothing. The fluorescence time constants are in agreement with those from the displacement currents, for example in FIG. 3. The beneficial effect of adding hydrophobicity to the oxonol in the form of longer alkyl chains reaches a plateau. There is a large 6-fold increase in translocation rate substituting hexyl for butyl on the oxonol core. However, addition of twice as many methylene groups in going from the hexyl to the decyl compound results in less than a 2-fold increase. These faster translocating oxonols are essentially insoluble in water and require modified procedures to load into cells. DiSBA-$C_6$-(3) is easily loaded in normal medium supplemented with 1.5 mM β-cyclodextrin to complex the alkyl chains. Nonfluorescent DiSBA-$C_6$-(3) aggregates in Hanks Balanced Salt Solution (HBSS) become fluorescent upon addition of β-cyclodextrin. DiSBA-$C_{10}$-(3) requires loading in a medium of low ionic strength with osmolarity maintained with sucrose. Labeling is confined almost exclusively to the plasma membrane, presumably because the hydrophobicity is now great enough to prevent desorption from the first membrane the dye encounters.

Example V

Figure 17:
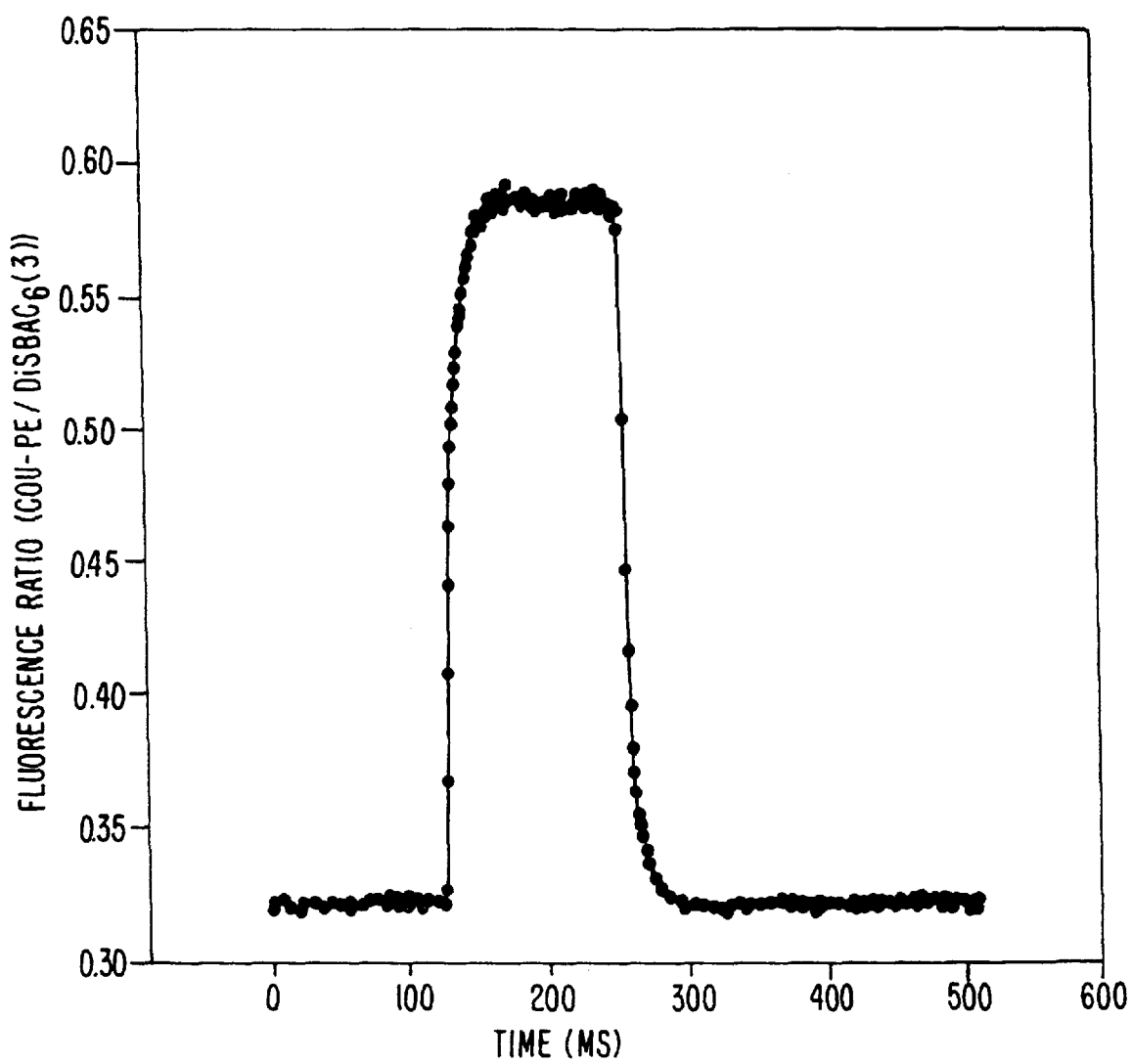
FIG. 17 shows FRET between Cou-PE, a conjugate of a 6-chloro-7-hydroxycoumarin to dimyristoylphosphatidylethanolamine, as FRET donor, to a bis-(1,3-dihexyl-2-thiobarbiturate)-trimethineoxonol in an astrocytoma cell.
Figure 18:
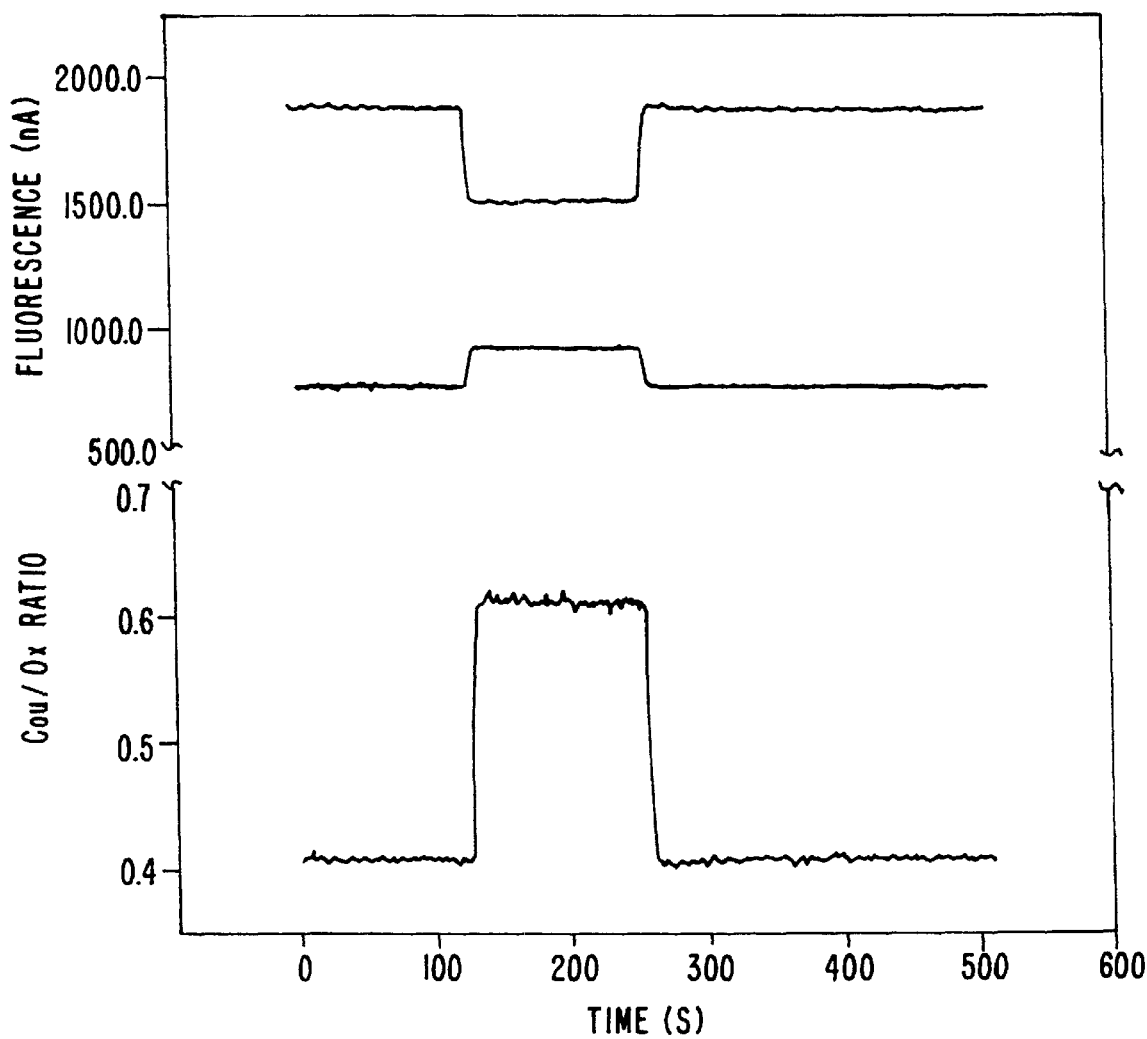
FIG. 18 shows FRET between DMPE-glycine-coumarin (Cou-PE) as FRET donor to a bis-(1,3-dihexyl-2-thiobarbiturate)-trimethineoxonol in L-cells.
Figure 19:
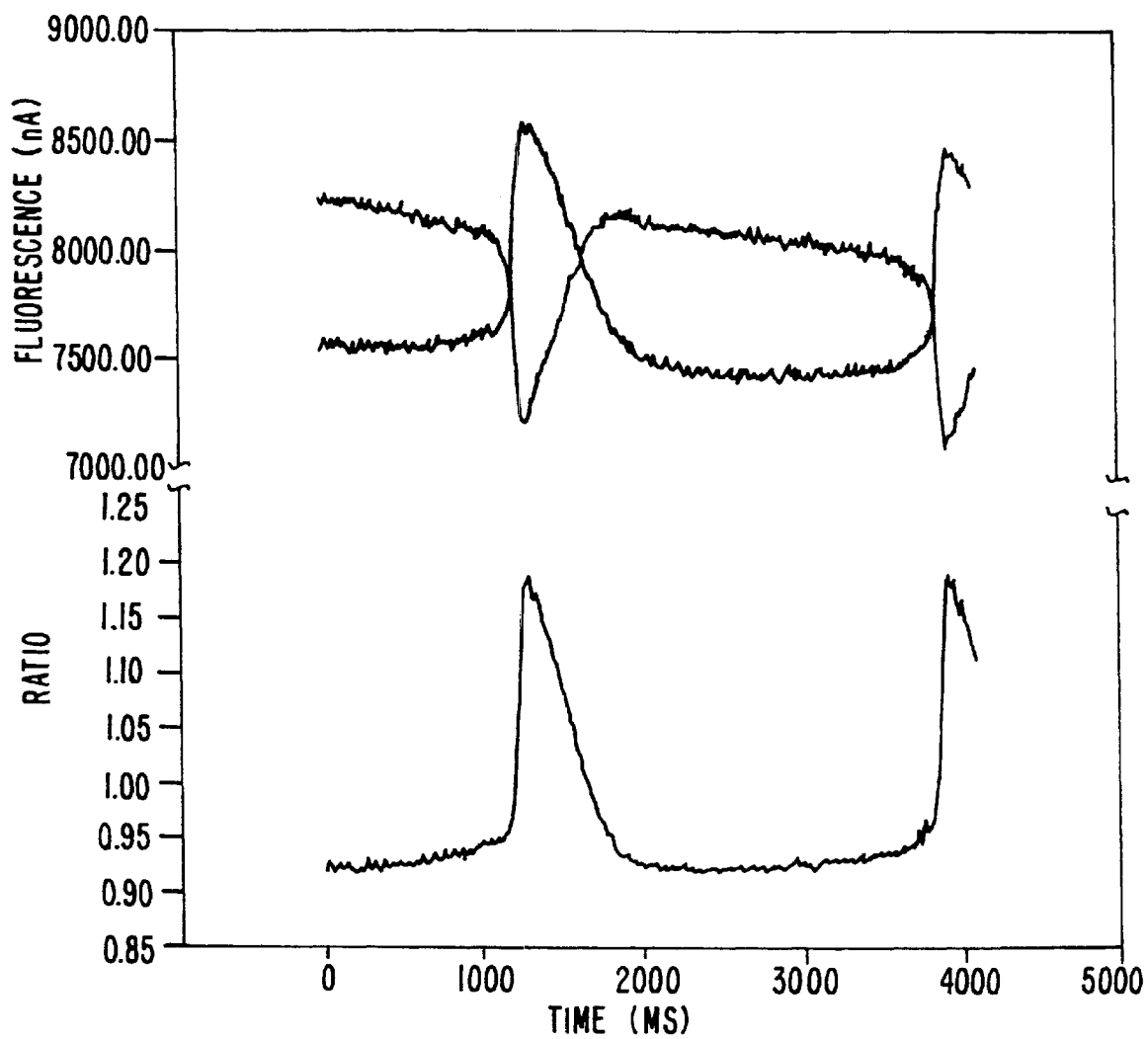
FIG. 19 shows FRET between DMPE-glycine-coumarin (Cou-PE); as FRET donor to a bis-(1,3-dihexyl-2-thiobarbiturate)-trimethineoxonol in cardiomyocytes measured by ratio ouput.

Measurement of Membrane Potential with Oxonol Dyes as Fret Acceptors and Fluorescent Lipid Fret Donors A. Trimethine Oxonols A 6-chloro-7-hydroxycoumarin conjugated to dimyristoylphosphatidylethanolamine (DMPE) via a glycine linker, Cou-PE, has been prepared and found to function as a excellent voltage-sensitive FRET donor to bis-(1,3-dialkyl-2-thiobarbiturate)-trimethineoxonols. This new FRET pair has given an 80% ratio change for a 100 mV depolarization in an astrocytoma cell, which is the largest voltage-sensitive optical signal observed in a cell, FIG. 17. The voltage sensitivity of this FRET pair is consistently 2–3 times better than Fl-WGA/trimethineoxonol in a variety of cell types. In L-cells, ratio values between 25–50% are found, with equal percent changes found in both channels, FIG. 18. In neonatal cardiomyocytes, 5–30% fluorescence ratio changes were observed for spontaneously generated action potentials. The largest signals are almost 4 times larger than those possible with Fl-WGA/trimethineoxonol. An example of such a large change from a single cluster of heart cells is given in FIG. 19. The benefits of a ratio output are evident in the figure. The individual wavelengths, at the top of the figure, show a decreasing baseline that is due to fluorophore bleaching. The ratio data shown on the bottom of the figure compensates for the loss of intensity in both channels and results in a flat baseline. Furthermore, motion artificially causes broadening of the individual wavelength responses. The ratio data reduces these artifacts and results in a sharper signal that more closely represents the actual voltage changes. The greater sensitivity for this new FRET pair is most likely due to a combination of factors. Moving the donor closer to the membrane surface and decreasing the Forster transfer distance, $R_o$, may result in increased FRET discrimination between the mobile ions on the same and opposite sides of the membrane. Also, the increased spectral separation facilitates collection of the donor and acceptor emission and reduces signal loss due to crosstalk.

B. Pentamethine Oxonols

Bis-(1,3-dialkyl-2-thiobarbiturate)-pentamethineoxonols have been prepared by condensing 1,3 substituted thiobarbituric acids with glutacondialdehyde dianil monohydrochloride, also known as N-[5-(phenylamino)-2,4-pentadienylidene]benzenamine monohydrochloride. The pentamethine oxonols absorb at 638 nm (e =225,000 M$^{-1}$ cm$^{-1}$) and fluoresce maximally at 663 nm in ethanol. The absorbance and emission are shifted 100 nm to longer wavelengths, compared to the trimethine oxonols. This shift is consistent with other polymethine dyes, such as cyanines, where addition of 2 additional methine units results in 100 nm wavelengths shifts to the red.

The pentamethines can be loaded into cells in culture in the same manner as the trimethine oxonol. The butyl compound, DiSBAC$_4$(5), can be loaded in Hanks' Balanced Salt Solution, while the hexyl compound, DiSBAC$_6$(5), requires addition of beta-cyclodextrin to mask the hexyl side chains and solubilize the hydrophobic oxonol.

Voltage-sensitive FRET from various plasma membrane-bound fluorescent donors to the pentamethine oxonols have been demonstrated in single cells. Fl-WGA has been shown to undergo FRET with the pentamethine and give ratio changes comparable to those observed for the trimethine oxonol. In astrocytoma cells, ratio changes of 15–30% were recorded for a 100 mV depolarization step from −70 mV. Apparently, the decrease in FRET due to the reduced overlap integral, J, on moving the oxonol absorbance 100 nm longer is compensated by increased selectivity of FRET to the extracellular face of the membrane relative to the intracellular one and/or decreased spectral overlap.

Figure 20:
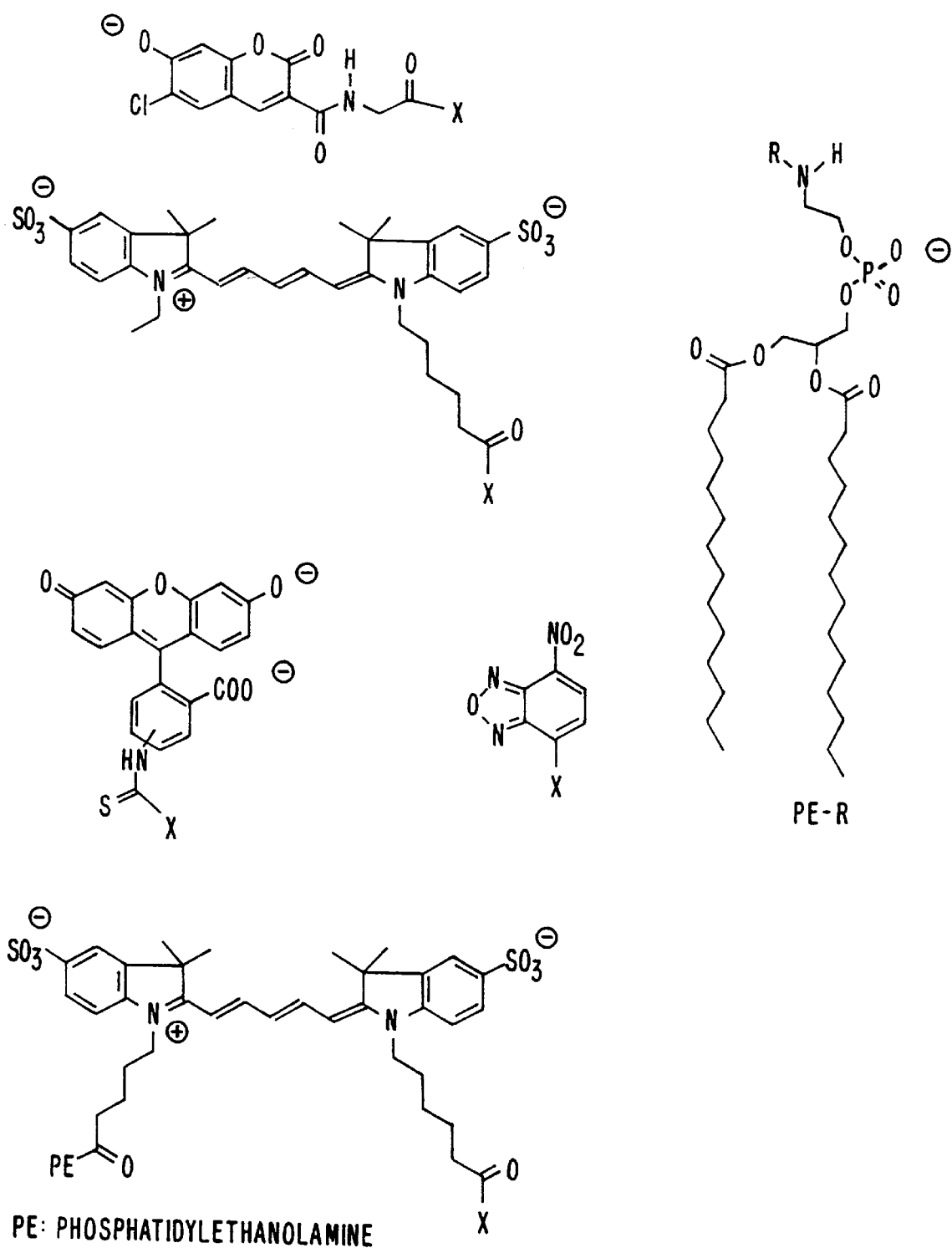
FIG. 20 shows representative fluorescent phosphatidylethanolamine conjugates that function as FRET donors to the oxonols. The structures on the left depict representative fluorophores and X denotes the site of attachment of the phosphatidylethanolamine (PE). The structure (PE-R) on the right shows a phosphatidylethanolamine where R denotes a fluorophore attached to the amine of the ethanolamine.
Figure 21:
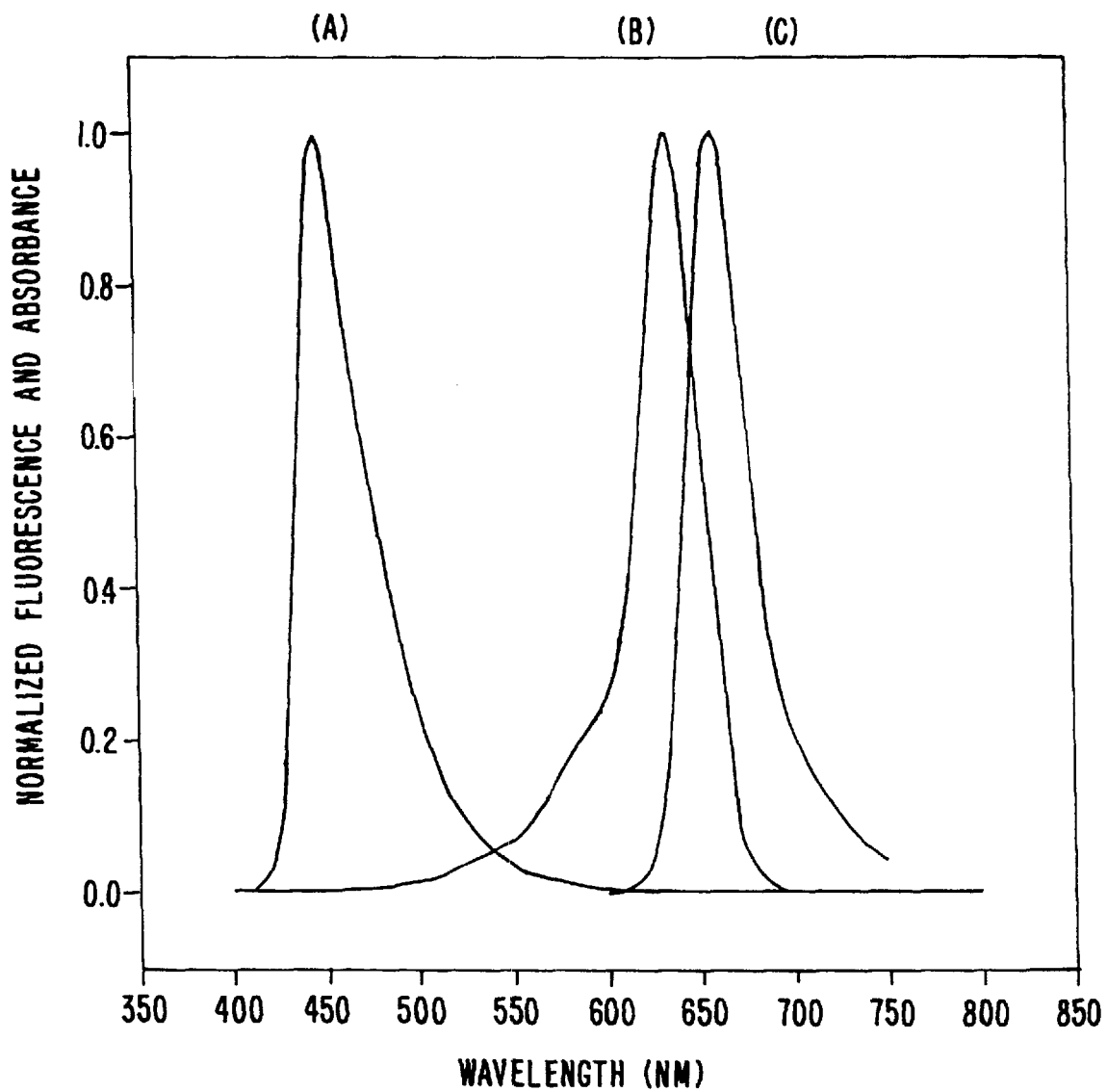
FIG. 21 shows (A) emission spectrum of the Cou-PE; (B) the excitation spectrum of DiSBA-$C_6$-(5); and (C) the emission spectrum of DiSBA-$C_6$-(5).

Fluorescent phosphatidylethanolamine conjugates have also been found to function as FRET donors to the pentamethine oxonol. The structures of PE conjugates tested are shown in FIG. 20. NBD-PE/pentamethineoxonol pair has given 1–10% ratio changes per 100 mV. Cou-PE/pentamethineoxonol has given 15–30% ratio changes in voltage clamped astrocytomas for 100 mV depolarization. This pair is remarkable because the Cou-PE emission and DiSBAC$_6$(5) absorbance maxima are separated by 213 nm and there is hardly any visible overlap, FIG. 21. The large extinction at long wavelengths of the pentamethine enable FRET between the coumarin and the pentamethine oxonol.

The Ro for this pair has been calculated to be 37 Å, using a quantum yield value of 1.0 for the Cou-PE.

Figure 22A:
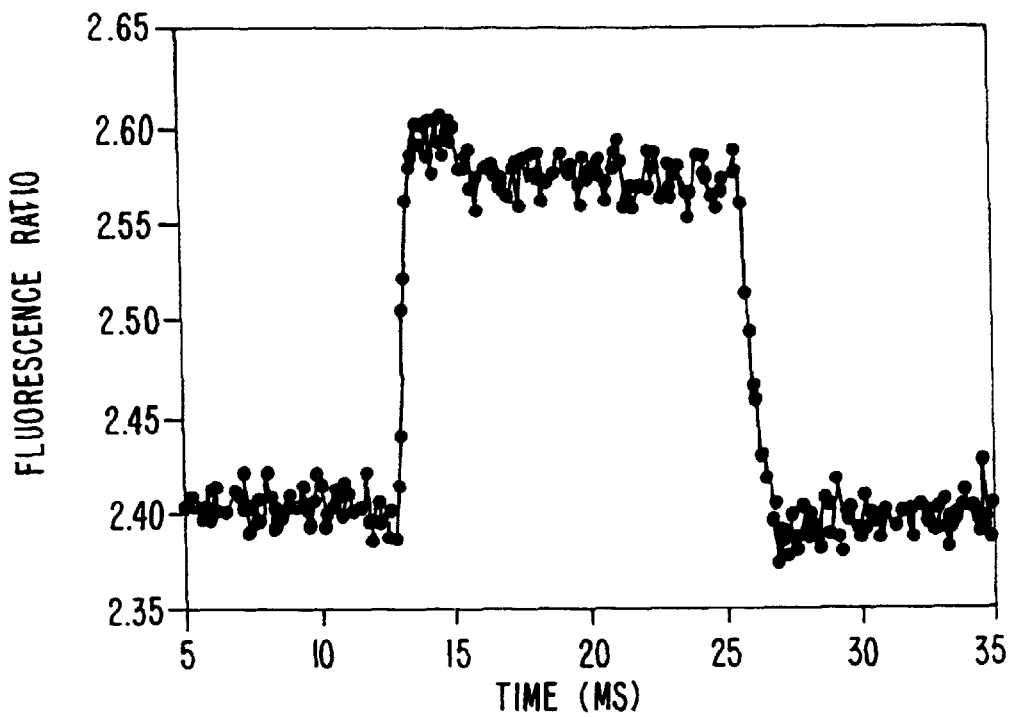
FIGS. 22A and 22B show the speed of DiSBA-$C_6$(5) translocation in response to a 100 mV depolarization step, using FRET from asymmetrically labeled Cou-PE.
Figure 22B:
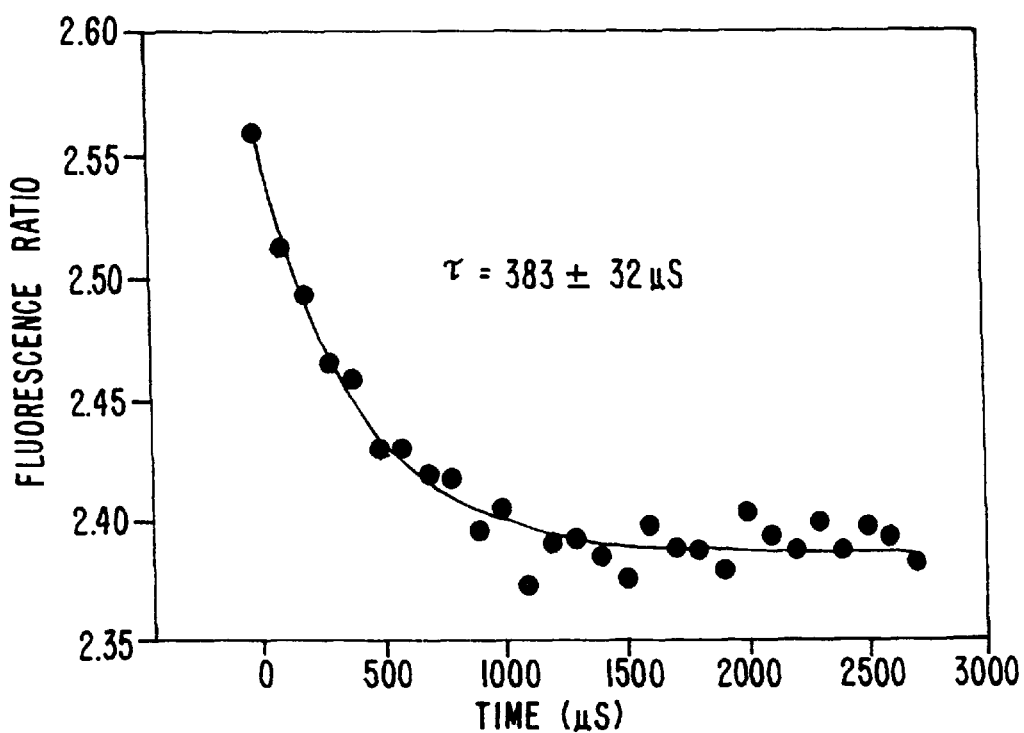
Figure 23A:
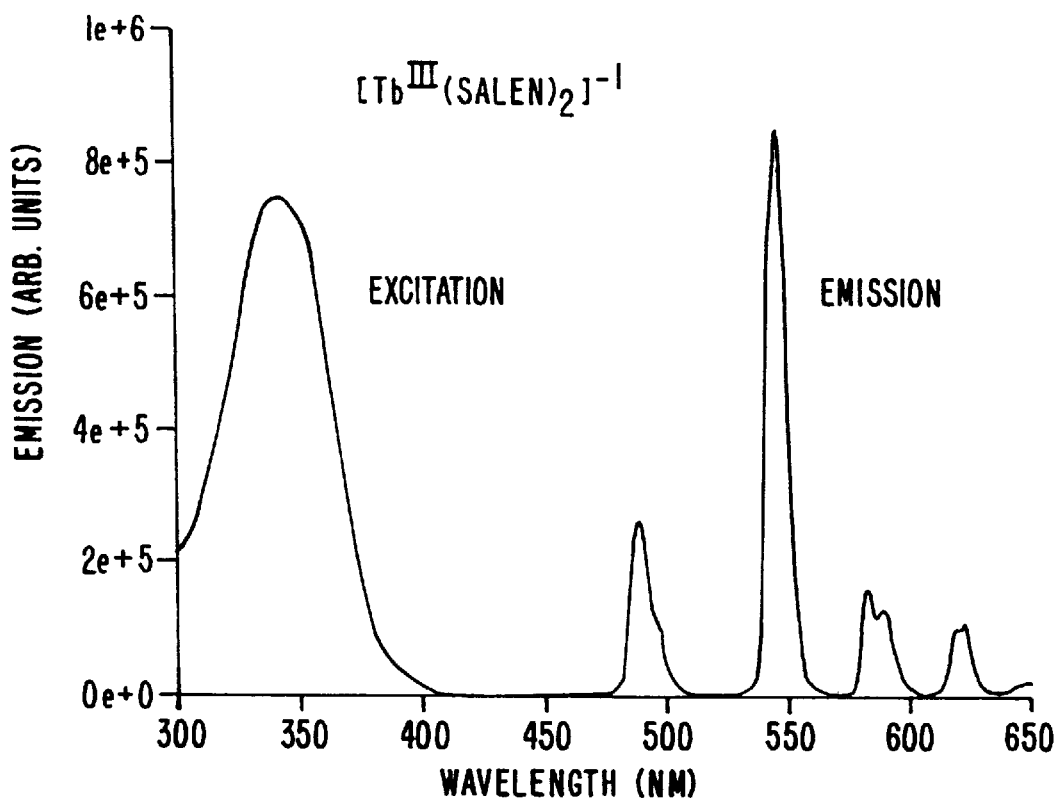
FIGS. 23A and 23B show the spectra of $[Tb(Salen)_2]^{-1}$ (top) and $[Eu(Salen)_2]^{-1}$ (bottom), both as piperidinium salts dissolved in acetonitrile.
Figure 23B:
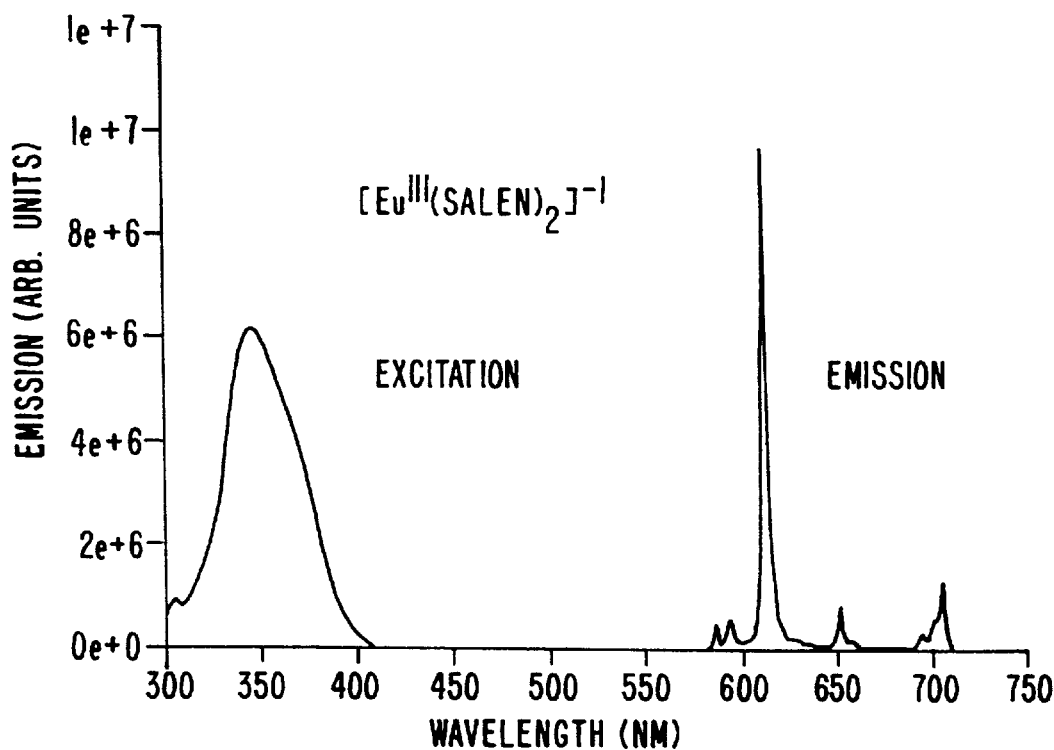

The membrane translocation rates for the pentamethines are 5–8 times faster than the trimethine analogues. DiSBAC$_4$(5) displacement currents in voltage-clamped astrocytoma cells showed that butyl pentamethine oxonol jumps across the plasma membrane with a time constant of ~2 ms in response to voltage steps of +20–120 mV. The trimethine analogue translocates ~18 ms under identical conditions. The displacement currents of DiSBAC$_6$(5) decay very rapidly and are difficult to separate from the cell capacitance. As a result of the large voltage-dependent signal from the Cou-PE/DiSBAC$_6$(5) pair, it was possible to optically measure the speed of voltage response of DiSBAC$_6$(5). The time constant for DiSBAC$_6$(5) translocation was measured optically at 0.383±0.032 ms in response to a 100 mV depolarization step, using FRET from asymmetrically labeled Cou-PE. The ratio data and the exponential response are shown in FIG. 22. The enhanced translocation rates result from the greater charge delocalization and slightly more hydrophobicity of the pentamethine oxonols. The rapid voltage response of DiSBAC$_6$(5) is the fastest known for a permeant, highly fluorescent molecule. The submillisecond response is fast enough to accurately register action potentials of single neurons.

Example VI

Measurement of Membrane Potential with Oxonol Dyes as Fret Donors

The direction of energy transfer can be reversed using TR-WGA instead of FL-WGA. DiSBA-C$_6$-(3) functions as a FRET donor to TR-WGA in L-M(TK$^-$) cells with the same response time as FL-WGA/DiSBA-C$_6$-(3). The spectral overlap of this FRET pair is shown in FIG. 2. The signal change, however, is only one half that for FL-WGA/DiSBA-C$_6$-(3).

DiSBAC$_6$(3) has been successfully used as a FRET donor to Cy5 labeled PE, in B104 neuroblastoma cells. The ratio changes of 5–15%/100 mV are the largest observed with the mobile ion being the donor.

Example VII

Measurement of Membrane Potentials in Different Cell Types

Figure 8:
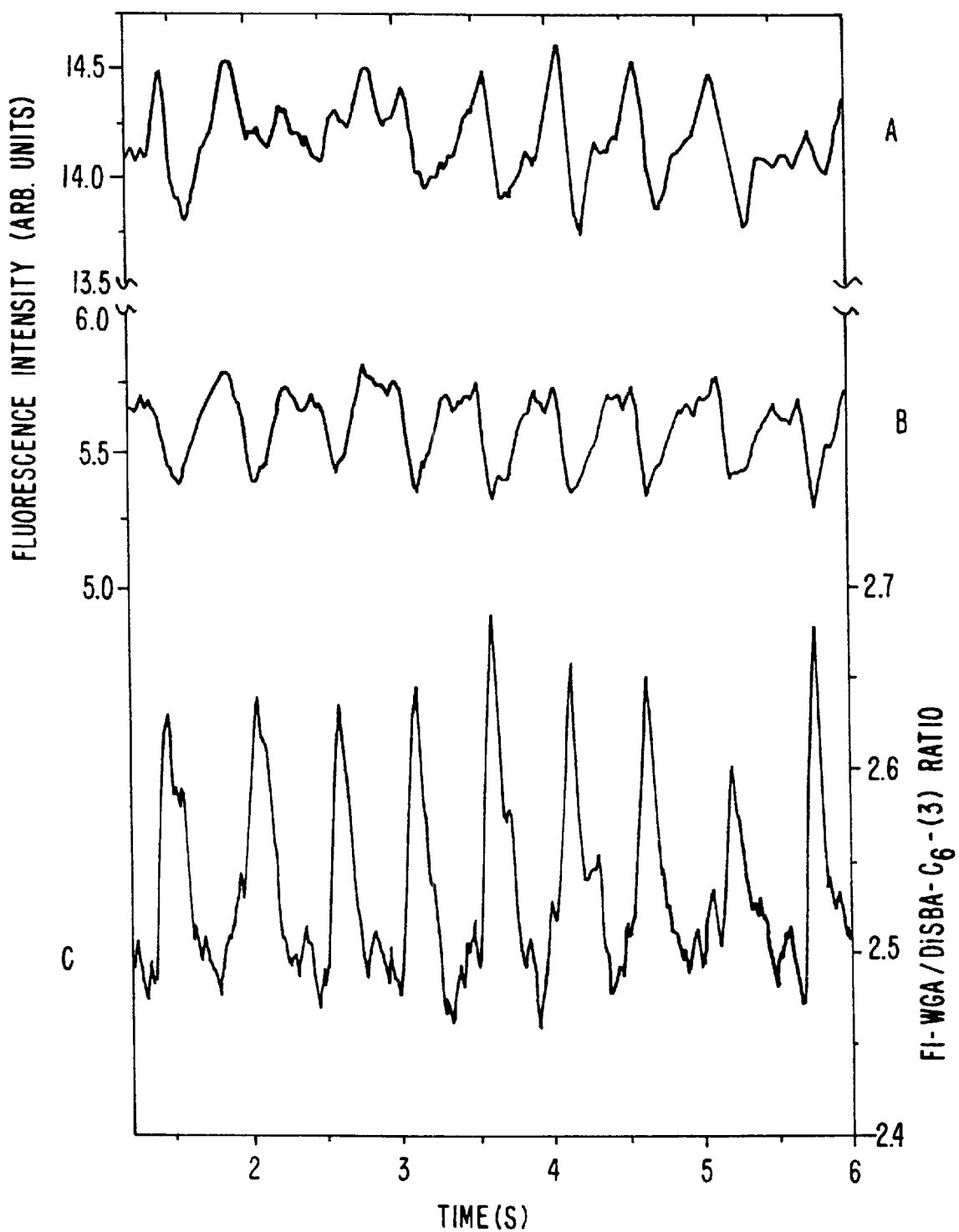
FIG. 8 illustrates a single sweep trace of fluorescence ratio changes from the FL-WGA/DiSBA-$C_4$-(3) pair in beating neonatal cardiac myocytes, with the top trace (A) showing the FL-WGA channel, (B) the longer wavelength oxonol channel and (C) the FL-WGA/oxonol ratio, in which motion artifacts are significantly reduced.

The FL-WGA/DiSBA-C$_6$-(3) system was tested in a variety of cell lines. In neonatal cardiac myocytes, the two fluorophores could be loaded without affecting the spontaneous beating. Therefore, the added capacitance from the oxonol displacement current did not prevent generation of action potentials. The periodic 90 mV action potentials [Conforti, L., Tohse, N., and Sperelakis, N. 1991. Influence of sympathetic innervation on the membrane electrical properties of neonatal rat cardiomyocytes in culture. J. Devel. Physiol. 15:237–246] could be observed in a single sweep, FIG. 8C. The ratio change without subtraction of any background fluorescence was 4–8%. Motion artifacts were observed in the single wavelength data. In FIGS. 8A and B, large slow changes in the detected light were observed in both channels. Satisfyingly, these effects were essentially eliminated in the ratio data. The data were acquired at 100 Hz and 10 µM of isoproterenol was added to the bath solution. The voltage dependent fluorescence changes are faster than the mechanically based artifacts, as expected [Hill, B. C. and Courtney, K. R. 1982. Voltage-sensitive dyes discerning contraction and electrical signals in myocardium. Biophys. J. 40:255–257]. Some cells, loaded with oxonol at 2.3 µM, did stop beating after about 7 seconds of continuous exposure to the xenon arc illumination. At 0.6 µM loading, the phototoxicity and unfortunately the signal were reduced. In differentiated B104 neuroblastoma cells an 8% ratio increase was recorded, without any background subtraction, for a 120 mV depolarization. The inward sodium currents did not deteriorate from phototoxic effects during experiments with excitation exposures totaling 10–20 s. FL-WGA/DiSBA-C$_6$-(3) labeled 1321N astrocytoma cells showed oxonol and FL-WGA fluorescence almost exclusively on the plasma membrane.

Figure 9:
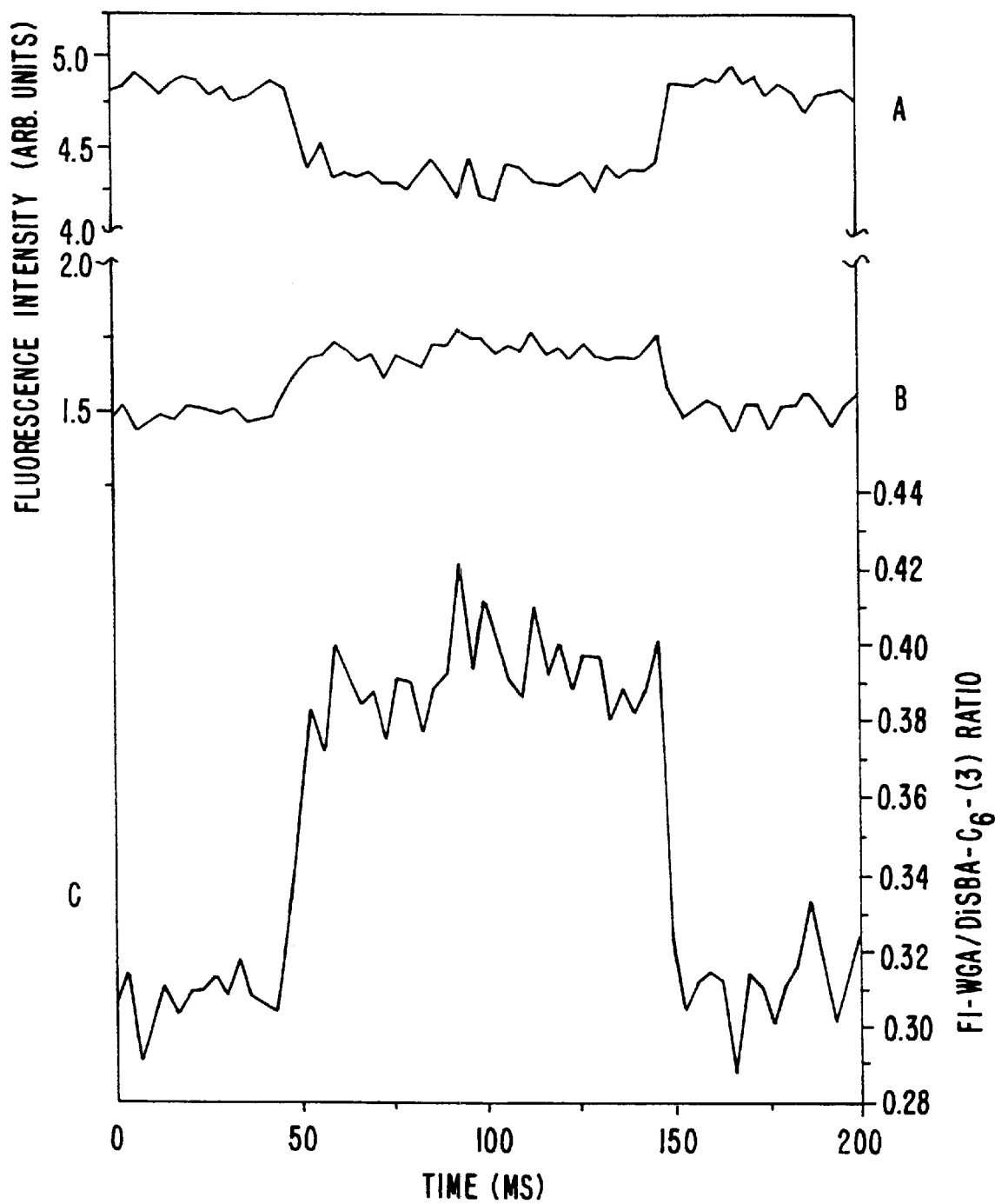
FIG. 9 illustrates the fluorescence changes of the FL-WGA/DiSBA-$C_6$-(3) pair in a voltage clamped astrocytoma cell, the top trace (A) being the DiSBA-$C_6$-(3) emission, (B) the FL-WGA fluorescence signal and (C) the FL-WGA/oxonol ratio.

Ratio changes of 22–34% for 100 mV were observed in photometry experiments such as FIG. 9. After a 50 ms delay, the membrane potential was depolarized 100 mV from −70 mV for 100 ms. The traces are the average of 4 sweeps acquired at 300 Hz, with no smoothing. The time constant for the fluorescence changes is less than 3.3 ms consistent with the displacement currents, such as those in FIG. 3. A small background signal was subtracted from the starting signal, <5% for the oxonol channel and <15% for the fluorescein channel. The fluorescence intensities in the fluorescein and oxonol channels increased ~17% and decreased ~16% respectively for 100 mV depolarization. In these cells, unlike the L-M(TK$^-$), the crosstalk between emission channels was decreased and larger changes occurred in the fluorescein signal. These signal changes are the largest millisecond membrane potential dependent ratio changes observed in single cells. Previous investigations have shown that 4-ANEPPS gives a 9%/100 mV excitation ratio change [Montana, V., Farkas, D. L., and Loew, L. M. 1989. Dual-wavelength ratiometric fluorescence measurements of membrane potential. Biochemistry 28:4536–4539]. In addition, FL-WGA/DiSBA-C$_6$-(3) fluorescence changes in each emission channel are comparable to the largest reported changes, for example, the 21%/100 mV change in a neuroblastoma using RH-421 [Grinvald, A., Fine, A., Farber, I. C., and Hildesheim, R. 1983. Fluorescence monitoring of electrical responses from small neurons and their processes. Biophys. J. 42:195–198]. The large signals from FL-WGA/DiSBA-C$_6$-(3) made it possible to record ratio images of membrane potential changes in voltage clamped L-M(TK$^-$) and astrocytoma cells; using a high speed confocal microscope.

The astrocytoma cells gave a 10–20% ratio increase that was localized to the plasma membrane for a 120 mV depolarization.

Example VIII

Synthesis of Fluorescent Tetraaryl Borates

With reference to FIG. 10, in a 25 mL flame dried two neck flask 0.788 g (580 µL, 2.2 mmol) of compound I was dissolved in 6 mL of dry hexane under argon. After cooling the flask to −70 C, 1.46 mL of a 1.5 M n-butyllithium solution (2.2 mmol) was added via syringe. In a separate flask 0.60 dry borane II was dissolved in a deoxygenated mixture of 6 mL hexane and 1.5 mL of freshly distilled THF. The borane solution was then added via syringe to the lithium reagent. A solid immediately precipitated. After 30 min the cold bath was removed and the reaction was allowed to slowly heat up. Three hours later the solvent was decanted off and the solid rinsed with more hexane. The solid was dissolved in acetonitrile and water and then poured into a separatory funnel. The aqueous layer was again washed with hexane and then extracted with ethyl acetate. Half of the extract was concentrated yielding 124.9 mg (170.5 μmol) of the desired product. This product was then mixed with 97 mg of tetrabutylammonium fluoride in acetonitrile for 15 min at room temperature. After workup 129.1 mg of compound III as the tetrabutylammonium salt was recovered (93%). $^1$HNMR (d$_6$ acetone) 7.61 (br d, 2H, CF$_3$-phenyl group), 7.43 (cm, ~3H, CF$_3$-phenyl group), 6.90–7.26 (cm, ~7H, CF$_3$-phenyl group), 3.43 (cm, 8H, NC$\underline{H}_2$CH$_2$CH$_2$CH$_3$), 1.81 (cm, ~8H, NCH$_2$C$\underline{H}_2$CH$_2$CH$_3$), 1.42 (cm, ~8H, NCH$_2$CH$_2$C$\underline{H}_2$CH$_3$), 0.93 (t, J=7.1 Hz, NCH$_2$CH$_2$CH$_2$ C$\underline{H}_3$).

With reference to FIG. 10, for synthesis of compound IV, in a 5 mL round bottom flask 14 mg (17.2 umol) of compound III, 7 mg (25.8 umol) of bromomethylbimane, 27.3 mg (172 umol) of potassium carbonate, and 5 mg (18.9 umol) of 18-crown-6 were mixed in 0.6 mL of dry acetonitrile. The mixture was heated at 70 C 1.5 h. After cooling, the reaction mixture was dissolved in ethyl acetate and washed 3× with water. The organic residue was purified by flash chromatography eluting with toluene/acetone (2:1). The major band was collected yielding 12.1 mg (70%) of pure product IV tetrabutyl ammonium salt. $^1$HNMR (d$_6$ acetone) 7.58 (br d, 2H, CF$_3$-phenyl group), 7.4–7.5 (cm, 2H, CF$_3$-phenyl group), 7.0–7.3 (cm, $^{18}$10H, CF$_3$-phenyl group), 5.29 (d, J=1.6 Hz, 2H, CH$_2$), 3.46 (cm, 8H, NC $\underline{H}_2$CH$_2$CH$_2$CH$_3$), 2.56 (d, J=0.7 Hz, 3H, bimane methyl), 1.84 (cm, ~8H, NCH$_2$C$\underline{H}_2$CH$_2$CH$_3$), 1.79 (d, J=0.8 Hz, 3H, bimane methyl), 1.76 (s, 3H, bimane methyl), 1.44 (cm, ~8H, NCH$_2$CH$_2$ C$\underline{H}_2$CH$_3$), 0.98 (t, J=7.2 Hz, NCH$_2$CH$_2$CH$_2$C$\underline{H}_3$); $f$=0.73 in dioxane based on quinine sulfate in 0.1 N H$_2$SO$_4$ $f$=0.55.

Example IX

Synthesis of Asymmetric Oxonols with a Linker Group (A) This example illustrates the synthesis of asymmetric oxonols containing a built-in linker group. With reference to FIG. 11, for synthesis of compound V, 4.35 g (21.7 mmol) of 1,12-diaminododecane was dissolved in 40 mL of dry CH$_2$Cl$_2$. Via syringe, 2.62 mL (2.17 mmol) of butyl isothiocyanate was added to the reaction flask. A white solid had precipitated after 15 minutes. One hour after the addition, the reaction mixture was filtered. The filtrate was then evaporated leaving a white solid. The solid was redissolved in 45 mL of dry CH$_2$Cl$_2$ and mixed with 2.44 mL of N,N-diisopropylethylamine (DIEA) and 3.9 g (17.9 mmol) of di-tert-butyl dicarbonate. After reacting for 1 hour, the mixture was poured into a separatory funnel and washed with 5% sodium bicarbonate. A solid came out of solution and was filtered away (<100 mg). The organic solution was then washed with water and a saturated brine solution. The organic layer was then dried with MgSO$_4$ and filtered. The filtrate was evaporated leaving a white solid, which was recrystallized in isopropyl ether yielding 4.30 g (10.3 mmol) of pure compound V (48% overall). $^1$HNMR (CDCl$_3$) 5.73 (br s, 2H, thioamide), 4.50 (br s, 1H, carbamate), 3.40 (br s, 4H, NC$\underline{H}_2$), 3.10 (q, J=7.2 Hz, ~3H, C$\underline{H}_2$ next to carbamate), 1.44 (s, 9H, t-butyl), 1.2–1.7 (cm, bulk C$\underline{H}_2$ s), 0.94 (t, J=7.2 Hz, n-butyl methyl).

For preparing compound VI, 441 mg (19.2 mmol) of sodium was dissolved in 5 mL of dry ethanol under argon. When almost all of the sodium was dissolved, 2.92 mL (3.1 g, 19.2 mmol) of diethyl malonate was added to the ethoxide solution. Some solid precipitated out of solution. 4.0 g (9.6 mmol) of compound V was added and the mixture was refluxed under argon at 100 C for 70 hours. After cooling, the reaction mixture was filtered and washed with ethanol. Water was added to the filtrate and a white solid precipitated out of solution. The solid (779 mg, mostly of unreacted starting material) was filtered away. The filtrate was then acidified to pH ~2 and then extracted into ethyl acetate. The organic layer was then dried with MgSO$_4$ and filtered. After removing the solvent, 1.6 g (3.3 mmol) of a yellow oil was recovered (34%). $^1$HNMR (CDCl$_3$) 4.22 (cm, 4H, NC$\underline{H}_2$ next to barbiturate). 3.63 (s, 2H, ring C$\underline{H}_2$), 2.99 (cm, 2H, C $\underline{H}_2$ next to carbamate), 1.53 (cm, 4H, NCH$_2$C$\underline{H}_2$), 1.34 (s, 9H, t-butyl), 1.1–1.3 (cm, bulk C$\underline{H}_2$ s), 0.85 (t, J=7.4 Hz, n-butyl methyl).

To prepare compound VII, 1 mL of trifluoroacetic acid (TFA) was added with stirring to 200 mg (0.41 mmol) of compound VII dissolved in 3 mL of CH$_2$Cl$_2$. After 1.25 hours, all the solvent was removed under reduced pressure. One equivalent each of N-[5-(phenylamino)-2,4-pentadienylidene]aniline monohydrochloride and 1,3-di-n-butylthiobarbiturate was added and all three components dissolved in 1 mL pyridine and left overnight. The product was purified from the other pentamethine oxonols by flash chromatography. The nonpolar products were eluted with CHCl$_3$/CH$_3$OH (9:1). The pure product containing the linker eluted with CHCl$_3$/CH$_3$OH (1:1). The product was bound very tightly to the silica gel and only 10 mg of product was recovered. $^1$HNMR (CDCl$_3$/CD$_3$OD) 7.5–7.8 (cm, 4H, vinyl methines), 7.35 (t, J=~14 Hz, 1H, central methine), 4.34 (br t, ~10H, NC$\underline{H}_2$ next to barbiturate), 2.72 (cm, ~3H, C$\underline{H}_2$ next to amine), 1.4–1.7 (br cm, ~12H, NCH$_2$C$\underline{H}_2$), 1.0–1.4 (cm, ~40H, bulk C$\underline{H}_2$ s), 0.81 (t, J=7.3 Hz, 9H, n-butyl methyl).

(B) This particular example is with reference to FIGS. 15 and 16.

N-butyl-N-5-pentanol thiourea (6):

5-amino-1-pentanol (1.416 mL, 13 mmol) was dissolved in 7 mL of CH$_2$Cl$_2$. Under argon, butylisothiocynate (1.570 mL, 13 mmol) was added via syringe. After 2.5 h, the solvent was removed under vacuum leaving an oil. Under high vacuum, the oil was freeze dried 2× with liquid nitrogen and left under reduced pressure over night. The next morning 2.615 g of pure solid product was collected (12 mmol, 92%). $^1$H NMR (CDCl$_3$): d 5.90 (br s, 2H, NH), 3.66 (t, J=6.2 Hz, 2H, RCH$_2$OH), 3.42 (br m, 4H, NHCH$_2$R), 1.80 (br s, 1H, OH), 1.3–1.7 (unres. cm's, 10H, bulk methylenes), 0.94 (t, J=7.2 Hz, 3H, methyl). $^{13}$C NMR CDCl$_3$): d 181.5 (thiocarbonyl), 62.2 (RCH$_2$OH), 44.2 (NHCH$_2$R), 44.1 (NHCH$_2$R), 31.9 (CH$_2$), 31.0 (CH$_2$), 28.6 (CH$_2$), 23.0 (CH$_2$), 19.9 (CH$_2$), 13.6 (CH$_3$).

1-butyl,3-(S-pentanol) thiobarbiturate (7):

In dry EtOH, 345 mg (15 mmol) of Na was dissolved. After almost all of the Na had dissolved, diethylmalonate (2.278 mL, 15 mmol) was added under argon. The mixture was then heated to 60° C. to dissolve the precipitated sodium malonate. The heat was then removed and N-butyl-N-5-pentanol thiourea (6) (1.310 g, 6 mmol) was added. The reaction mixture was refluxed a 100° C. for 3.5 days. After cooling, the reaction mixture was filtered and washed with EtOH. An approximately equal volume of H$_2$O was added to the filtrate and acidified to pH 1–2 with conc. HCL. The aqueous solution was extracted 3× with 1:1 EtOAc/hexanes. The combined extracts were dried with MgSO$_4$, filtered, and concentrated leaving an oil. TLC EtOAc/MeOH (4:1) showed that in addition to the major barbiturate product there were two nonpolar impurities. Flash silica gel chromatography afforded some purification (4×17 cm), eluting with EtOAc/MeOH (4:1). The material was still an oil and a second column was done eluting with CHCl$_3$/MeOH/AA (90:8:2). Despite being an oil, 0.726 g (2.54 mmol, 42%) of pure product was recovered. $^1$H NMR (CDCl$_3$): d 4.31 (cm, 4H, NCH$_2$R), 3.71 (br s, 2H, ring methylene), 3.63 (t, J=6.3 Hz, 2H, RCH$_2$OH), 2.75 (br s, 1H, OH), 1.5–1.8 (cm, 6H, bulk methylenes), 1.2–1.5 i(cm, 4H, bulk methylenes), 0.94 (t, J=7.2 Hz, 3H, methyl).

1-butyl,3-(5-bromopentane)thiobarbiturate (8):

(7) (98 mg, 343 umol) was dissolve in 600 uL dry CH$_2$Cl$_2$ and mixed with carbon tetrabromide (142 mg, 429 umol). The solution was cooled on ice and triphenylphosphine (135 mg, 515 umol) was added. The solution bubbled and turned yellow immediately. After 30 min. the solvent was removed and hexane was added to the solid residue. The mixture was allowed to stir overnight. TLC showed only 1 barbiturate in hexane solution along with triphenylphospine oxide. The impurity was removed by flash silica gel chromatography (2.5×22 cm) packed in EtOAc/MeOH (98:2). The nonpolar impurity was eluted off the column using the packing solvent followed by EtOAc/MeOH (90:10). The desired product was eluted with CHCl$_3$/MeOH/AA (93:5:2), yeilding 40 mg (115 umol, 34%). $^1$H NMR (CDCl$_3$): d 4.33 (cm, 4H, NCH$_2$R), 3.72 (s, 2H, ring methylene), 3.42 (t, J=6.7 Hz, 2H, RCH$_2$Br), 1.91 (cm, 2H, methylene), 1.66 (cm, 4H, methylenes), 1.52 (cm, 2H, methylene) 0.95 (t, J=7.2 Hz, 3H, methyl).

1,3-di-butyl-5-(3-phenylamino propendienyl) thiobalrbiturate (10):

Malonaldehyde bis(phenylimine) (500 mg, 1.69 mmol) was dissolved in 20 mL of dry DMF. Separately, 1,3 di-butyl thiobarbiturate (430 mg, 1.76 mmol) was dissolved in 5 mL dry pyridine and placed in a 10 mL dropping funnel. The thiobarbiturate solution was slowly added over 5 min and the reaction was left stirring for 5 h. About 20 mL of water was added to the mixture and a yellow solid precipitated out of solution. The solid was filtered and dried yielding 575 mg (1.5 mmol, 89%). Minor impurities, including oxonol, were removed by flash silica gel chromatography (3×15 cm) eluting with EtOAc/hexanes (1:1). Some material precipitated on the column. Neverth.elessr after drying, 390 mg of pure product was recovered (1 mmol, 59%). $^1$H NMR (CDCl$_3$/MeOH): d 8.10 (d, J=3.0 Hz, 1H), 8.04 (s, 1H), 7.3–7.5 (cm, 3H), 7.1–7.25 (cm, 3H), 4.40 (cm, 4H, NCH$_2$R), 1.65 (cm, 4H, NCH$_2$CH$_2$R), 1.36 (cm, 4H, NCH$_2$CH$_2$CH$_2$CH$_3$), 0.90 (t, J=7.3 Hz, 6H, methyls).

1-(1,3-dibutyl thiobarbiturate)-3-(1-butyl,3-(5-hydroxypentyl)thiobarbiturate)trimethineoxonol triethylammonium Salt (11):

Compound (7) (85 mg, 297 umol) was mixed with (10) (114 mg, 297 umol) in 1.2 mL dry pyridine and left stirring for 17 h. TLC EtOAc/MeOH showed that there was 3 major oxonol products. Conc. HCL was added to 80% of the reaction mixture which caused a solid to precipitate out of solution. The solid was filtered and washed with water. After drying 220 mg of red solid was recovered. 96 mg of this solid was mixed with 1–2 mL EtOAc and filtered. The remaining solid was dissolved in CHCl$_3$/MeOH (95:5) and loaded on to a 19×2.5 cm silica gel column. Eluting with the same solvent, the most nonpolar oxonol was eluted off the column. The solvent was then changed to CHCl$_3$/MeOH/ Et$_3$N (90:8:2) to elute the middle band which was shown by NMR to be the desired product. After concentrating and drying, 18.5 mg (28 umol, 27%) of the pure product was recovered. $^1$H NMR (CDCl$_3$): d 8.60 (t, J=13.9 Hz, 1H, central methine), 8.14 (dd, J$_1$=13.8 Hz, J$_2$=2,2 Hz, 2H, methines), 4.45 (cm, 8H, NCH$_2$R), 3.66 (t, J=6.3 Hz, 2H, RCH$_2$OH), 3.20 (q, J=7.3 Hz, 6H, triethylammonium), 1.5–1.8 (cm, 8H, NCH$_2$CH$_2$R), 1.2–1.5 (cm, 10H, bulk methylenes), 1.35 (t, J=7.3 Hz, 9H, triethylammonium), 0.95 (t, J=7.2 Hz, 9H, terminal methyl). MS.

1-(1,3-dibutyl thiobarbiturate)-3-(1-butyl-3-(5-tosyloxypentyl)thiobarbiturate)trimethineoxonol (12):

In 4 mL pyridine, (11) (86.1 mg, 131 umol) was mixed with tosyl chloride (333 mg, 1.75 mmol). The reaction mixture was stirred for 3.5 h before the solvent was removed under vaccuum. The residue was dissolved in EtOAc and washed with 1 M HCL, followed by sat. brine 2×. TLC EtOAc/MeOH (9:1) showed that most of the starting material was converted to a more non polar product. However, a polar oxonol impurity was evident and the material had to be further purified by flash chromatography. The column was packed in CHCl$_3$/MeOH (97:3). It was necessary to increase the polarity to CHCl$_3$/MeOH (92:8) in order to elute off the product. The fractions containg the desired product were combined and dried, yielding 74.8 mg (102 umol, 78%) of product. $^1$H NMR (CDCl$_3$): d 8.50 (t, 1H, central methine), 7.92 (dd, J$_1$=14 Hz, J$_2$=2 Hz, 2H, methines), 7.81 (d, 2H, tosyl), 7.35 (d, J=8.2 Hz, 2H, tosyl), 4.37 (cm, 8H, NCH$_2$R), 4.09 (br t, 2H, RCH$_2$OTs), 2.45 (s, 3H, tosyl methyl), 1.2–1.9 (unres. cm, bulk methylenes), 0.91 (t, J=7.2 Hz, 9H, terminal methyl).

Example IX

Synthesis of Fluorescent Lanthanide Chelates with A Single Negative Charge

Terbium(III) Bis-(N,N'-bis(salicylidene)ethylenediamine) piperidinium Salt, Hpip$^+$ Tb(SALEN)$_2$$^-$:

N,N'-bis(salicylidene)ethylenediamine (SALEN) (0.719 g, 2.68 mmol) was dissolved in 40 mL MeOH at 60° C. Terbium chloride hexahydrate (0.5g, 1.34 mmol) dissolved in 1 mL water was added to the solution. Piperidine (536 µL, 5.42 mmol) was added and a yellow precipitate immediately formed. After 1 h, the heat was removed and the reaction mixture was left stirring overnight. The solid was filtered and dried yielding 709 mg (0.91 mmol, 68%) of the desired complex. Electrospray (neg. ion) MS [MeOH/H$_2$O: 95/5] (peak, rel. int.) 691.2 (M$^{-1}$, 100) calc. M$^{-1}$=691.5 amu.

Europium(III) Bis-(N,N'-bis(salicylidene) ethylenediamine)piperidinium, Hpip$^+$ Eu(SALEN)$_2$$^-$:

N,N'-bis(salicylidene)ethylenediamine (SALEN) (0.360 g, 1.34 mmol) was dissolved in 40 mL MeOH and piperidine (298 µL, 3.02 mmol) at 60° C. Europium chloride hexahydrate (0.246 g, 0.67 mmol) dissolved in 0.5 mL water was added to the solution and a yellow precipitate immediately came out of solution. After 1 h, the heat was removed and the reaction mixture was left for 2 hours. The solid was filtered and dried yielding 341 mg (0.44 mmol, 66%) of the desired complex.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A composition comprising a living cell, said composition comprising:
   a) a first reagent, comprising: a hydrophobic fluorescent anion that redistributes from one side of a membrane of said living cell to a second side of said membrane in response to potential across said membrane, and
   b) a second reagent which binds to said first side or said second side of said membrane and which undergoes energy transfer with said first reagent or quenches fluorescence of said first reagent.

2. The composition of claim 1, wherein said living cell is a mammalian cell.

3. The composition of claim 1, wherein said first reagent comprises a lanthanide chelate.

4. The composition of claim 1, wherein said first reagent comprises a tetraaryl borate.

5. The composition of claim 1, wherein said first reagent comprises a polymethine oxonol.

6. The composition of claim 1, wherein said second reagent comprises a fluorescently labeled protein or peptide.

7. The composition of claim 1, wherein said second reagent comprises a green fluorescent protein from Aequorea Victoria.

8. The composition of claim 1, wherein said second reagent comprises a Cou-N-linked amphipathic lipid, wherein: Cou is of the formula:

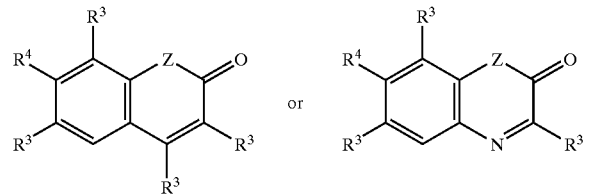

wherein:
each $R^3$, which may be the same or different, is independently selected from the group consisting of H, halogen, lower alkyl, CN, $CF_3$, $COOR_5$, $CON(R^5)_2$, $OR^5$, an attachment point;
$R^4$ is selected from the group consisting of $OR^5$ and $N(R^5)_2$;
Z is O, S or $NR^5$; and
each $R^5$, which may be the same or different, is independently selected from the group consisting of H, lower alkyl and an alkylene attachment point.

9. The composition of claim 2, wherein said mammalian cell is selected from the group consisting of neurons, cardiac cells, lymphocytes, nerve cells and muscle cells.

10. The composition of claim 2, wherein said mammalian cell is a primary culture.

11. The composition of claim 2, wherein said mammalian cell is selected from the group consisting of LM (TK-) cells, HEK293 (Human embryonic kidney cells), 3T3 fibroblasts, COS cells, CHO cells, RAT1 and HepG2 cells.

12. The composition of claim 2, wherein said membrane is the plasma membrane of said mammalian cell.

13. The composition of claim 2, wherein said membrane is a mitochondrial membrane of said mammalian cell.

14. The composition of claim 2, wherein said mammalian cell is voltage clamped.

15. The composition of claim 2, wherein said mammalian comprises at least one exogenous ion channel, ion transporter, ion pump or ion exchanger.

16. The composition of claim 5, wherein said polymethine oxonol has the general formula:

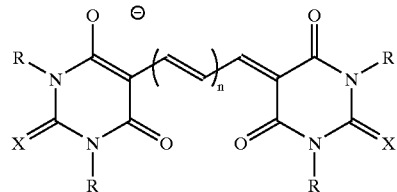

wherein:
R is independently selected from the group consisting of H, hydrocarbyl and heteroalkyl;
X is oxygen or sulfur; and
n is an integer from 1 to 3;
and salts thereof.

17. The composition of claim 16, wherein said X is sulfur.

18. The composition of claim 16, wherein said R is a $C_{4-40}$ alkyl group.

19. The composition of claim 16, wherein said R is a $C_{5-20}$ alkyl group.

20. The composition of claim 6, wherein said second reagent comprises a fluorescently labeled protein.

21. The composition of claim 7, wherein said green fluorescent protein is either a native plasma membrane protein or to a motif that is attached to the plasma membrane.

22. The composition of claim 8, wherein at least one of said $R^3$ is a halogen.

23. The composition of claim 8, wherein said N-linked lipid amphipathic comprises a phospholipid.

24. The composition of claim 23, wherein said phospholipid is a phosphatidylethanolamine.

25. The composition of claim 23, wherein said phospholipid is a dilauroylphosphatidylethanolamine.

26. The composition of claim 23, wherein said phospholipid is a dimyristoylphosphatidylethanolamine.

27. The composition of claim 23, wherein said phospholipid is a dipalmitoylphosphatidylethanolamine.

28. The composition of claim 23, wherein said phospholipid is a disteroylphosphatidylethanolamine.

29. The composition of claim 23, wherein said phospholipid is a dioleoylphosphatidylethanolamine.

30. The composition of claim 23, wherein said Cou-N-linked lipid is 6-chloro-7-hydroxycoumarin-labeled phosphatidylethanolamine.

31. A composition comprising a living cell, comprising:
   a) a first reagent comprising a first FRET partner that is a hydrophobic fluorescent anion that redistributes from one side of a membrane of said living cell to a second side of said membrane in response to potential across said membrane, and
   b) a second reagent, comprising an Aequorea green fluorescent protein which is expressed within said living cell and is a FRET partner to said first reagent,
   wherein said first FRET partner and said second FRET partner exhibits a change in FRET in response to a change in transmembrane voltage potential.

32. The composition of claim 31, wherein said Aequorea green fluorescent protein is expressed as a fusion protein.

33. The composition of claim 31, wherein said Aequorea green fluorescent protein is fused to either a native plasma membrane protein or to a motif that is attached to the plasma membrane.

34. The composition of claim 31, wherein said Aequorea green fluorescent protein is targeted to the endoplasmic reticulum.

35. The composition of claim 31, wherein said Aequorea green fluorescent protein is targeted to the mitochondria.

36. A method for determining transmembrane potential comprising:
(a) introducing a first reagent into a sample comprising a living cell, said first reagent comprising a hydrophobic fluorescent anion, capable of redistributing from a first face of a membrane of said living cell to a second face of said membrane in response to membrane potential;
(b) introducing a second reagent into said sample, said second reagent being located adjacent to said first face or said second face of said membrane, said second reagent comprising a molecule capable of undergoing energy transfer by either (i) donating excited state energy to the fluorescent anion, or (ii) accepting excited state energy from said fluorescent anion;
(c) exposing said membrane to excitation light;
(d) detecting fluorescence emission of said fluorescent anion, wherein said molecule is a chromophore or a fluorophore;
(e) relating fluorescence emission of said fluorescent anion to transmembrane potential.

37. The method of claim 36, wherein energy transfer between said fluorescent anion and said second reagent is by fluorescent resonance energy transfer (FRET).

38. The method of claim 37, wherein said living cell is a mammalian cell.

39. The method of claim 38, wherein said mammalian cell is selected from the group consisting of L-M (TK-) cells, neuroblastoma cells, astrocytoma cells and neonatal cardiac myocytes.

40. The method of claim 36, wherein said fluorescent anion is selected from the group consisting of polymethine oxonols, tetraaryl borates and complexes of transition metals.

41. The method of claim 40, wherein said fluorescent anion is a polymethine oxonol of the formula

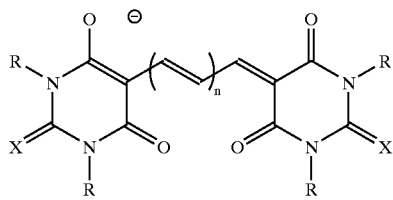

wherein:
R is independently selected from the group consisting of H, hydrocarbyl and heteroalkyl;
X is oxygen or sulfur; and
n is an integer from 1 to 3;
and alts thereof.

42. The method of claim 41, wherein X is sulfur.

43. The method of claim 41, wherein: each R is identical and is a hydrocarbyl group selected from $C_{1-10}$ alkyl groups; and
n=2.

44. The method of claim 40, wherein said fluorescent anion is a tetraaryl borate of the formula

[(Ar$^1$)$_3$B—Ar$^2$—Y—FLU]— wherein:

Ar$^1$ is an aryl group;
Ar$^2$ is an arylene group;
B is boron;
Y is oxygen or sulfur; and
FLU is a neutral fluorophore; and derivatives thereof.

45. The method claim 44, wherein:
Ar$^1$ is trifluoromethylphenyl;
Ar$^2$ is tetrafluorophenyl; and
Y is oxygen.

46. The method of claim 44, wherein said neutral fluorophore is selected from the group consisting of bimanes, difluoroboradiazaindacenes and coumarins.

47. The method of claim 46, wherein said neutral fluorophore is a bimane of the formula

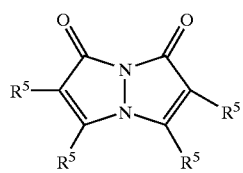

wherein:
each $R^5$, which may be the same or different, is independently H, lower alkyl or an alkylene attachment point.

48. The method of claim 46, wherein said neutral fluorophore is a difluoroboradiazaindacene of the formula

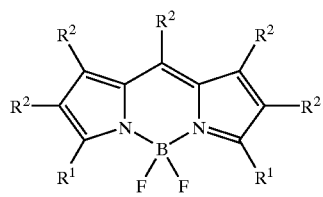

wherein:
each $R^1$, which may be the same or different, is independently selected from the group consisting of H, lower alkyl, aryl, heteroaromatic, aralkenyl and an alkylene attachment point;
each $R^2$, which may be the same or different, is independently selected from the group consisting of H, lower alkyl, phenyl and an alkylene attachment point.

49. The method of claim 46, wherein said neutral fluorophore is a coumarin of the formulas

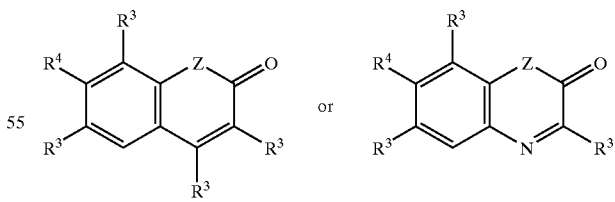

wherein:
each $R^3$, which may be the same or different, is independently selected from the group consisting of H, halogen, lower alkyl, CN, $CF_3$ and $OR^5$;
each $R^4$, which may be the same or different, is selected from the group consisting of H, $OR^5$ and an alkylene attachment point; and
Z is O, S or NR"; and R[5] is selected from the group consisting of H, lower alkyl and an alkylene attachment point.

50. The method of claim 46, wherein said neutral fluorophore is a complex of a transition metal of the formula

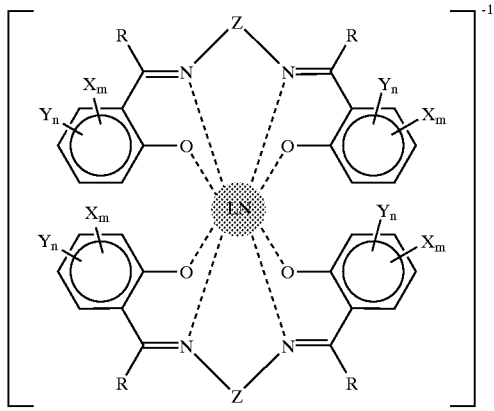

wherein:
Ln=Tb, Eu, or Sm;
R is independently H, C1–C8 alkyl, cycloalkyl or C1–C4 perfluoroalkyl;
X and Y are independently H, F, Cl, Br, I, $NO_2$, $CF_3$, lower (C1–C4) alkyl, CN, Ph, O-(lower alkyl), or OPh; or X and Y together are —CH=CH—; and
Z=alkylenediyl, heteroalkylenediyl or heterocyclodiyl.

51. The method of claim 50, wherein Z=1,2-ethanediyl, 1,3-propanediyl, 2,3-butanediyl, 1,2-cyclohexanediyl, 1,2-cyclopentanediyl, 1,2-cycloheptanediyl, 1,2-phenylenediyl, 3-oxa-1,5-pentanediyl, 3-aza-3-(lower alkyl)-1,5-pentanediyl, pyridine-2,6-bis(methylene) or tetrahydrofuran-2,5-bis(methylene).

52. The method of claim 46, wherein said neutral fluorophore is a complex of a transition metal of the formula

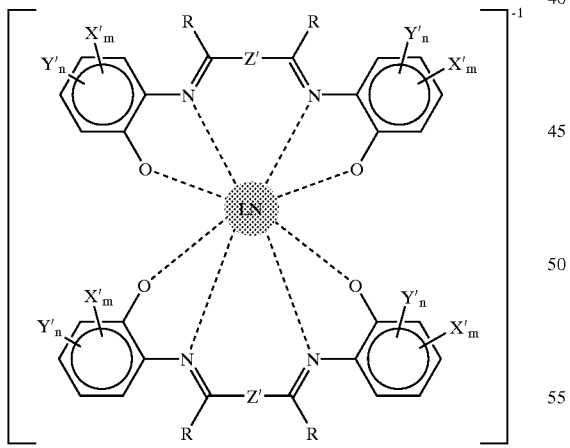

wherein:
Ln=Tb, Eu, or Sm;
R is independently H, C1–C8 alkyl, cycloalkyl or C1–C4 perfluoroalkyl;
X' and Y' are independently H, F, Cl, Br, I, $NO_2$, $CF_3$, lower (C1–C4) alkyl, CN, Ph, O-(lower alkyl), or OPh; or X' and Y' together are —CH=CH—; and
Z' is independently a valence bond, $CR_2$, pyridine-2-6-diyl or tetrahydofuran-2,5-diyl.

53. The method of claim 36, wherein said molecule is a fluorophore.

54. The method of claim 53, wherein said second reagent is selected from the group consisting of lectins, lipids, carbohydrates, cytochromes and antibodies, each being labeled with a fluorophore.

55. The method of claim 54, wherein said fluorophore is selected from the group consisting of xanthenes, cyanines and coumarins.

56. The method of claim 54, wherein said second reagent comprises a phospholipid.

57. The method of claim 36, wherein said first reagent and said second reagent are covalently joined by a linker.

58. The method of claim 57, wherein the linker is a compound of the formula:

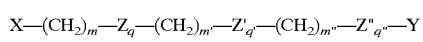

wherein:
X is a hydrophobic fluorescent anion selected from the group consisting of polymethine oxonols and fluorescent tetraaryl borates;
Y is a fluorescent second reagent selected from the group consisting of lectins and phospholipids;
Z, Z', Z" are independently O, S, SS, CO, COO;
m, m' and m" are integers from 0 to about 32;
q, q', and q" are independently 0 or 1; and
m+q+m'+q'+m"+q" is from about 20 to 40.

59. The method of claim 58, wherein said linker is a thioether.

60. A kit comprising:
(a) a first reagent comprising a hydrophobic fluorescent anion capable of redistributing from a first face of a membrane of a living cell to a second face of said membrane in response to changes in membrane potential; and
(b) a second reagent which labels said first face or said second face of said membrane, which said second reagent comprises a molecule capable of undergoing energy transfer by either (I) donating excited state energy to said fluorescent anion, or (ii) accepting excited state energy from said fluorescent anion;
wherein said molecule is a chromophore or a fluorophore.

61. The kit of claim 60, wherein, said first reagent is selected from the group consisting of polymethine oxonols, tetraaryl borates and complexes of transition metals.

62. The kit of claim 60, further comprising a solubilizing agent.

63. The kit of claim 60, wherein said fluorescent anion bears a single charge.

64. The kit of claim 60, wherein said fluorescent anion is a polymethine oxonol of the formula

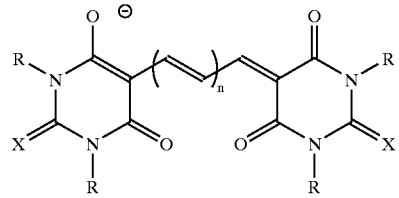

wherein:
R is independently selected from the group consisting of H, hydrocarbyl and heteroalkyl;

X is oxygen or sulfur; and n is an integer from 1 to 3;

and salts thereof.

65. The kit of claim 64, wherein X is sulfur.

66. The kit of claim 64, wherein:

each R is identical and is a hydrocarbyl group selected from $C_{1-10}$ alkyl groups; and n=2.

67. The kit of claim 60, wherein said fluorescent anion is a tetraaryl borate of the formula

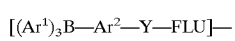

wherein:

$Ar^1$ is an aryl group;

$Ar^2$ is an arylene group;

B is boron;

Y is oxygen or sulfur; and

FLU is a neutral fluorophore; and derivatives thereof.

68. The kit of claim 67, wherein:

$Ar^1$ is trifluoromethylphenyl;

$Ar^2$ is tetrafluorophenyl; and

Y is oxygen.

69. The kit of claim 67, wherein said neutral fluorophore is selected from the group consisting of bimanes, difluoroboradiazaindacenes and coumarins.

70. The kit of claim 69, wherein said neutral fluorophore is a bimane of the formula

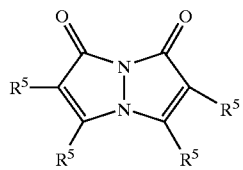

wherein:

each $R^5$, which may be the same or different, is independently H, lower alkyl or an alkylene attachment point.

71. The kit of claim 69, wherein said neutral fluorophore is a difluoroboradiazaindacene of the formula

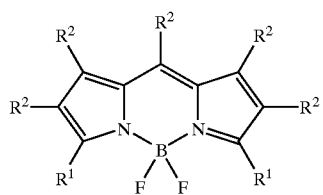

wherein:

each $R^1$, which may be the same or different, is independently selected from the group consisting of H, lower alkyl, aryl, heteroaromatic, aralkenyl and an alkylene attachment point;

each $R^2$, which may be the same or different, is independently selected from the group consisting of H, lower alkyl, phenyl and an alkylene attachment point.

72. The kit of claim 69, wherein said neutral fluorophore is a coumarin of formulas

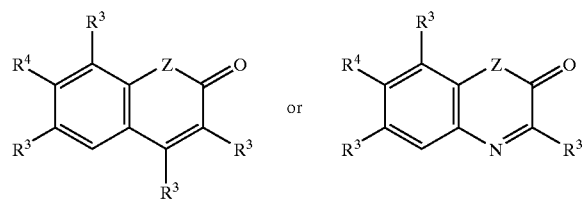

wherein:

each $R^3$, which may be the same or different, is independently selected from the group consisting of H, halogen, lower alkyl, CN, $CF_3$ and $OR^5$;

each $R^4$, which may be the same or different, is selected from the group consisting of H, $OR^5$ and an alkylene attachment point; and Z is O, S or NR"; and $R^5$ is selected from the group consisting of H, lower alkyl and an alkylene attachment point.

73. The kit of claim 69, wherein said neutral fluorophore is a complex of a transition metal of the formula

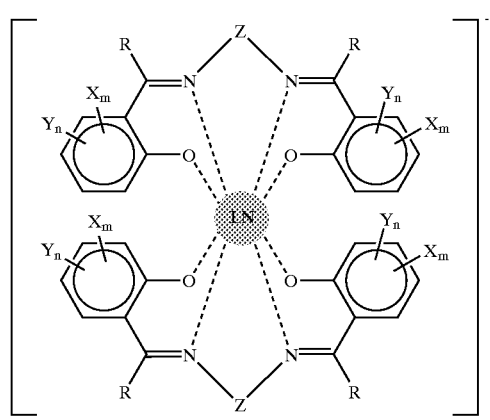

wherein:

Ln=Th, Eu, or Sm;

R is independently H, C1–C8 alkyl, cycloalkyl or C1–C4 perfluoroalkyl;

X and Y are independently H, F, Cl, Br, I, $NO_2$, $CF_3$, lower (C1–C4) alkyl, CN, Ph, O-(lower alkyl), or OPh; or X and Y together are —CH=CH—; and Z=alkylenediyl, heteroalkylenediyl or heterocyclodiyl.

74. The kit of claim 73, wherein

Z=1,2-ethanediyl, 1,3-propanediyl, 2,3-butanediyl, 1,2-cyclohexanediyl, 1,2-cyclopentanediyl, 1,2-cycloheptanediyl, 1,2-phenylenediyl, 3-oxa-1,5-pentanediyl, 3-aza-3-(lower alkyl)-1,5-pentanediyl, pyridine-2,6-bis(methylene) or tetrahydrofuran-2,5-bis(methylene).

75. The kit of claim 69, wherein said neutral fluorophore is a complex of a transition metal of the formula

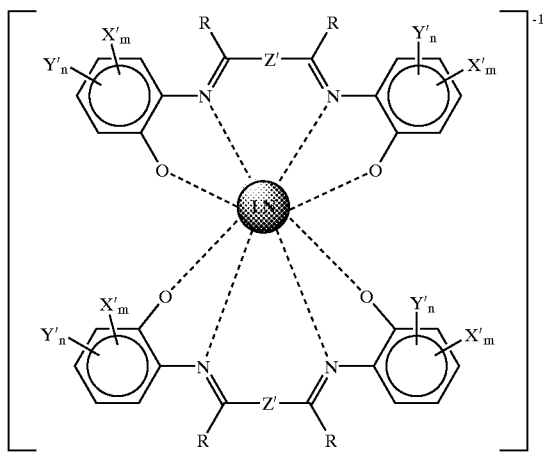

wherein:
- Ln=Tb, Eu, or Sm;
- R is independently H, C1–C8 alkyl, cycloalkyl or C1–C4 perfluoroalkyl;
- X' and V are independently H, F, Cl, Br, I, $NO_2$, $CF_3$, lower (C1–C4) alkyl, CN, Ph, O-(lower alkyl), or OPh; or X' and Y' together are —CH=CH—; and
- Z' is independently a valence bond, $CR_2$, pyridine-2-6-diyl or tetrahydofuran-2,5-diyl.

76. The kit of claim 60, wherein said second reagent comprises a fluorophore.

77. The kit of claim 76, wherein said second reagent is selected from the group consisting of lectins, lipids, carbohydrates, cytochromes and antibodies, each being labelled with a fluorophore.

78. The kit of claim 76, wherein said fluorophore is selected from the group consisting of xanthenes, cyanines coumarins.

79. The kit of claim 77, wherein said second reagent comprises a phospholipid.

80. The kit of claim 60, wherein said first reagent and said second reagent are covalently joined by a linker.

81. The kit of claim 80, wherein said linker is a compound of formula:

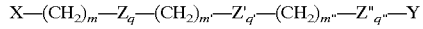

wherein:
- X is a hydrophobic fluorescent anion selected from the group consisting of polymethine oxonols and fluorescent tetraaryl borates;
- Y is a fluorescent second reagent selected from the group consisting of lectins and phospholipids;
- Z, Z', Z" are independently O, S, SS, CO, COO;
- m, m' and m" are integers from 0 to about 32;
- q, q', and q" are independently 0 or 1; and
- m+q+m'+q'+m"+q" is from about 20 to 40.

82. The kit of claim 81, wherein said linker is a thioether.

* * * * *